United States Patent
Chen

(10) Patent No.: US 10,858,305 B2
(45) Date of Patent: Dec. 8, 2020

(54) PERILLYL ALCOHOL-3-BROMOPYRUVATE CONJUGATE AND METHODS OF TREATING CANCER

(71) Applicant: NeOnc Technologies, Inc., Los Angeles, CA (US)

(72) Inventor: Thomas Chen, La Canada, CA (US)

(73) Assignee: NeOnc Technologies, Inc., Los Angeles, CA (US)

( * ) Notice: Subject to any disclaimer, the term of this patent is extended or adjusted under 35 U.S.C. 154(b) by 0 days.

(21) Appl. No.: 16/465,081

(22) PCT Filed: Nov. 29, 2017

(86) PCT No.: PCT/US2017/063706
§ 371 (c)(1),
(2) Date: May 29, 2019

(87) PCT Pub. No.: WO2018/102412
PCT Pub. Date: Jun. 7, 2018

(65) Prior Publication Data
US 2019/0337884 A1      Nov. 7, 2019

Related U.S. Application Data

(60) Provisional application No. 62/428,286, filed on Nov. 30, 2016.

(51) Int. Cl.
| | |
|---|---|
| *A61K 35/00* | (2006.01) |
| *A61K 31/22* | (2006.01) |
| *A61K 31/19* | (2006.01) |
| *A61P 35/04* | (2006.01) |
| *A61P 35/00* | (2006.01) |
| *C07C 69/716* | (2006.01) |
| *C07C 67/08* | (2006.01) |

(52) U.S. Cl.
CPC ............ *C07C 69/716* (2013.01); *A61K 35/00* (2013.01); *C07C 67/08* (2013.01)

(58) Field of Classification Search
CPC ........ A61K 35/00; A61K 31/22; A61K 31/19; A61P 35/00; A61P 35/04; C07C 69/716; C07C 67/08
See application file for complete search history.

(56) References Cited

U.S. PATENT DOCUMENTS

2010/0203110 A1*  8/2010  Geschwind .......... A61K 31/685
                                                     424/450
2016/0243114 A1*  8/2016  Chen .................... A61K 31/495

FOREIGN PATENT DOCUMENTS

WO    2010/091198 A1    8/2010

OTHER PUBLICATIONS

Chen et al., 2017, caplus an 2017:685995.*
International Search Report and Written Opinion dated Mar. 19, 2018 corresponding to International Patent Application No. PCT/US2017/063706.; 9 pages.
Chen et al. "A perillyl alcohol-conjugated analog of 3-bromopyruvate without cellular uptake dependency on monocarboxylate transporter 1 and with activity in 3-BP-resistant tumor cells," Cancer Letters, 2017, vol. 400, pp. 161-174.
"NEO 218," Drug Profile, Adis Insight, Aug. 1, 2016 (Aug. 1, 2016), pp. 1-6. Retrieved from the Internet:<http://adisinsight.springer.com/drugs/800046882> on Jan. 23, 2018 (Jan. 23, 2018).
Chen et al. "Perillyl Alcohol and Its Drug-Conjugated Derivatives as Potential Novel Methods of Treating Brain Metastases," Int J Mol Sci, 2016, vol. 17, No. 9, E1463.
Cho et al. "NE0212, temozolomide conjugated to perillyl alcohol, is a novel drug for effective treatment of a broad range of temozolomide-resistant gliomas," Mol Cancer Ther, 2014, vol. 13, No. 8, pp. 2004-2017.
Extended European Search Report in EP17876348.8 dated Jul. 7, 2020.

* cited by examiner

*Primary Examiner* — Sun Jae Yoo
(74) *Attorney, Agent, or Firm* — Leason Ellis LLP

(57) ABSTRACT

NEO218 (3-bromo-2-oxo-propionic acid 4-isopropenyl-cyclohex-1-enylmethyl ester), (see formula 1), is a novel molecule that was generated by covalent fusion of two unrelated agents: 3-bromopyruvate (3-BF; an alkylating agent that Inhibits cancer cell metabolism) and perillyl alcohol (POH; a natural monoterpene with anticancer properties). Methods of synthesizing NBO218, pharmaceutical compositions comprising NBO218 and methods of treating cancer using NBO218 are also disclosed.

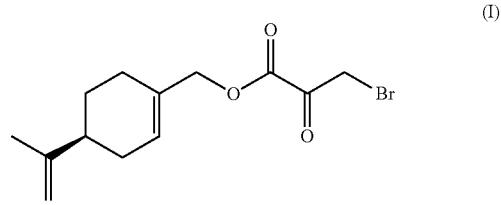

10 Claims, 26 Drawing Sheets
Specification includes a Sequence Listing.

Figure 10
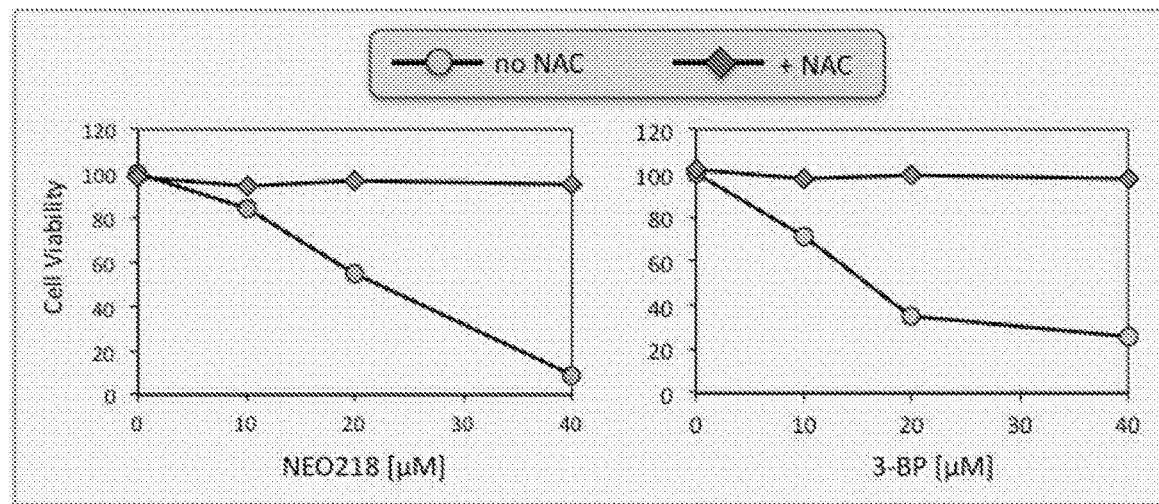
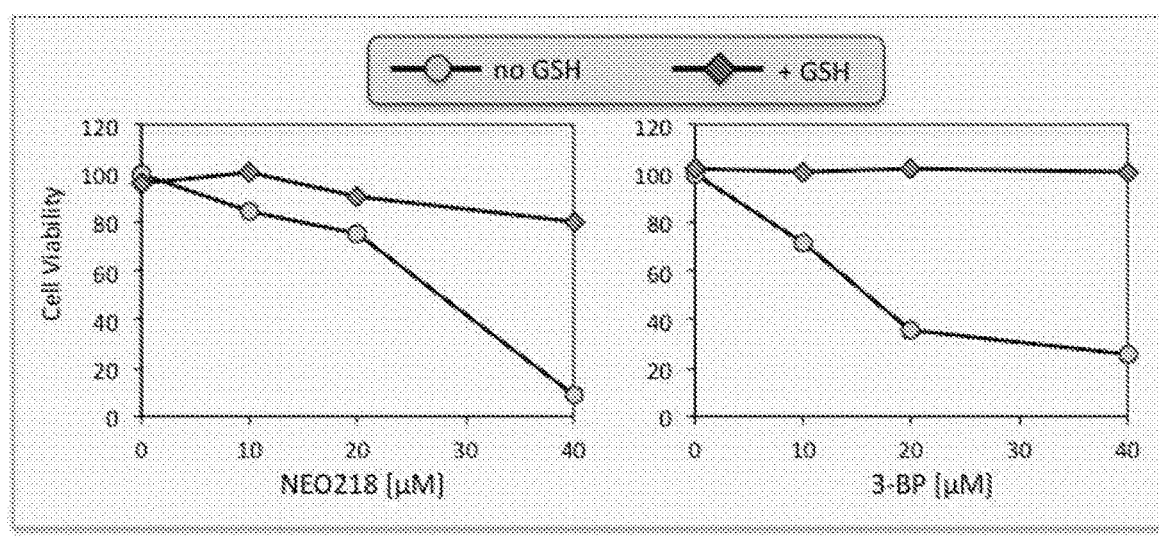

Figure 12
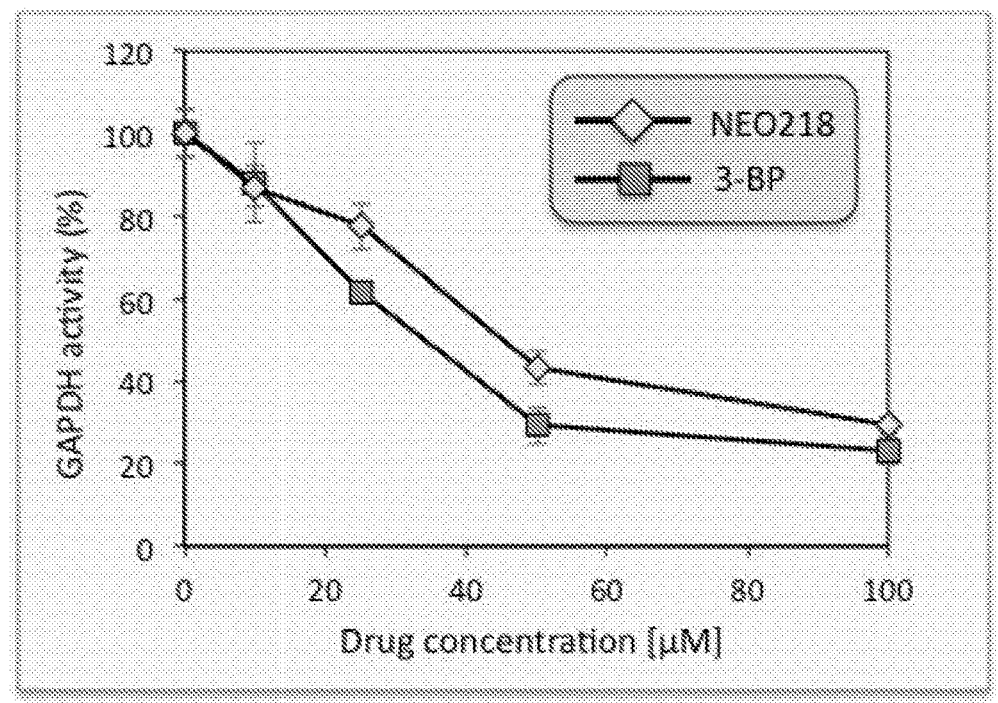
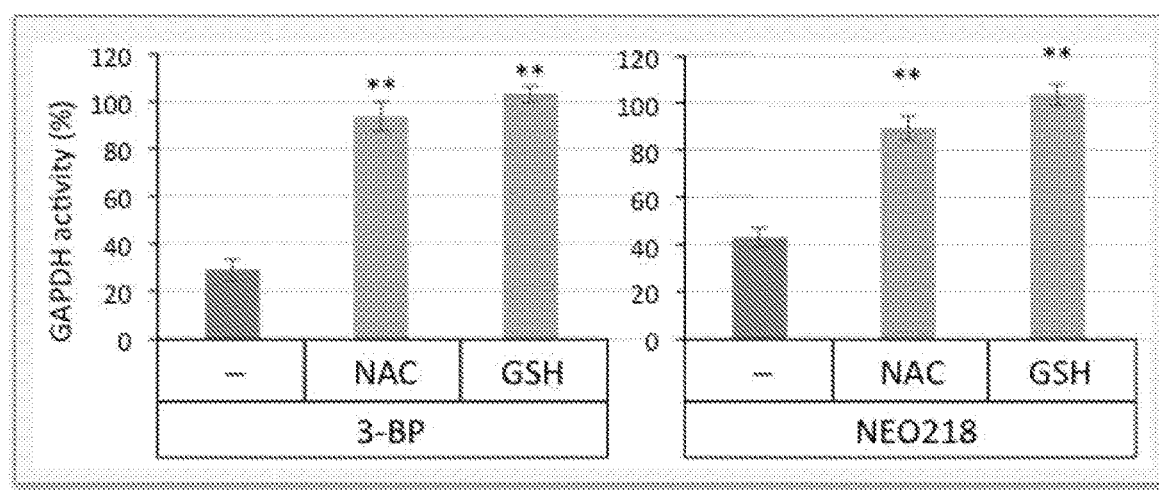

Figure 13

```
MVKVGVNGFGRIGRLVTRAAFNSGKVDVVA
INDPFIDLHYMVYMFQYDSTHGKFHGTVKA
ENGKLVINGKAITIFQERDPANIKWGDAGAEY
VVESTGVFTTMEKAGAHLKGGAKRVIISAPSA
DAPMFVMGVNHEKYDNSLKIVSNASCTTNC
LAPLAKVIHDHFGIVEGLMTTVHAITATQKTV
DGPSGKLWRDGRGAAQNIIPASTGAAKAVG
KVIPELNGKLTGMAFRVPTPNVSVVDLTCRLE
KAAKYDDIKKVVKQASEGPLKGILGYTEDQVV
SCDFNSATHSSTFDAGAGIALNDHFVKLISWY
DNEFGYSNRVVDLMVHMASKE
```

Figure 23
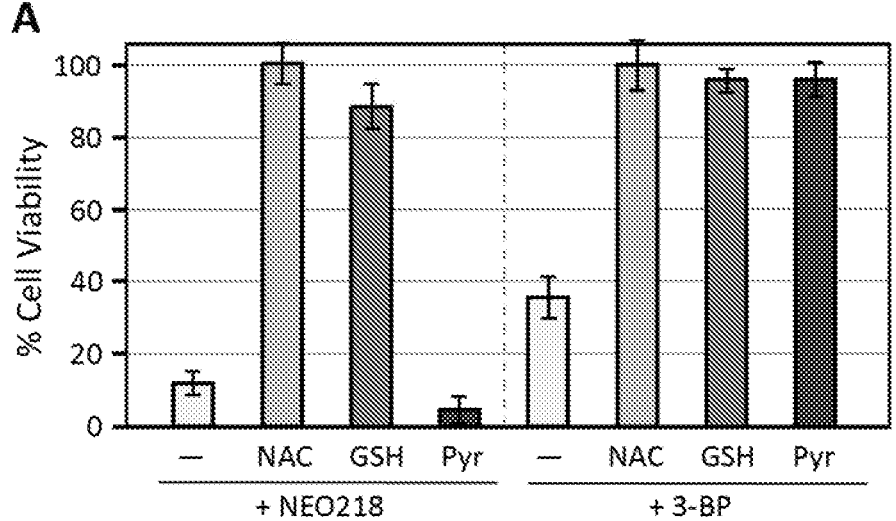
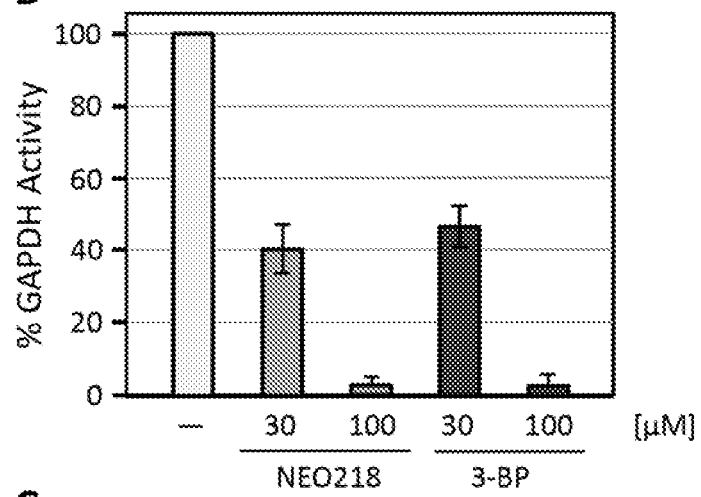
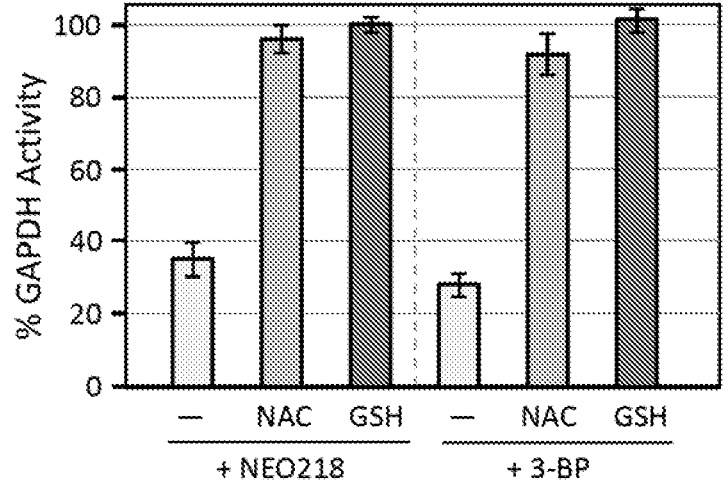

SEQUENCE LISTING

```
<160> NUMBER OF SEQ ID NOS: 1

<210> SEQ ID NO 1
<211> LENGTH: 21
<212> TYPE: DNA
<213> ORGANISM: Human

<400> SEQUENCE: 1
cagcagtatc ctggtgaata a                                               21
```

PERILLYL ALCOHOL-3-BROMOPYRUVATE CONJUGATE AND METHODS OF TREATING CANCER

FIELD OF THE INVENTION

The invention relates to a novel conjugate of perillyl alcohol with 3-bromopyruvate, and uses of said compound in the treatment of cancer.

BACKGROUND

Perillyl alcohol ("POH") is a monoterpene and a natural constituent of caraway, lavender and lilac oil, cherries, cranberries, sage, spearmint, celery seeds, and certain other plants [1]. Medical interest in this compound was generated by research findings showing that this monoterpene was able to inhibit the growth of tumor cells in cell culture and exert cancer preventive and therapeutic activity in a variety of animal tumor models (see detailed refs. in [2]). Its mode of action was thought to involve inhibition of Ras oncoprotein function [3], but newer studies have revealed additional intracellular targets potentially mediating its biological effects, such as telomerase [4], mammalian target of rapamycin (mTOR) [5,6], and sodium/potassium adenosine triphosphatase (Na/K-ATPase) [7]. Our own preclinical studies, we have identified endoplasmic reticulum (ER) stress as an important component of POH-induced tumor cell death [8].

Initially, clinical trials investigating the activity of POH in cancer patients were largely unsuccessful, primarily due to gastrointestinal toxicity resulting from the extremely high oral doses (gram quantities) required for systemic activity [9-13]. On the other hand, POH was efficacious and very well tolerated when smaller doses were given via intranasal inhalation delivery: in phase I/II studies in patients with recurrent malignant gliomas, there was encouraging activity and regression of tumor size when POH was administered via this alternative route [14-16]. In these latter studies, side effects of POH treatment were almost non-existent, even in patients treated for over 4 years [16], demonstrating that intranasal delivery (i) circumvents the dose-limiting restrictions of oral POH, and (ii) exerts activity at substantially lower overall dosages. In our own preclinical study, we demonstrated that intranasally administered POH exerted significant therapeutic activity in an intracranial mouse model of drug-resistant glioblastoma [8].

3-Bromopyruvate (3-BP, 3-bromopyruvic acid) is the alkaline form of 3-bromopyruvic acid:

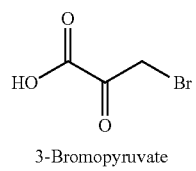

3-Bromopyruvate

It represents a synthetic, halogenated derivative of pyruvate (pyruvic acid), a key intermediate in several intracellular metabolic pathways. 3-BP acts as a highly reactive electrophilic alkylator [17], leading to the pyruvylation of receptive targets, such as the thiol group in cysteine-containing proteins [18,19]. A number of enzymes have been recognized as targets for 3-BP, such as, for example, hexokinase II (MK-II) [20] and glyceraldehyde-3-phosphate dehydrogenase (GAPDH) [21,22] in the glycolytic pathway, and succinate dehydrogenase (SDH) [21] in the tricarboxylic acid cycle and mitochondrial respiration. Inhibition of these enzymes by 3-BP leads to shut-down of cellular energy production and depiction of ATP pools, resulting in cell death [23].

3-BP has shown anticancer activity in multiple preclinical models. Its mode of anticancer action is thought to consist of a combination of energy shut-down, the production of reactive oxygen radicals, and inhibition of intracellular signaling [17,24-27]. The tumor specificity of this compound is generally attributed to tumor-specific upregulation of, and dependence on, HK-II and GAPDH in the glycolytic pathway (Warburg effect) [20]; therefore, inhibition of these targets preferentially impacts tumor cells. Other explanations include tumor-specific uptake of 3-BP via pyruvate-lactate transporters, such as monocarboxylate transporter 1 (MCT-1) [28], which is thought to be more highly expressed in tumor cells as compared to normal cells [29-31].

In xenograft animal tumor models, 3-BP revealed therapeutic potency against hepatocellular carcinoma in rabbits [32], rats [33] and mice [34]. Other in vivo tumor models investigated breast cancer in rats [35] and spontaneous pancreatic carcinoma [36], colon carcinoma [37], mesothelioma [38], and lymphoma [39] in mice. Aerosolized 3-BP decreased tumor multiplicity and tumor load in lungs of mice exposed to the carcinogen benzo(a)pyrene [40], microencapsulated 3-BP prevented tumor progression in an orthotopic pancreatic cancer mouse model [41], and wafers enabled local intracranial delivery of 3-BP for glioma therapy in rat brain [42]. As well, 3-BP has shown chemosensitizing effects when used together with certain chemotherapeutic agents in vitro and in vivo (see refs. in [23]).

Based on clinical use, there are two case reports of patients having been treated with 3-BP [25,43]. In one study, a young adult cancer patient with fibrolamellar hepatocellular carcinoma received repeated treatments with 3-BP, which was delivered via the Transcatheter Arterial Chemo-Embolization (TACE) method and was well tolerated. Although the patient eventually died, he did survive much longer than expected [43]. The other patient was a 28-year-old man who presented with stage IV metastatic melanoma and received intravenous infusion of 3-BP. This treatment appeared to have minimal toxicity, but its anticancer efficacy was low and the patient eventually died [25].

SUMMARY

In one aspect of the invention, there is provided a conjugate of perillyl alcohol and 3-bromopyruvate that is
a.

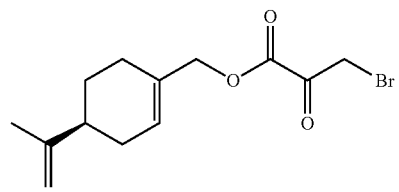 [SMILES: C=C(C)[C@@H]1CC=C(COC(=O)C(=O)CBr)CC1]

i. 3-bromo-2-oxo-propionic acid 4-isopropenyl-cyclohex-1-enylmethyl ester,
b. or a pharmaceutically acceptable salt thereof.

In a second set of embodiments, the invention is directed to a pharmaceutical composition comprising 3-bromo-2-oxo-propionic acid 4-isopropenyl-cyclohex-1-enylmethyl ester. In some of these embodiments the pharmaceutical composition further comprises a pharmaceutically acceptable excipient.

In a third set of embodiments, the invention is directed to a method of treating a cancer in a patient in need of such treatment comprising administering to said patient a therapeutically effective amount of 3-bromo-2-oxo-propionic acid 4-isopropenyl-cyclohex-1-enylmethyl ester. In some of these embodiments, said cancer is selected from the group consisting of lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer and cancer of the urinary system.

In a fourth set of embodiments, the invention is directed to a process for synthesizing 3-bromo-2-oxo-propionic acid 4-isopropenyl-cyclohex-1-enylmethyl ester comprising:

reacting 1,1-dichlorodimethyl ether with bromopyruvic acid to form 3-bromopyruvic chloride; and, reacting 3-bromopyruvic chloride with perillyl alcohol to form 3-bromo-2-oxo-propionic acid 4-isopropenyl-cyclohex-1-enylmethyl ester.

In some of these embodiments, said step of reacting 1,1-dichlorodimethyl ether with bromopyruvic acid is conducted at a temperature of about 0 to about 20° C. In some embodiments, said step of reacting 3-bromopyruvic chloride with perillyl alcohol is conducted at a temperature of about −10 to about 10° C. In some embodiments, said step of reacting 3-bromopyruvic chloride with perillyl alcohol is conducted in the presence of sodium bicarbonate and n-heptane.

In a fifth set of embodiments, the invention is directed product of the process according to any of the processes within the fourth set of embodiments.

BRIEF DESCRIPTION OF THE FIGURES

FIG. 10 displays plots of cell viability vs. drug concentration for NEO218 and 3-BP, with and without NAC and GSH.

FIG. 12, top panel, displays a plot of GAPDH activity vs. drug concentration for NEO218 and 3-BP; the lower panels display histograms of GAPDH activity for NEO218 and 3-BP with NAC, with GSH, and without either.

FIG. 13 displays the amino sequence (in one letter code) of the GAPDH protein, marked to indicate the presence of cysteine residues.

The following established human cell lines were used: (A) HCT116 colon carcinoma; (B) LN229, T98G, and U251 glioblastoma; (C) MCF7, MDA-MB-231, MDA-MB-468, BTM-12, and T47D breast carcinoma; and ME16C normal mammary gland epithelium cells (immortalized with telomerase). The bar graph shows the cytotoxic IC50 for each cell line after 24 hours of drug treatment with 3-BP (light gray) or NEO218 (dark gray), as determined by 24-hour MTT assay. Bars with error bars represent ≥3 measurements, whereas graphs without error bars show the average of two independent measurements. The middle panels show MCT-1 protein levels for each cell line, as determined by Western blot with actin as the loading control.

Figure 17:
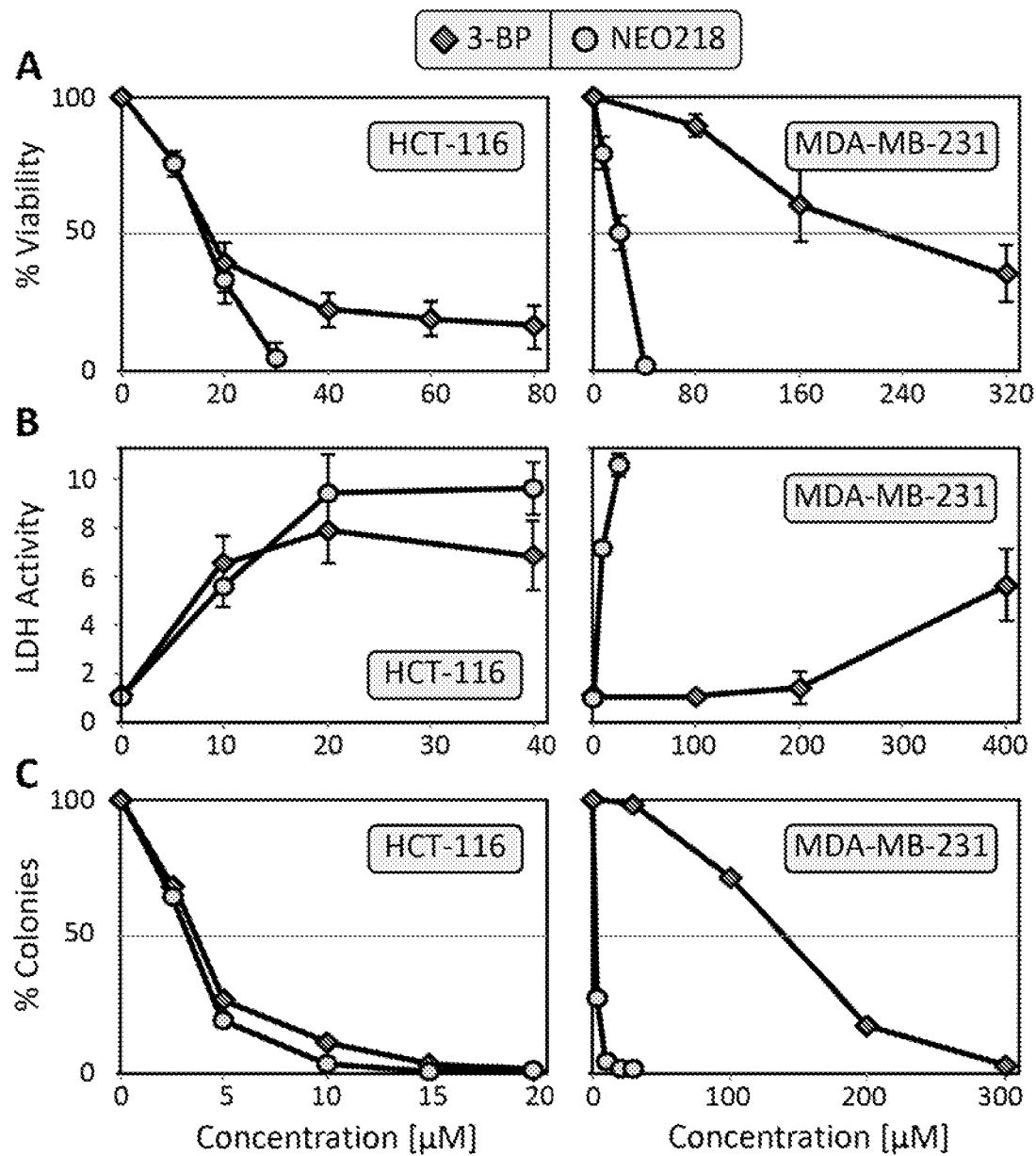

FIGS. 17A-17C. 3BP and NEO218 exert differential cytotoxic impact.

HCT116 (MCT-1 positive) and MDA-MB-231 (MCT-1 negative) cells were treated with increasing concentrations of 3-BP (diamonds) or NEO218 (circles). (A) MTT assay was performed after 24 hours. Viability of untreated cells was set at 100% (n=3). (B) LDH assay was performed after 16 hours. LDH release by untreated cells was set to 1. Relative fold increase is shown (n=3). (C) Shown is the relative number of colonies formed after treatment with drugs for 48 hours, followed by another 10-14 days in the absence of drug. Number of colonies from untreated control cells was set at 100% (shown is the average from two independent experiments). In all cases, cells also received vehicle only as a control; however, none of the assays revealed a difference between untreated or vehicle-treated cells.

Figure 18:
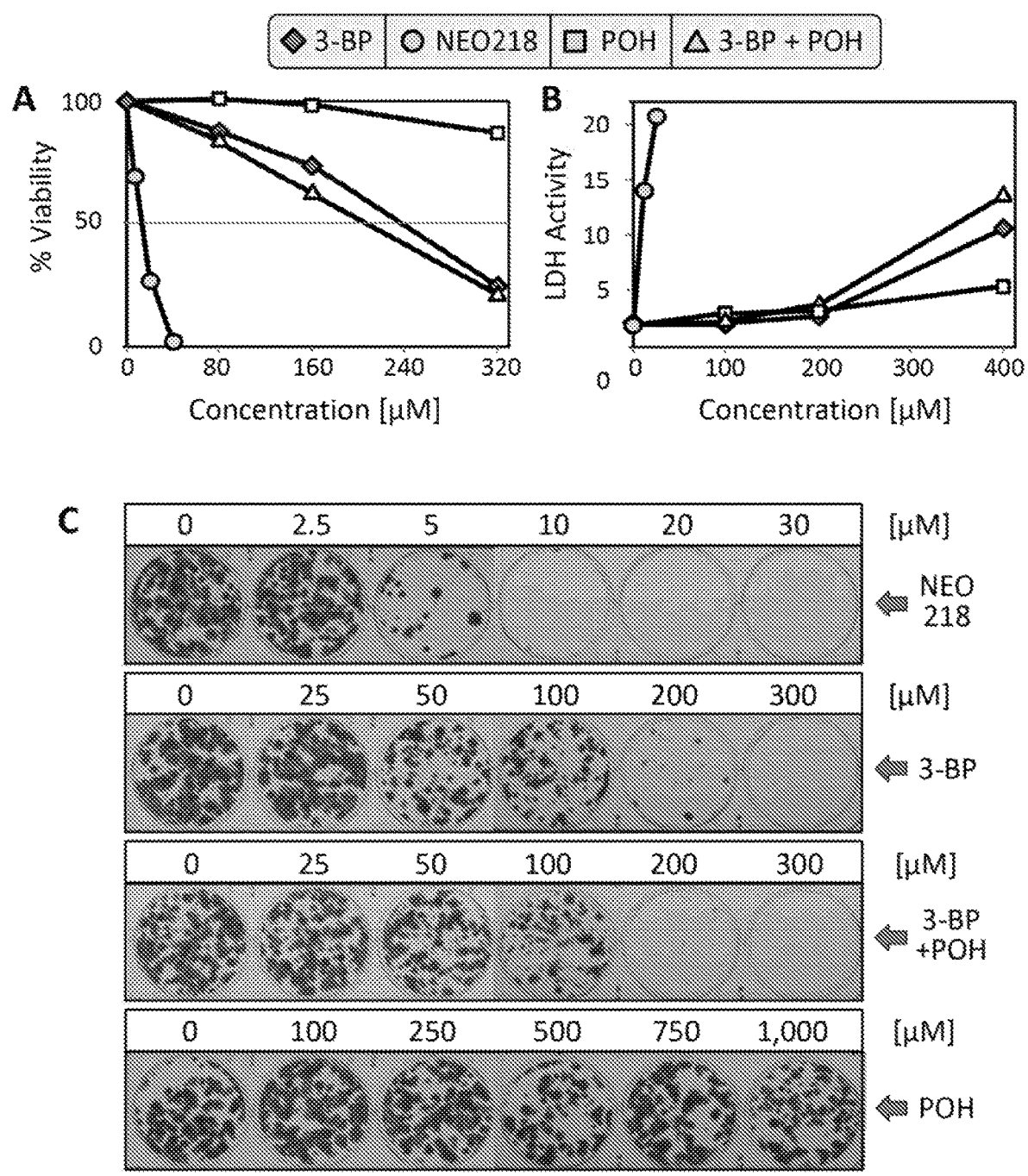

FIGS. 18A-18C: A mix of 3-BP+POH is unable to mimic high potency of conjugated NEO218.

MDA-MB-231 cells were treated with increasing concentrations of 3-BP (diamonds), NEO218 (circles), POH (squares), or equimolar ratios of 3-BP mixed with POH (triangles). (A) MTT assay was performed after 24 hours. Viability of untreated cells was set at 100% (data points are averages of 2 experiments). (B) LDH assay was performed after 24 hours. LDH release by untreated cells was set to 1. Relative fold increase is shown (averages from 2 experiments). (C) Representative photos show typical colony formation after initial 48 hours of drug treatment. In all cases of combination treatment with 3-BP mixed with POI (3-BP+POH), the indicated concentrations refer to each individual drugs, i.e., 100 µM 3-BP+POH means that 100 µM 3-BP was combined with 100 µM POH.

Figure 19:
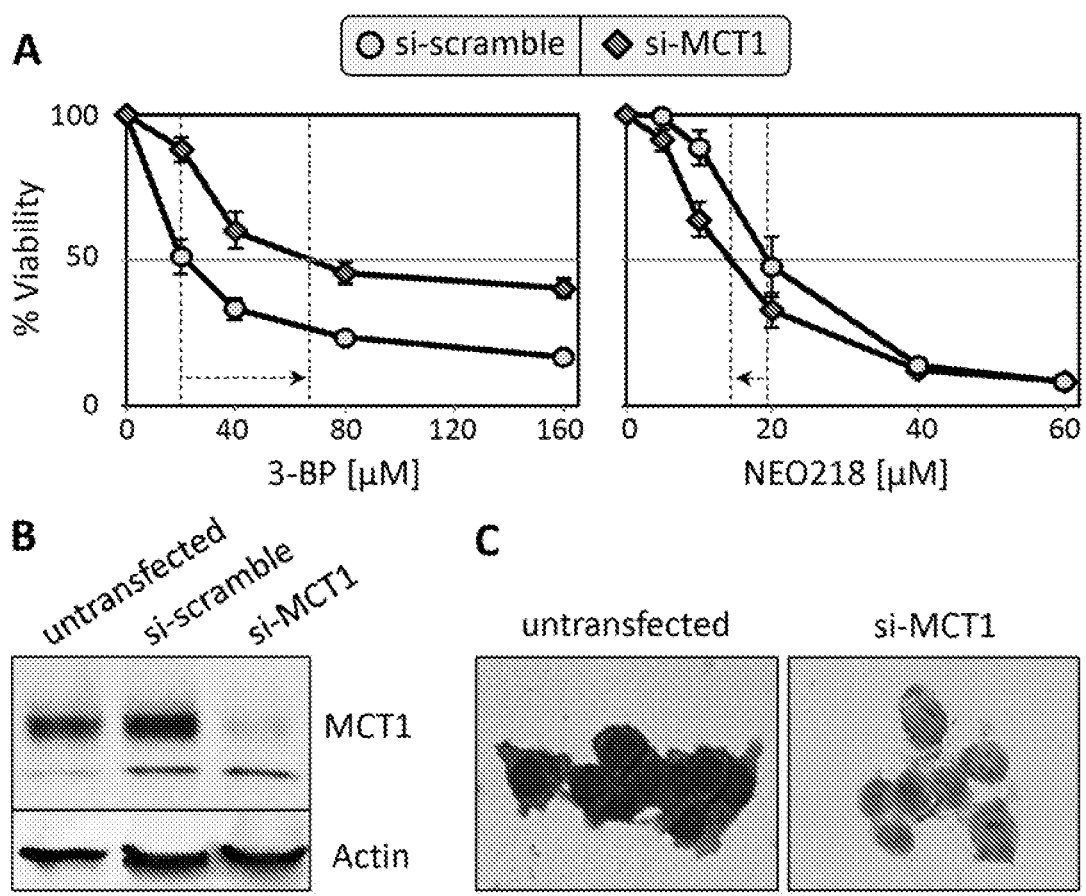

FIGS. 19A-19C: MCT-1 knockdown impacts cellular sensitivity to 3-BP, but not NEO218.

HCT116 cells were transfected with siRNA targeted at MCT-1 (circles), or with a scrambled control (diamonds). (A) Cellular sensitivity to 3-BP and NEO218 was determined by MTT assay. Dotted lines and arrow show the shift in IC50. Note pronounced shift to the right in 3-BP-treated cells (left, panel), compared to a minor shift to the left in NEO218-treated cells (right panel). (B) Knockdown of MCT-1 protein levels was confirmed by Western blot analysis with actin as the loading control. (C) MCT-1 knockdown was also confirmed at the individual cell level by immunocytochemistry. The two photos were similarly overexposed in order to emphasize the pronounced difference in MCT-1 levels.

Figure 20:
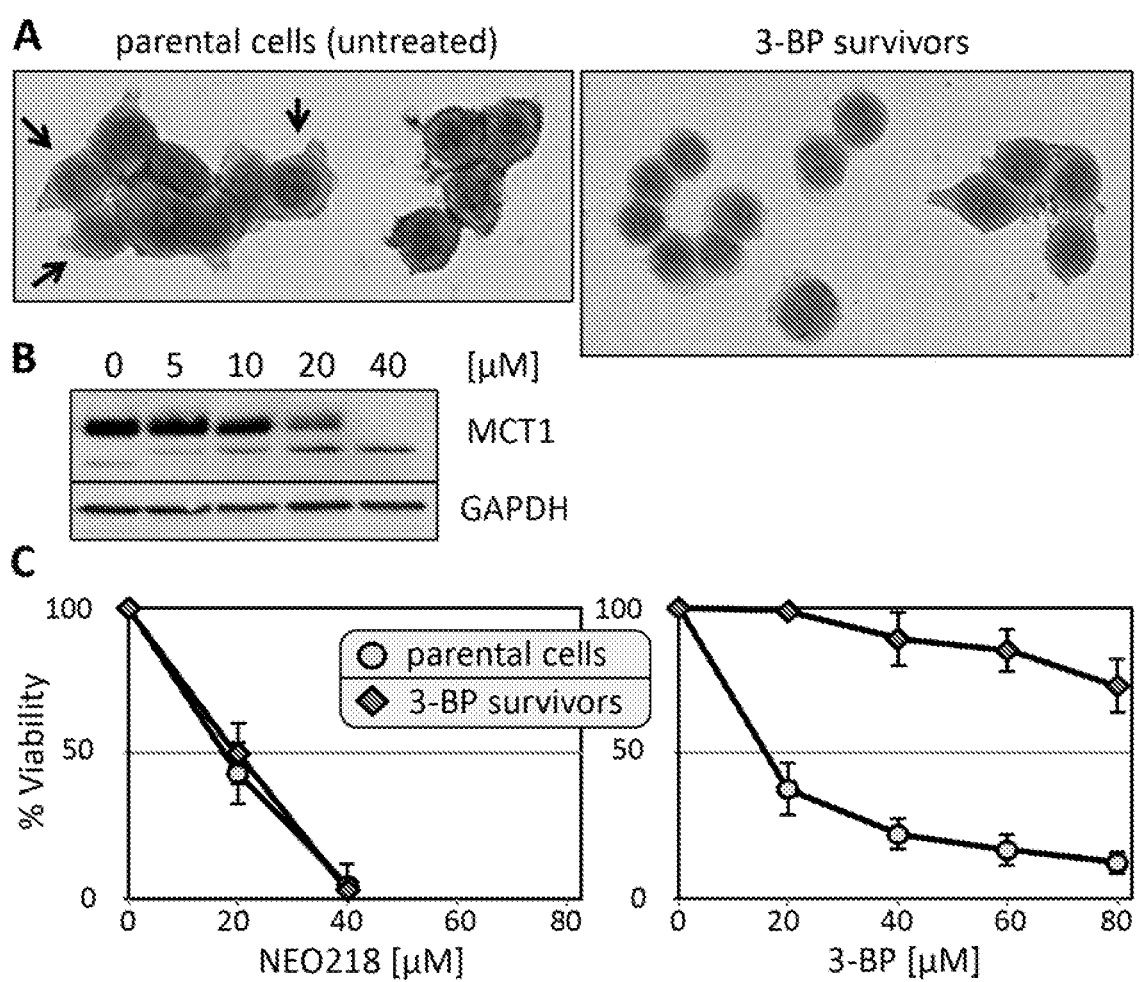

FIGS. 20A-20C: 3-BP treatment selects for resistant cells, which remain sensitive to NEO218.

(A) Immunostaining of HCT116 cells in the absence of any drug treatment (parental cells; left panel) and after 2-week recovery from highly toxic 48-hour treatment with 40 µM 3-BP (3-BP survivors; right panel). Arrows point to a few apparently MCT-1-negative cells among the otherwise MCT-1-positive parental population. Note preferential staining of the cell membrane in the positive cells, consistent with the known transmembrane location of MCT-1; no such staining could be detected in the 3-BP survivors. (B) Western blot analysis of MCT-1 expression levels two weeks after 48-hour treatment of cells with increasing concentrations of 3-BP. Consistent with IHC staining shown above, 40 µM 3-BP resulted in loss of MCT-1 protein. GAPDH was used as a loading control. (C) Chemosensitivity of 3-BP survivors were compared to parental cells in MTT assays. Both populations were treated with increasing concentrations of 3-BP or NEO218. Survival of untreated cells was set at 100% (n≥3±SE).

Figure 21:
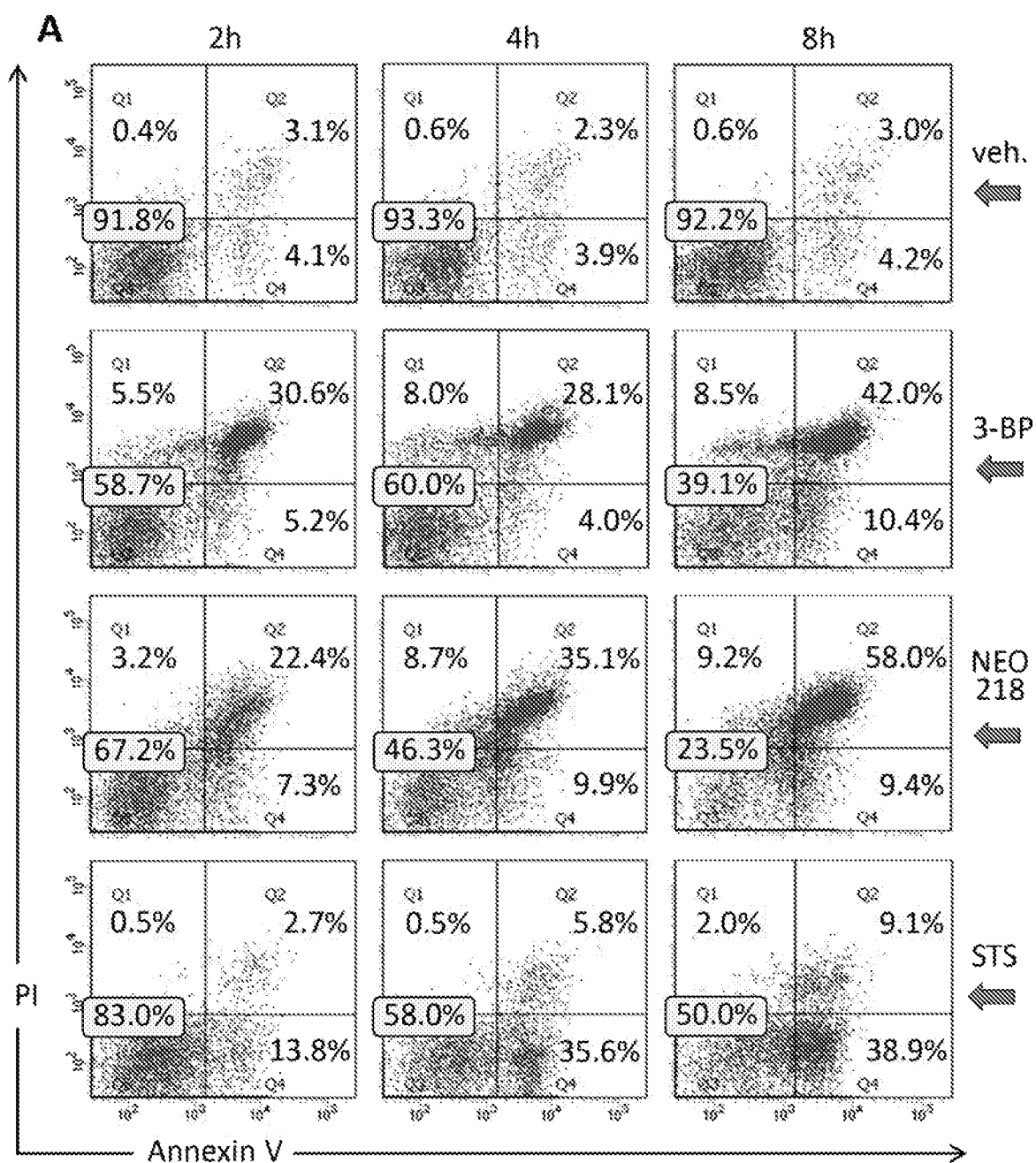
Figure 21:
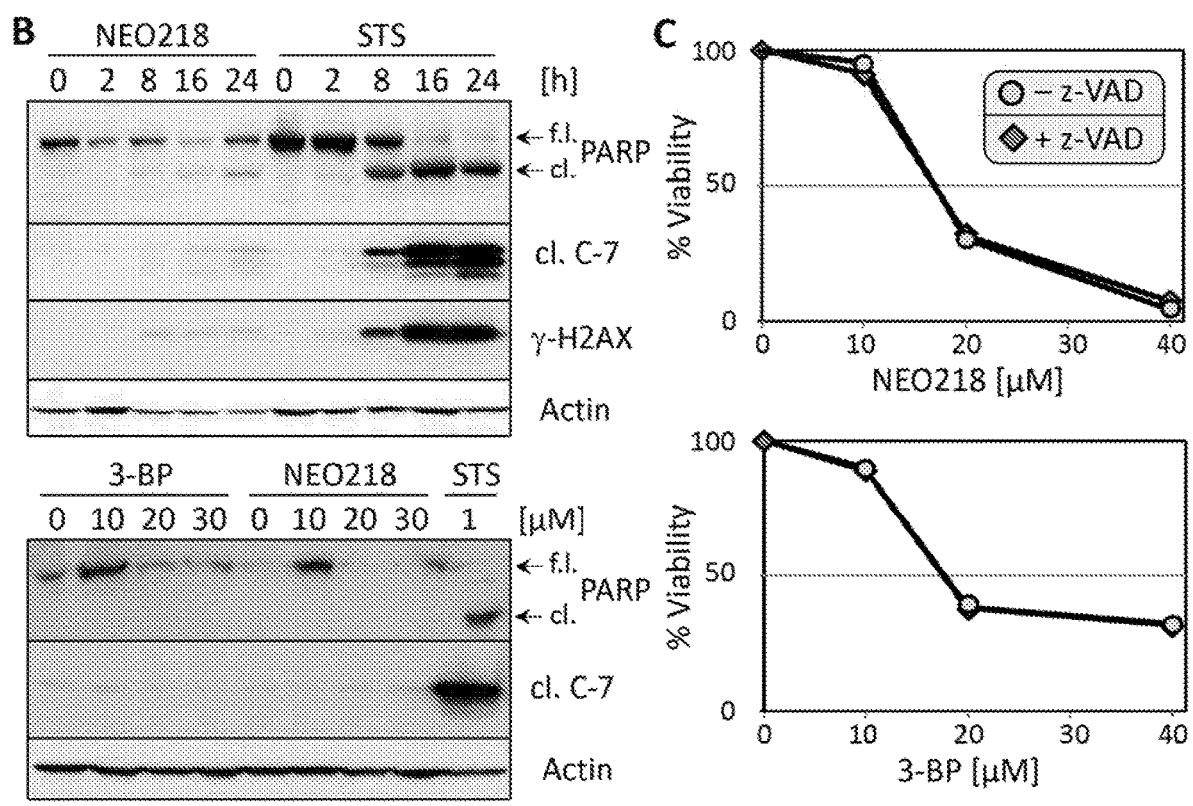

FIGS. 21A-21C: 3-BP and NEO218 cause necrosis.

(A) FACS analysis of HCT116 cells after treatment for 2, 4, or 8 hours with vehicle, 30 µM 3-BP, 30 µM NEO218, or 1 µM staurosporine (STS). Y-axis shows propidium iodide (PI) labeling and x-axis shows annexin V labeling. Upper two quadrants in each square show necrotic cells, whereas lower right quadrant shows apoptotic cells. (B) Western blot analysis of apoptotic markers. In the top section, MDA-MB-231 cells were treated with 30 µM NEO218 or 1 µM STS for various time points. In the lower section, HCT116 cells were treated with the indicated concentrations of 3-BP, NEO218, or STS for 16 hours. In all cases cell lysates were prepared and analyzed for the well-established apoptotic markers cleaved PARP, cleaved (i.e., activated) caspase 7 (cl. C-7), and phosphorylated (i.e., active) H2AX. Actin was used as a loading control. (C) HCT116 cells were pretreated with 50 µM Z-VAD-FMK for one hour, followed by the addition of increasing concentrations of 3-BP or NEO218. Cell viability was determined by MTT assay 24 hours later. Data points are averages from n=3.

Figure 22:
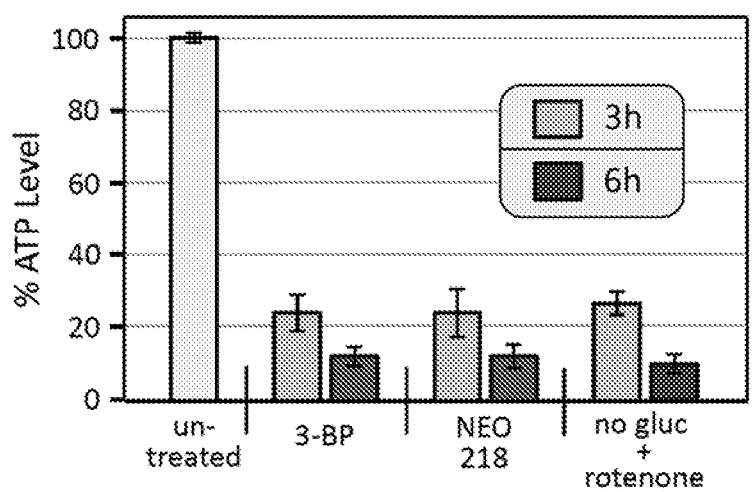

FIG. 22: 3-BP and NEO218 deplete cellular ATP pools.

HCT116 cells were treated with 40 µM 3-BP or NEO218. As a point of reference, cells were also exposed to 100 nM rotenone in glucose-free medium. ATP levels were determined after 3 and 6 hours. ATP levels in untreated cells were set at 100% (corresponding to 26.6 nmol per one million cells).

FIGS. 23A-23C: Supplemental antioxidants block drug effects, but added pyruvate causes differential outcome.

(A) HCT116 cells were treated with 40 µM 3-BP or NEO218 in the presence or absence of 1 mM NAC, 1 mM GSH, or 50 mM methyl-pyruvate (or sodium pyruvate, which produced similar outcomes). Cell viability was determined 24 hours later by MTT assay. (B) HCT116 cells were treated with 30 or 100 µM 3-BP or NEO218. After 30 minutes, cell lysates were prepared and analyzed for GAPDH activity. (C) Lysates from non-drug-treated MDA-MB-231 cells were mixed with 3-BP or NEO218 in the presence or absence of NAC or GSH at the concentrations mentioned in A. After 1 hour of incubation, GAPDH activity was determined. GAPDH activity in the absence of drug treatment was set at 100% (corresponding to 0.06 units/min×$10^6$ cells).

Figure 24:
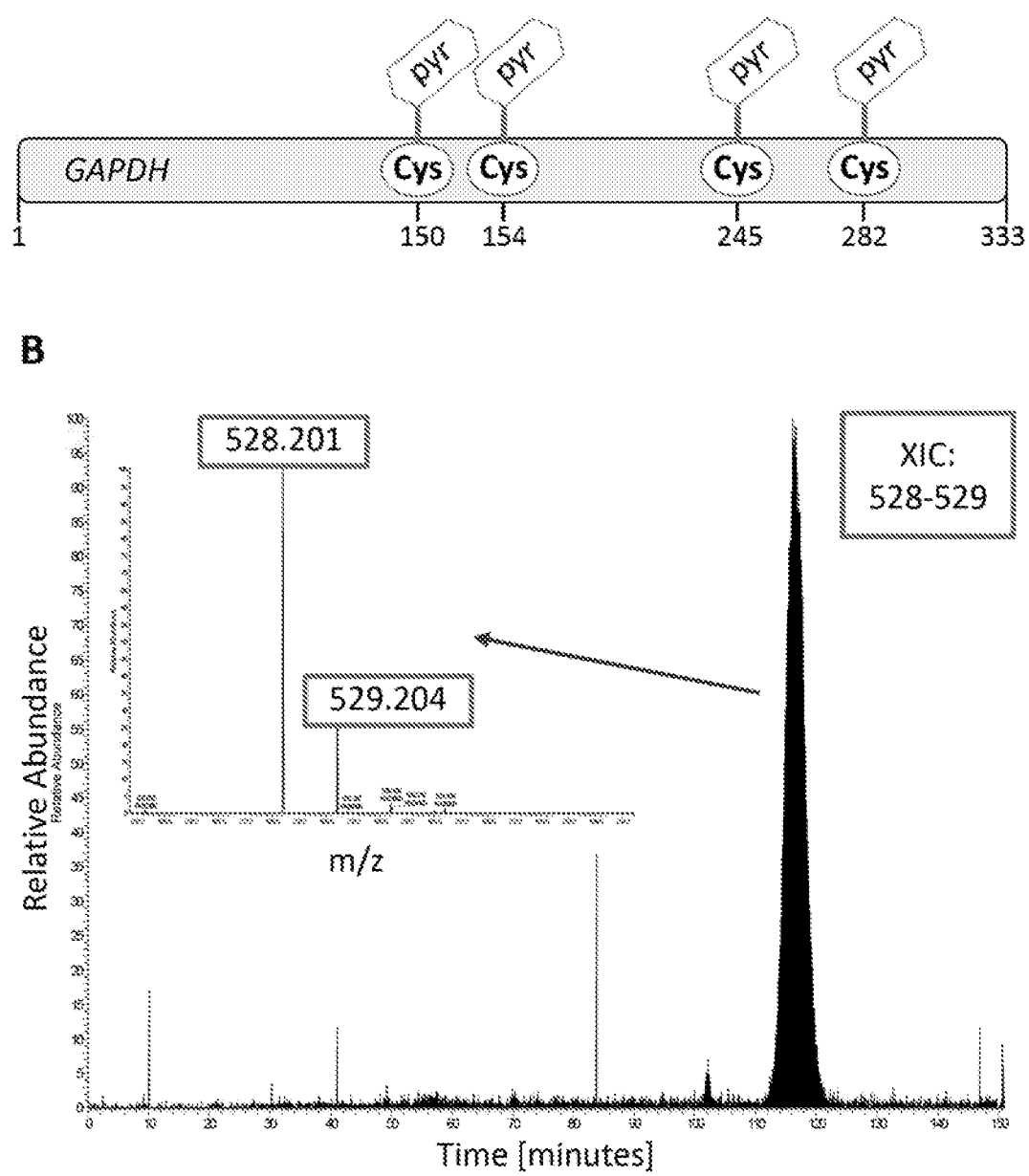
Figure 24:
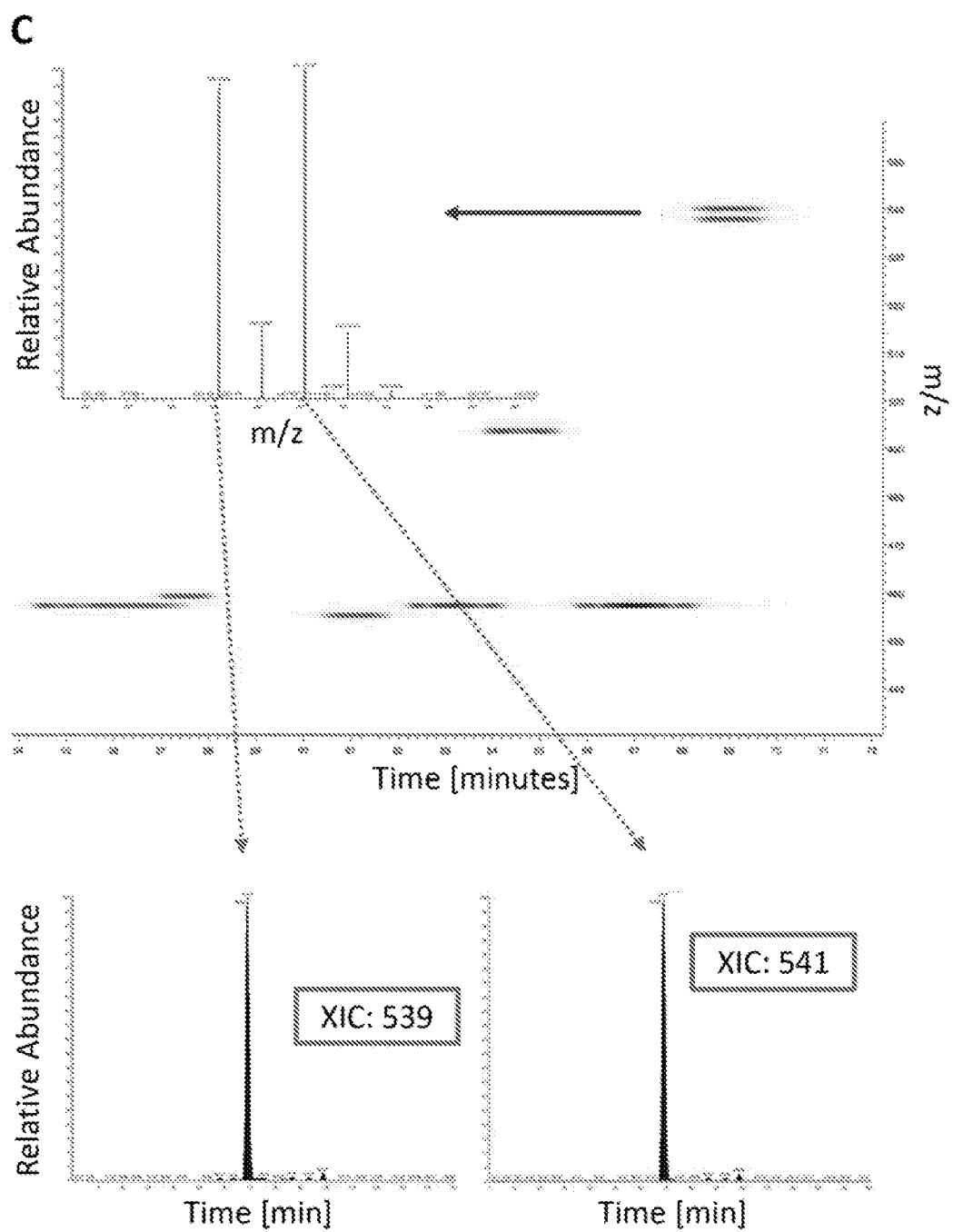

FIGS. 24A-24C: NEO218 directly interacts with GAPDH, GSH and NAC

Direct interaction of NEO218 with different targets was analyzed by LC/MS analysis. (A) Purified rabbit GAPDH protein was incubated with 3-BP or NEO218 for 15 minutes, followed by LC/MS analysis. GAPDH protein contains 4 cysteines (Cys) at the indicated positions, and all four were identified as being modified with a pyruvate moiety in the case of 3-BP, and a pyruvate-perillyl alcohol moiety in the case of NEO218 (indicated by pyr). (B) Extracted ion chromatogram (XIC) of the reaction products of NEO218 and GSH restricted to mass over charge (m/z) values between 528 and 529. The chromatogram (insert panel) shows the presence of a singly-charged reaction product with accurate ion mass of 528.201 (nominal mass peak) corresponding to nucleophilic substitution reaction of NEO218 and GSH. Location and relative size of the peak at 529.204 corresponds to the $^{13}C$ isotope peak of the reaction product. (C) Reaction of NAC with NEO218 yielded several products shown in the ion map (top panel). The co-eluting twin isotope at m/z 539 and 541 distributed equally (insert in top panel) and was selected for further analysis, as shown in the two chromatograms in the bottom panels.

DETAILED DESCRIPTION OF THE INVENTION

Figure 1:
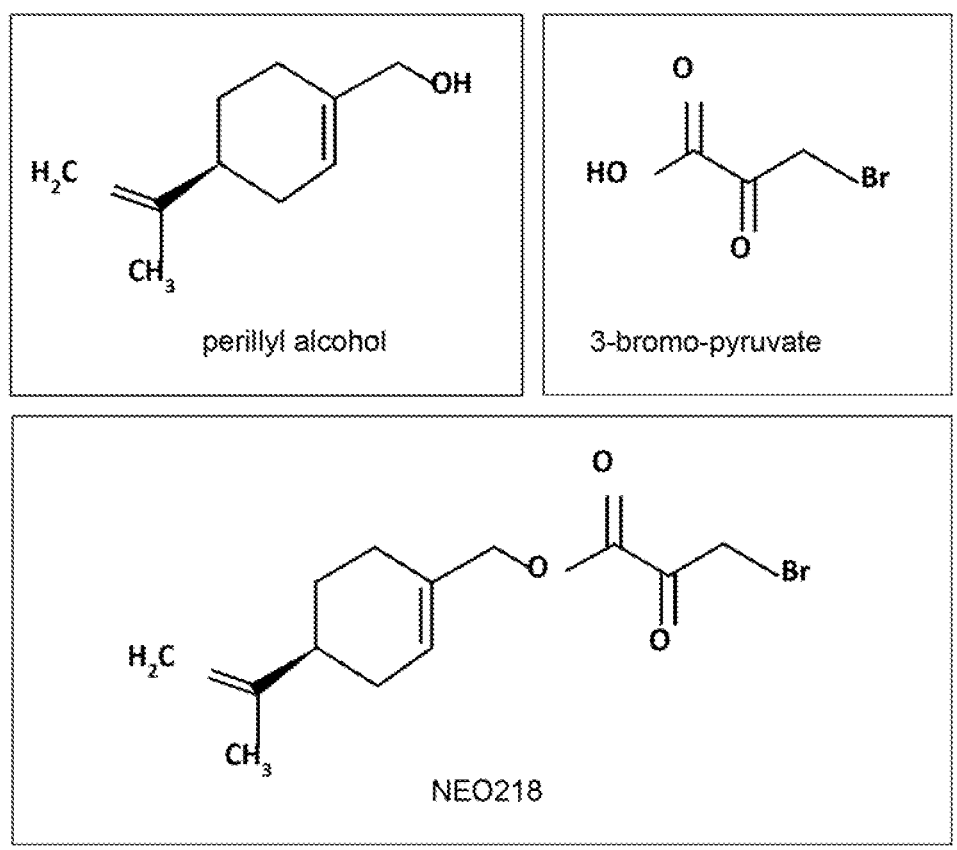
FIG. 1 displays the chemical structures of NEO218, perillyl alcohol (POH) and 3-bromo-pyruvate (3-BP). NEO218 is obtained by covalently conjugating POH to 3-BP.

A novel chemical entity has been synthesized by covalently linking two different molecules, 3-bromopyruvate (3-BP) and perillyl alcohol (POH). This compound is at times referred to herein as NEO218. FIG. 1 shows the chemical structure of NEO218.

The following abbreviations are used herein:
 c. 3-BP: 3-bromopyruvate;
 d. C7: caspase 7;
 e. Dox: doxorubicin;
 f. FACS: fluorescence-activated cell sorting;
 g. GAPDH: glyceraldehyde-3-phosphate dehydrogenase;
h. GSH: glutathione;
i. IC50: inhibitory concentration j. 50%; LDH: lactate dehydrogenase;
k. MCT1: monocarboxylate transporter 1;
l. MTT: 3-(4,5-dimethylthiazol-2-yl)-2,5-diphenyltetrazolium bromide;
m. NAC: N-acetyl-cysteine;
n. NEO218: 3-bromo-2-oxo-propionic acid 4-isopropenyl-cyclohex-1-enylmethyl ester;
o. PARP: poly (ADP-ribose) polymerase;
p. PI: propidium iodide;
q. POH: perillyl alcohol;
r. STS: staurosporine; and,
s. TMZ: temozolomide.

Example 1: Preparation POH-Bromopyruvate (3-Bromo-2-oxo-propionic acid 4-isopropenyl-cyclohex-1-enylmethyl ester)

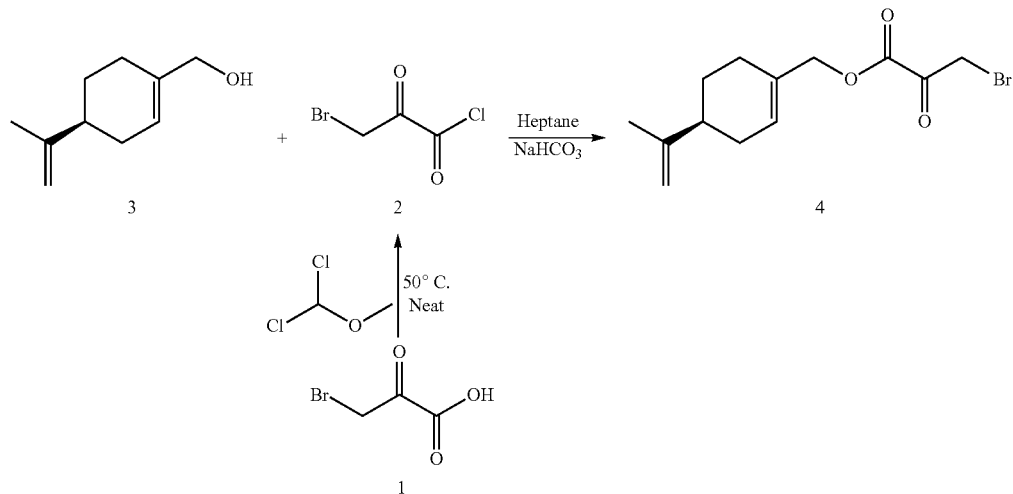

1,1-Dichlorodimethyl ether (2.5 g, 21.74 mmol) was added slowly to solid Bromopyruvic acid (1) while maintaining the temperature below 20° C. The resulting slurry was slowly heated to 50° C. and stirred for 2.5 h. The clear solution was cooled and the excess of dichlorodimethyl ether was concentrated under vacuum to obtain 3-bromopyruvic chloride (2) in greater than 95% yield.

3-Bromopyruvic chloride (2.0 g, 10.78 mmol) was added to a cold mixture of Perillyl alcohol (3) (1.5 g, 9.85 mmol), sodium bicarbonate (11.90 mmol), and n-heptane (180 mL) while maintaining the temperature below 10° C. The mixture was stirred for 20 min at 10° C. and then allowed to warm to RT. The reaction mixture was stirred for 18 h and quenched with water (75 mL). The organic layer was separated and washed with brine (75 mL) and dried over sodium sulfate. The filtered organic layer was concentrated under vacuum and purified by column chromatography [using Thomson single StEP 40 g column, Column dimensions: Dia 1.5 cm, Length: 30 cm] and eluted with hexanes. The similar fractions were combined and concentrated under vacuum to give 3-Bromo-2-oxo-propionic acid 4-isopropenyl-cyclohex-1-enylmethyl ester (4) as a pale yellow oil. Weight: 0.7 (24%). %, $^1$H-NMR (400 MHz, CDCl$_3$): δ 1.47 (m, 1H, 1.74 (s, 3H), 1.85 (m, 3H), 2.02 (m, 2H), 2.16 (m, 4H), 3.85 (s, 2H), 4.56 (s, 2H), 4.74 (d, 2H), 5.81 (br s, 1H).

Preclinical Studies

A series of preclinical in vitro and in vivo experiments was conducted to characterize and firmly establish the potent anticancer activity of NEO218. Representative results are provided below.

In Vitro Tumor Cell Evaluations

The tumor cell-killing potency of NEO218 was characterized by in vitro, short-term MTT assays (measuring viability of cells via determination of metabolic activity), LDH assays (measuring the release of lactate dehydrogenase as an indicator of leaky cell membranes, which are indicative of dying cells), and colony-formation assays (CFA, which determine long-term survival of drug-treated cells and their ability to spawn a colony of descendants). Several established cell lines derived from cancers of the breast were used as target cells (including MDA-MB-231; MDA-MB-468; T47D; MCF7; MCF7/Dox; BTB12), brain (T98G; U251), ovary (A2780), and colon (HCT116). In all cases, cells in culture were exposed to increasing concentrations of agents for 24 or 48 hours.

Figure 2:
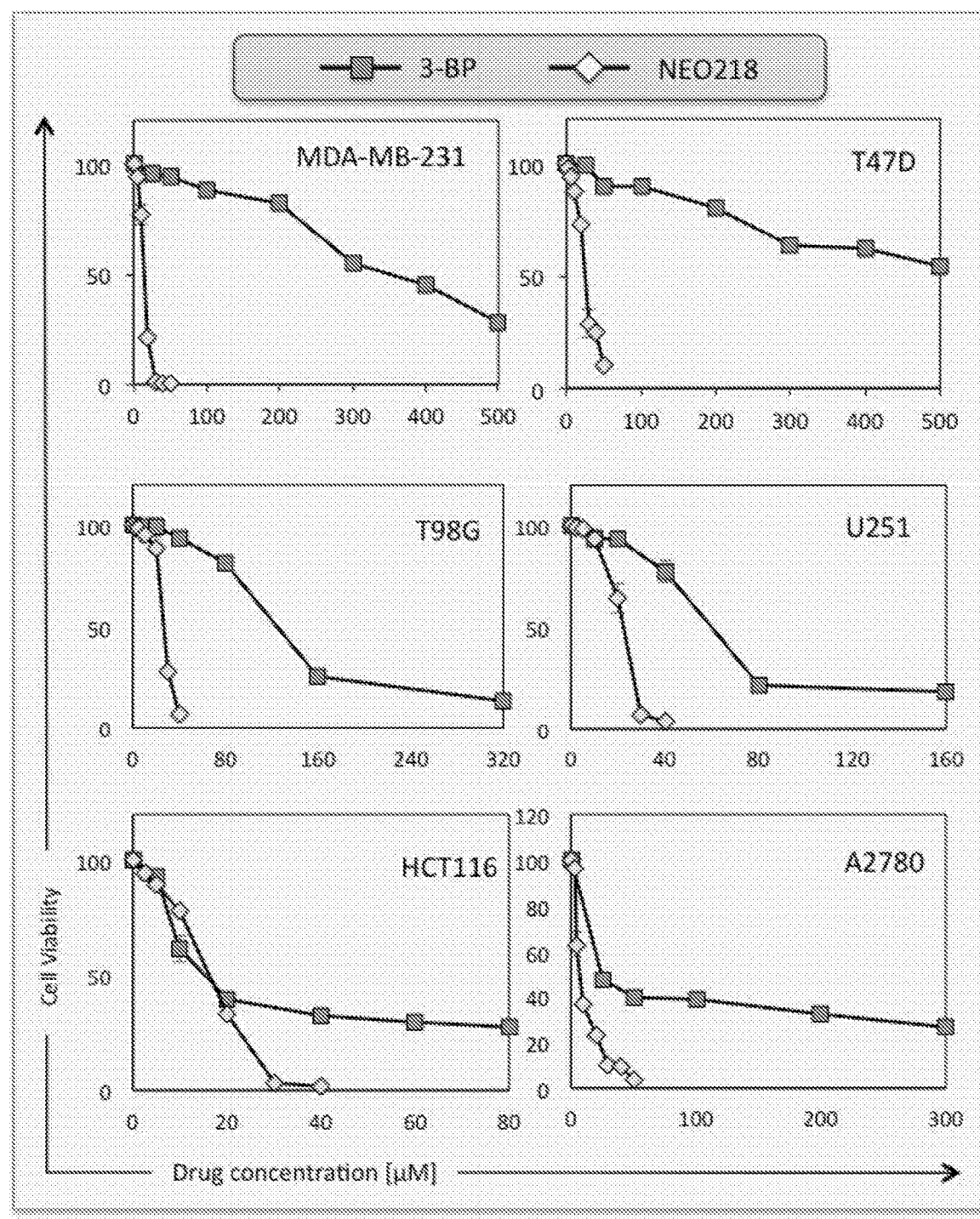
FIG. 2 displays plots of cell viability vs drug concentration resulting from the MTT assay in each of six different cell lines for NEO218 and 3-BP.

Cell lines from different cancer types were treated with increasing concentrations of 3-bromopyruvate (3-BP) or NEO218. After 48 hours, cell viability was measured by MTT assay. MDA-MB-231 and T47D are breast cancer cells; T98G and U251 are brain cancer (glioblastoma) cells; HCT116 are colon cancer cells; A2780 are ovarian cancer cells. FIG. 2 displays cell viability vs drug concentration plots for NEO218 and 3-BP in each of the six cell lines from the MTT assay.

As shown, NEO218 exerted more potent cancer cell killing effects than 3-BP in all cell lines, and its IC50 was in the range of 15-40 μM. In 4 of these cell lines, there was a very large differential between the cyotoxicity of NEO218 and 3-BP, whereas in 2 others there was only a small difference. FIG. 2 shows that NEO218 has greater anticancer effects than 3-BP.

Different tumor cell lines were treated with 3-BP mixed with POH, and the effects were compared to the effects of NEO218, as well as to 3-BP alone. The cells were treated for 24 hours, and then the MTT assay was conducted to measure cell viability.

Figure 3:
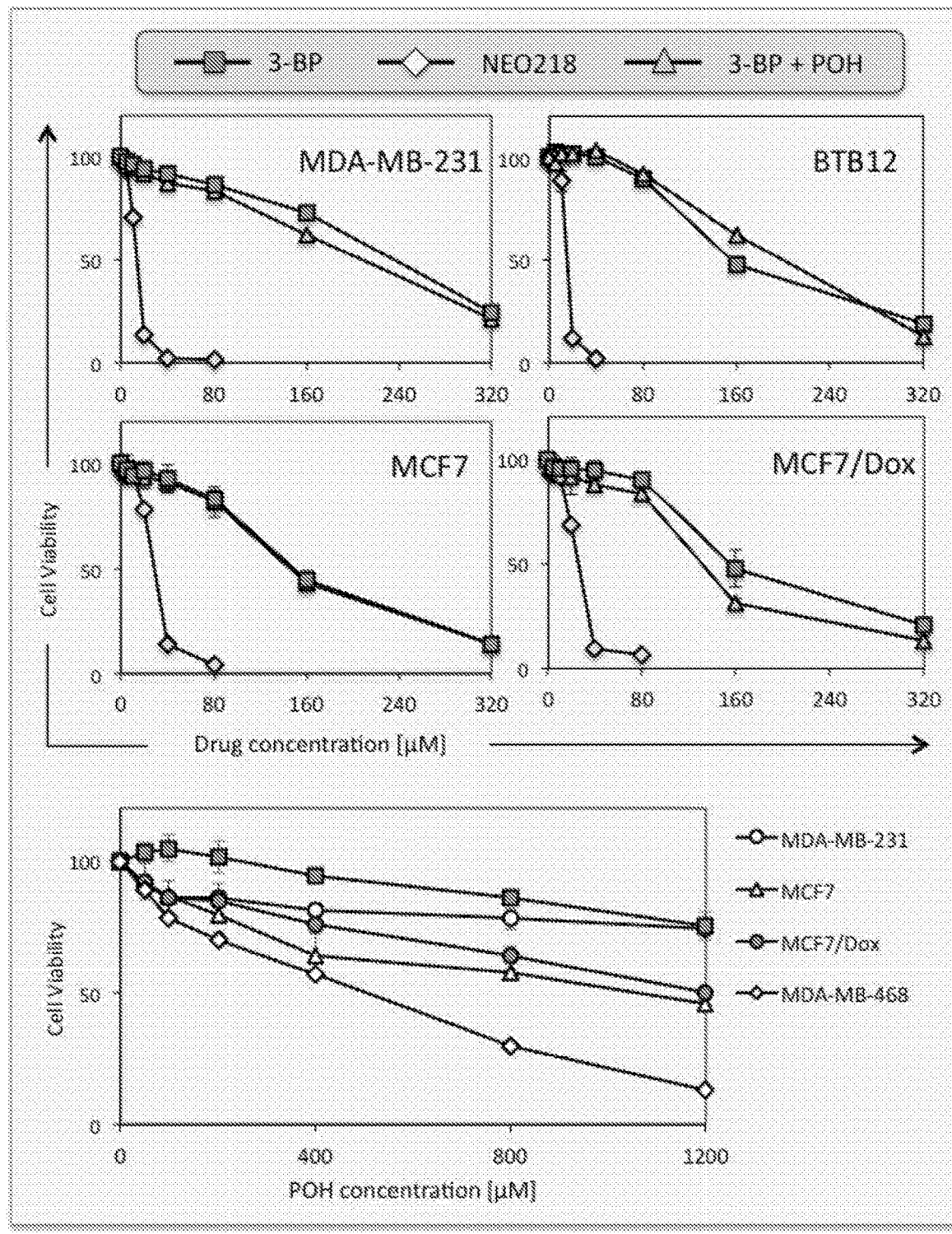
FIG. 3 displays plots of cell viability vs. drug concentration resulting from the MTT assay in each of four different cell lines for 3-BP, NEO218 and 3-BP+POH.

FIG. 3 displays plots of cell viability vs. drug concentration resulting from the MTT assay in each of four different cell lines for 3-BP, NEO218 and 3-BP+POH. In all cases, a mix of the two constituents did not achieve the much higher cytotoxic potency of NEO218. Rather, adding POH to 3-BP did not increase the toxicity over 3-BP alone. The bottom panel of FIG. 3 shows that POH alone did not exert strong cytotoxic potency, but required concentrations of 500 µM and above to reach IC50. Clearly, NEO218 was much more potent than any other treatment. These results provide further evidence for the surprising observation that the anticancer effects of NEO218 cannot be mimicked by mixing its individual components.

Figure 4:
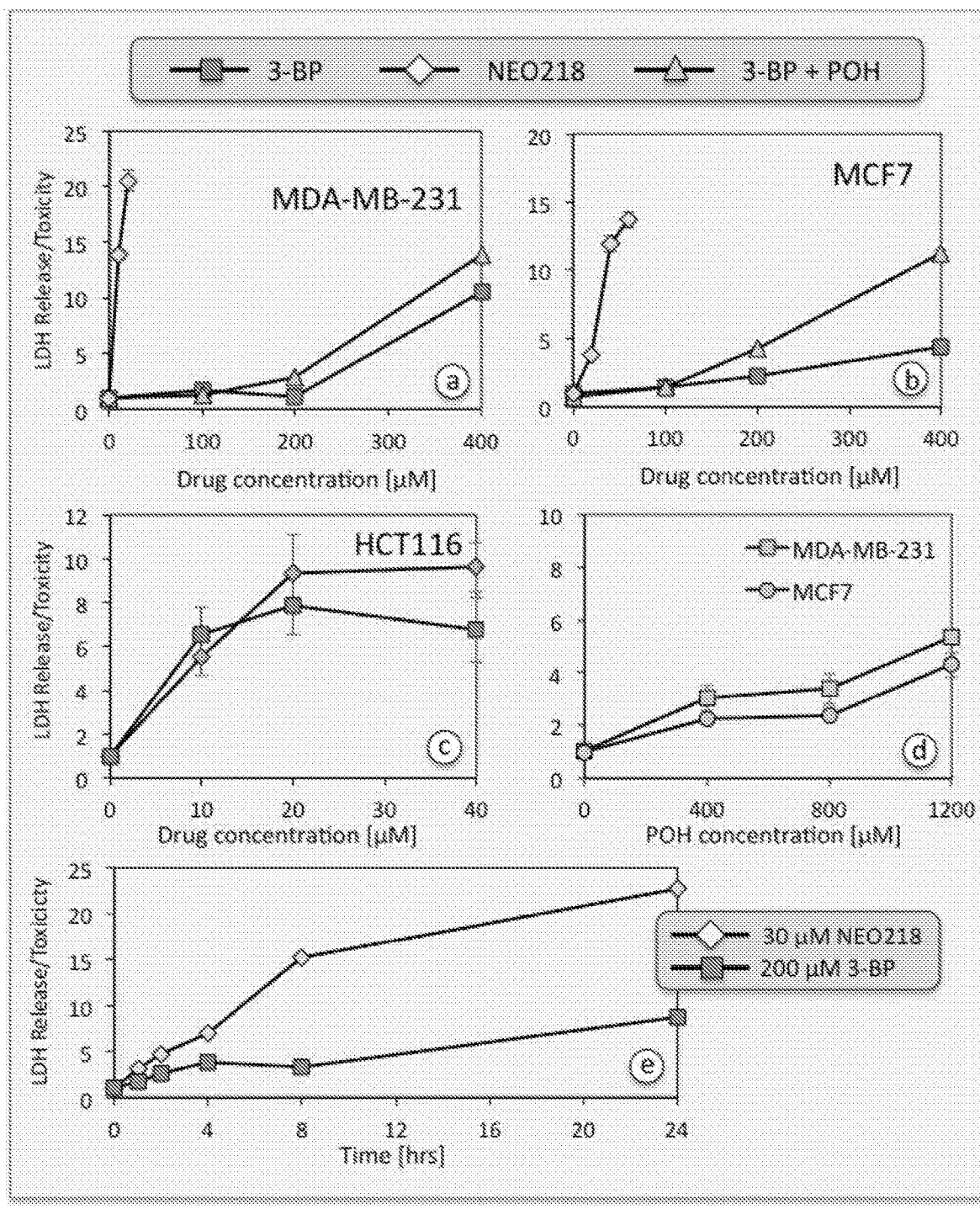
FIG. 4, Panels (a)-(d) display plots of LDH release/toxicity vs. drug concentration for each of 3-BP, NEO218 and 3-BP+POH, in each of three cell lines, and Panel (e) displays a plot of LDH release/toxicity vs. time for fixed concentrations of 3-BP and NEO218.

The capacity for rapid cell killing by NEO218 relative to 3-BP, POH and 3-BP+POH was evaluated via LDH assay, where LDH release is used as a proxy for cell death. FIG. 4, Panels (a-d) display plots of LDH release/toxicity vs. drug concentration for each of 3-BP, NEO218 and 3-BP+POH, in each of three cell lines, and Panel (e) displays a plot of LDH release/toxicity vs. time for fixed concentrations of 3-BP and NEO218.

In FIG. 4, Panels (a) and (b), show the results of treating breast cancer cell lines with increasing concentrations of NEO218, 3-BP, or 3-BP mixed with POH. Panel (c) shows the results of treating colon cancer cells with NEO218 or 3-BP. Panel (d) shows the results of treating two breast cancer cell lines with increasing concentrations of POH. In all cases a-d, the release of LDH (as a marker of cell death) was measured after 24 hours. Panel (e) shows a time course of LDH release in MDA-MB-231 breast cancer cells in response to treatment with NEO218 and 3-BP (individually).

A mix of 3-BP with POH does not reach the much greater toxic potency of NEO218, as shown in Panels (a-b). In HCT116 cells, NEO218 and 3-BP exert similar potency, as shown in Panel (c). POH by itself requires fairly high concentrations to achieve cell killing (i.e., LDH release), as shown in Panel (d). Cytotoxic effects of NEO218 can be detected as early as 1 hour after the onset of drug treatment, as shown in Panel (e), and half-maximal extent of cell death is reached before 8 hours.

The effect of NEO218 on tumor cell survival and colony formation relative to 3-BP, POH and 3-BP+POH was evaluated via the colony formation assay (CFA). Six hundred cells per culture well were seeded and exposed to increasing concentrations of NEO218, 3-BP, a mix of 3-BP+POH, or POH alone. After 24 hours, all drugs were removed from cells and fresh culture medium was added. Ten to fifteen days later, the surviving cells had formed colonies of descendants, which were stained and counted. All numbers were compared to the number of colonies formed in set-ups that did not receive any drug treatment (set at 100%).

Figure 5:
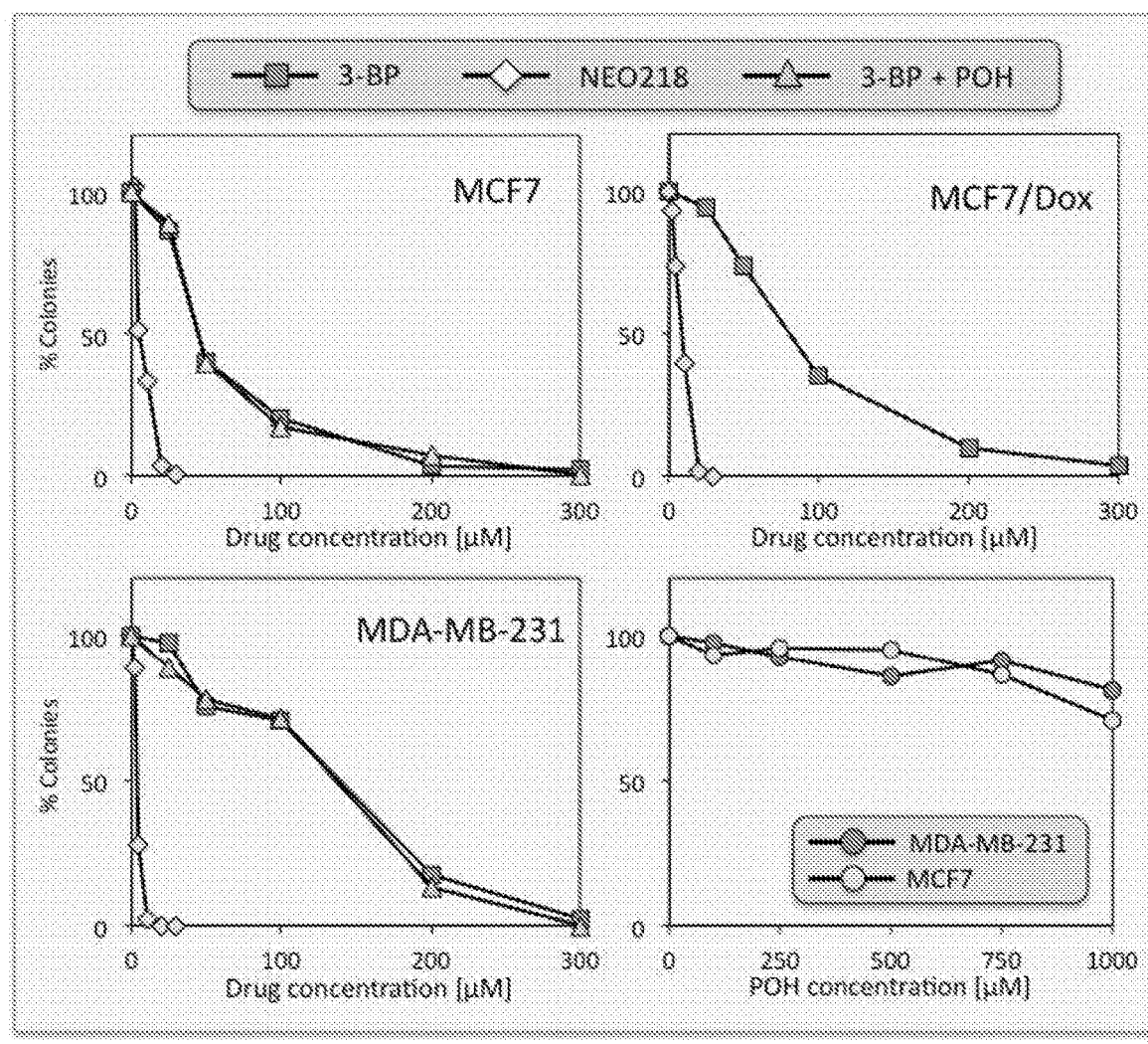
FIG. 5 displays plots of percent of colonies vs. drug concentration for each of 3-BP, NEO218 and 3-BP+POH, in each of two cell lines, that resulted from the colony formation assay (CFA).

FIG. 5 displays plots of percent of colonies vs. drug concentration for each of 3-BP, NEO218 and 3-BP+POH, in each of two cell lines, that resulted from the CFA. The data show that NEO218 strongly prevents cell survival and colony formation, with an IC50 of <10 µM. 3-BP is substantially less potent, and mixing 3-BP with POH does not increase the inhibitory effect over treatment with 3-BP alone. POH by itself was fairly ineffective and did not reach IC50 at concentrations of up to 1,000 µM, as show in the bottom right panel of FIG. 5.

In all experimental settings whose results are represented by FIGS. 2-5, treatment of cells with NEO218 resulted in greater toxicity than treatment with 3-BP. The IC50 (ability of a drug to reduce cell survival by 50%) of NEO218 was in the range of 5-30 µM in all cell types, whereas the IC50 of 3-BP was in the range of 10-200 µM. Of note, there were distinct cell type-specific differences, in that one group of cells revealed only a small difference in sensitivity to the two drugs, whereas the other group of cells showed a very large differential. For example, the IC50 of NEO218 and 3-BP was very similar in HCT116 cells, whereas all breast cancer cells were sensitive to NEO218, but resistant to 3-BP, as shown in FIGS. 2-5.

Individually, 3-BP and POH each possesses cytotoxic potency. However, the cytotoxic potency of NEO218 has surprisingly been found to be greater than the sum of the cytotoxic potencies of 3-BP and POH, as illustrated by FIGS. 3-5 show that this was not the case. POH alone has very low cytotoxic potential, with an IC50 of several hundred micromolar in all cells. The addition of POH to 3-BP, i.e., exposing cells to a mix of 3-BP plus POH, was unable to mimic the much greater potency of NEO218, demonstrating that cytotoxic potency of NEO218 is greater than the sum of its parts.

Included in the panels of tumor cells were two cell lines known to be resistant to conventional chemotherapeutic drugs. For instance, T98G glioblastoma cells are resistant to temozolomide (TMZ), the current standard of chemotherapeutic care for patients with malignant glioma [44]. MCF7/Dox breast cancer cells are resistant to doxorubicin and several other drugs; in fact, they display a multi-drug-resistant (mdr) phenotype [45]. Despite their drug-resistant phenotype, both cell types were effectively killed by NEO218, as shown in FIG. 2 for T98G cells, and FIGS. 3 and 5 for MCF7/Dox cells. Thus, NEO218 has been shown to effectively kill highly drug-resistant cancer cells.

In general, the major mechanisms of cell death are apoptosis and necrosis. An established marker of apoptotic cell death is the activation of caspases, which can be revealed via the conversion of pro-caspases to their cleaved (i.e., activated) fragments [46]. Further markers are the proteolytic cleavage of PARP (poly-(ADP-ribose) polymerase) [47] and the appearance of □-H2AX protein [48]. All these indicators of apoptosis can be detected by Western blot analysis.

The capacity for NEO218 to induce apoptosis was evaluated in a series of experiments. Three different cell lines were treated 3-BP and NEO218. Drug-treated cells were harvested, and cellular lysates were analyzed by Western blot for the presence of the three well-established markers of apoptosis:
  cleaved caspase 7 (cl. C7);
  cleaved (cl.) vs. full-length (f.l.) PARP; and,
  induction of γ-H2AX (which indicates DNA cleavage).
The appearance of cl. C7 and cl. PARP is indicative of ongoing apoptotic processes. In all cases, lysates were also probed for the presence of actin as a control.

Two breast cancer cell lines (MCF7 and MDA-MB-231) and one colon cancer cell line (HCT116) were treated with increasing concentrations of NEO218 or 3-BP. As a control, they were also treated with staurosporine (STS), a known potent inducer of apoptosis [49]. Western blot analyses for the presence of apoptosis markers are shown in the left panels of FIG. 6. Treatment with STS, hut not treatment with NEO218 or 3-BP, leads to the prominent appearance of apoptotic markers.

Figure 6:
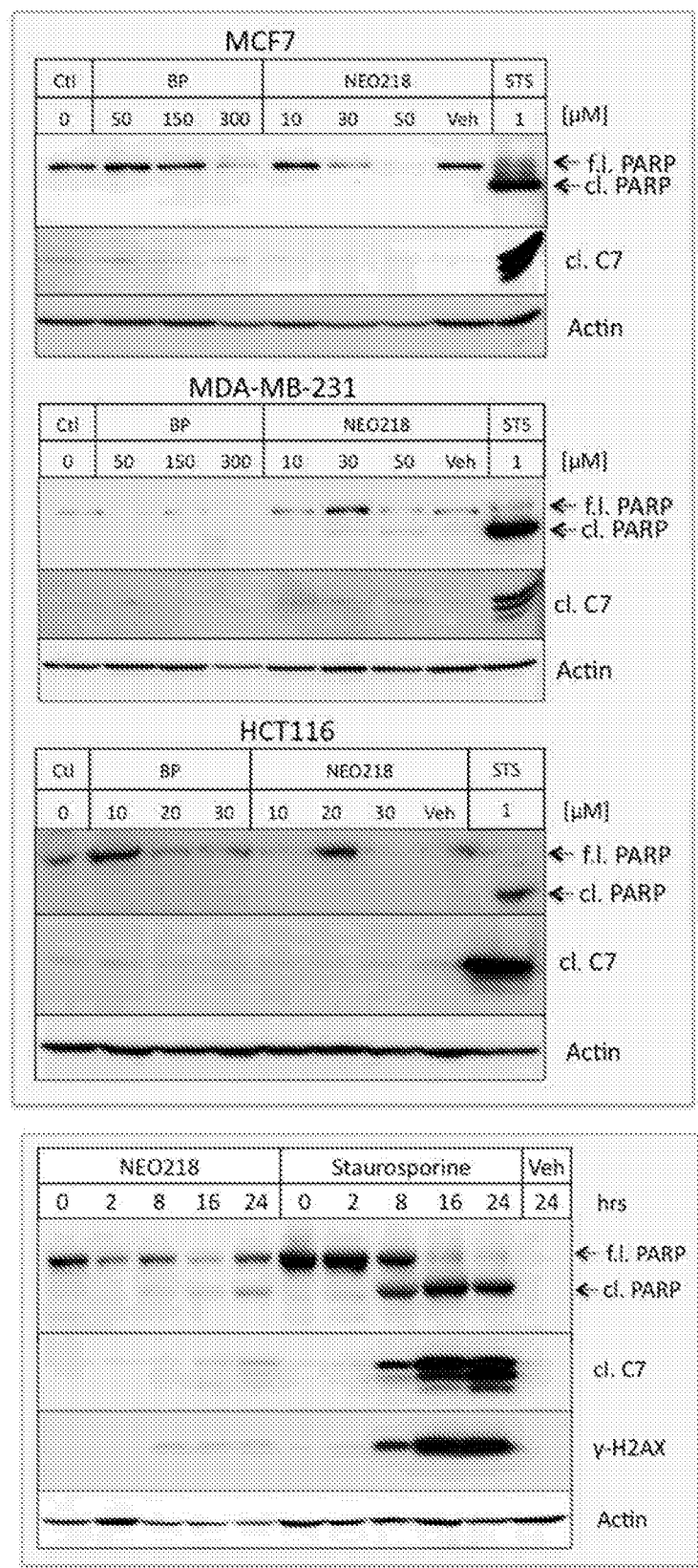
FIG. 6 displays the Western blot analyses for the presence of apoptosis markers in three cell lines treated with 3-BP and NEO218, the left panels on a concentration basis, and the right panel, on a time basis comparing the effects of treatments with staurosporine and NEO218.

The results of the time course of treatment of cell with staurosporine and NEO218 are displayed in the right panel of FIG. 6. Treatment of cells with staurosporine is shown to cause striking induction of all 3 markers of apoptosis (as would be expected from an agent that triggers apoptosis). In comparison, NEO218 barely affects these same markers, further confirming lack of biologically relevant apoptosis in NEO218-treated cells. Thus, it has been shown that NEO218 substantially avoids apoptosis.

The capacity for NEO218 to induce apoptosis was further evaluated in a series of experiments using an MTT assay. The apoptosis-blocker zVAD (z-VAD-FMK), an agent that acts as a pan-caspase inhibitor, was used. HCT116 colon cancer cells were treated for 1 hour with or without 50 µM zVAD, followed by increasing concentrations of NEO218 or 3-BP. Twenty-four hours thereafter, cell viability was determined by MTT assay.

Figure 7:
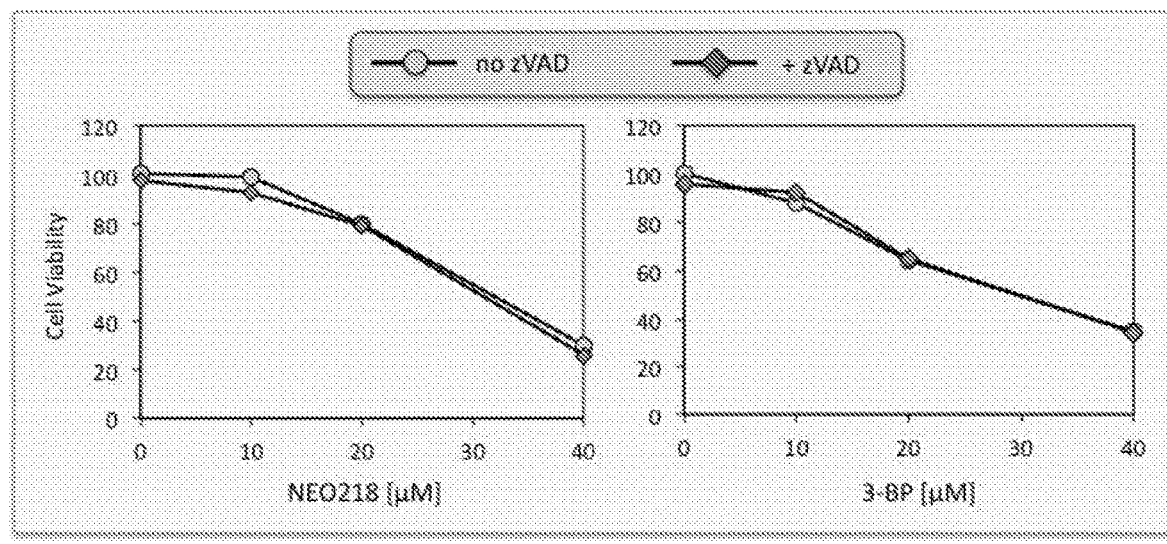
FIG. 7 displays plots of cell viability vs. drug concentration for both NEO218 and 3-BP, with and without zVAD.

FIG. 7 displays the results of the MTT assays as plots of cell viability vs. drug concentration for both NEO218 (left panel) and 3-BP (right panel), with and without zVAD. Pre-treatment of cells with zVAD did not prevent induction of cell death by NEO218 or 3-BP, indicating that cell death induced by these two agents did not involve typical apoptotic mechanisms, such as caspase activation, thus confirming the observation that NEO218 substantially avoids apoptosis.

In the absence of indications that apoptotic mechanisms played a significant role in cell death induced by NEO218, necrosis was investigated as a potential key mechanism. The distinction between apoptotic and necrotic cell death was made by measuring annexin V staining (a marker of apoptosis) and PI (propidium iodide) staining (a marker of necrosis) of drug-treated cells, in comparison to non-drug-treated cells (as a control). Measurements of annexin V and PI were done by FACS analysis after 2, 4, or 8 hours of treatment. Cells were treated with NEO218, 3-BP, and staurosporine (individually), and incorporation of propidium iodide (PI, a marker of necrotic cell death) or annexin V (a marker for apoptosis) was determined by fluorescence-activated cell sorting.

Figure 8:
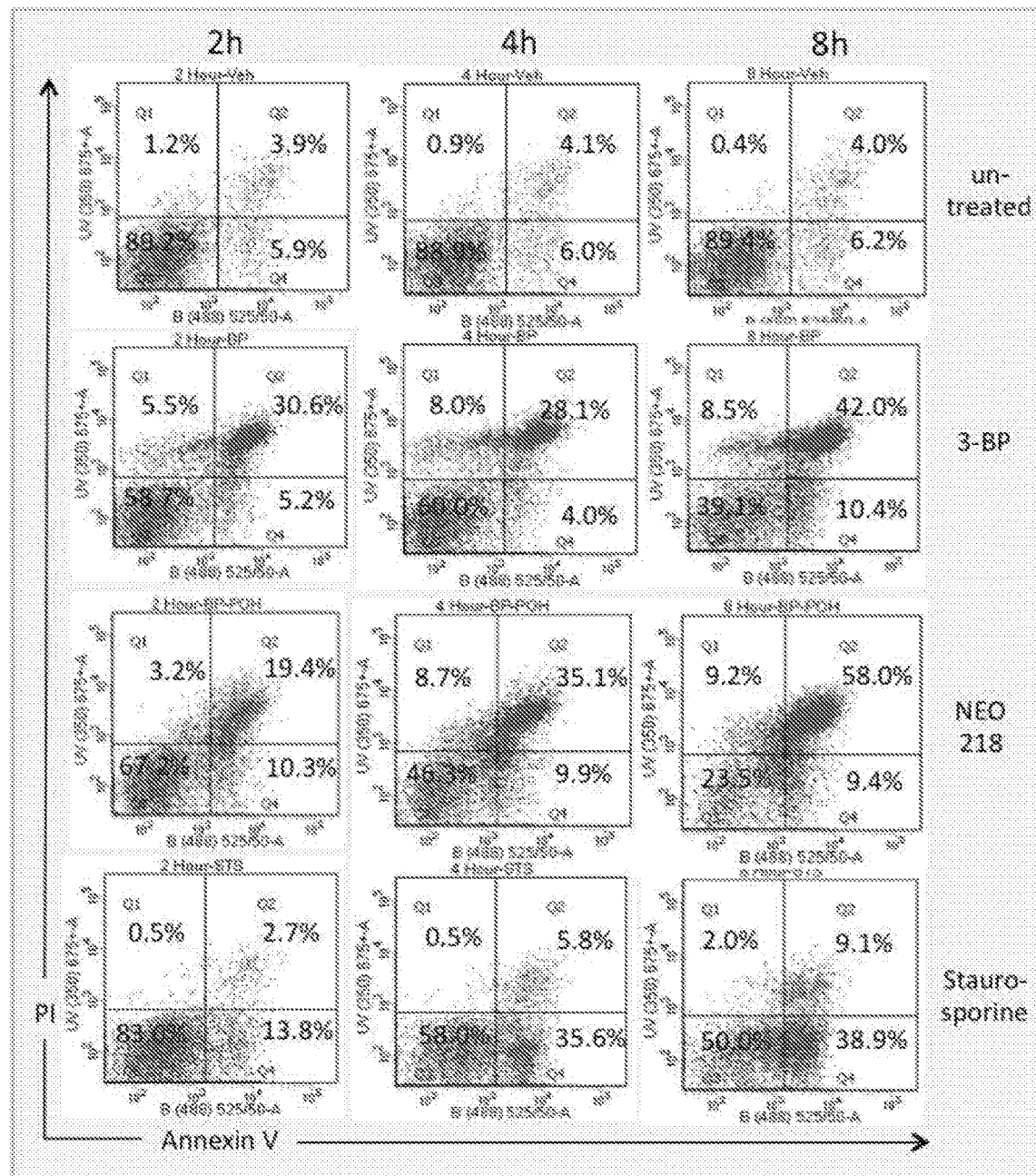
FIG. 8 shows a time-series of results of FACS analysis for annexin V and PI of untreated cells, and cells treated with 3-BP, NEO218 and staurosporine.

The results are organized in FIG. 8 as follows: no treatment (top row), 3-BP (second row), NEO218 (third row), and staurosporine (bottom row). Each individual square (consisting of 4 quadrants) shows percentage of live cells (bottom left quadrant), apoptotic cells (bottom right quadrant), and necrotic cells (top left and top right quadrants).

NEO218 (and 3-BP) caused vigorous incorporation of PI, but very little annexin V. Conversely, staurosporine treatment resulted in incorporation of annexin V, but very little PI. Untreated cells show about 90% viability. In NEO218-treated and 3-BP-treated cells, there is a major shift of cells into the upper quadrants, indicating necrosis as the primary type of cell death. In contrast, staurosporine (a known inducer of apoptosis) preferentially shifts cells to the bottom right, demonstrating prominent apoptosis as the primary type of drug-induced cell death. Thus, NEO218 causes cell death substantially by necrosis.

Taken together, these results demonstrate that necrosis, rather than apoptosis, is the main mechanism of cell death triggered by treatment with NEO218. This conclusion is further supported by observing the time course of cell death. As shown in FIG. 8, as well as the time course of LDH release in FIG. 4 (bottom panel), NEO218 initiates cell death fairly quickly, i.e., within 1-2 hours. Rapid cell death is a sign of necrosis, rather than apoptosis (which generally is a much slower, highly orchestrated process).

Having established that NEO218 causes necrotic cell death, the different primary events potentially responsible for this outcome were investigated. It is well established that lowering the levels of intracellular ATP pools below approximately 30% will result in necrotic cell death [53,54]. At these low ATP levels, cells are unable to maintain essential functions. As well, because apoptosis is a highly orchestrated "programmed" process that requires energy, these low ATP levels also prevent apoptosis, and the cells are forced to undergo necrosis instead. Thus, the effects of NEO218 on cellular energy levels, in particular the amount of ATP (adenosine triphosphate, the key unit of intracellular energy transfer) were investigated.

HCT116 colon cancer cells were treated cells with: NEO218, 3-BP; rotenone (a mitochondrial poison that blocks the respiratory chain); medium without glucose ("no gluc"; in order to shut down glycolysis); and, rotenone in combination with absent glucose (to cease all intracellular ATP production). After 3 hours of treatment, a commercially available ATP detection assay kit was employed to determine the relative levels of ATP present.

Figure 9:
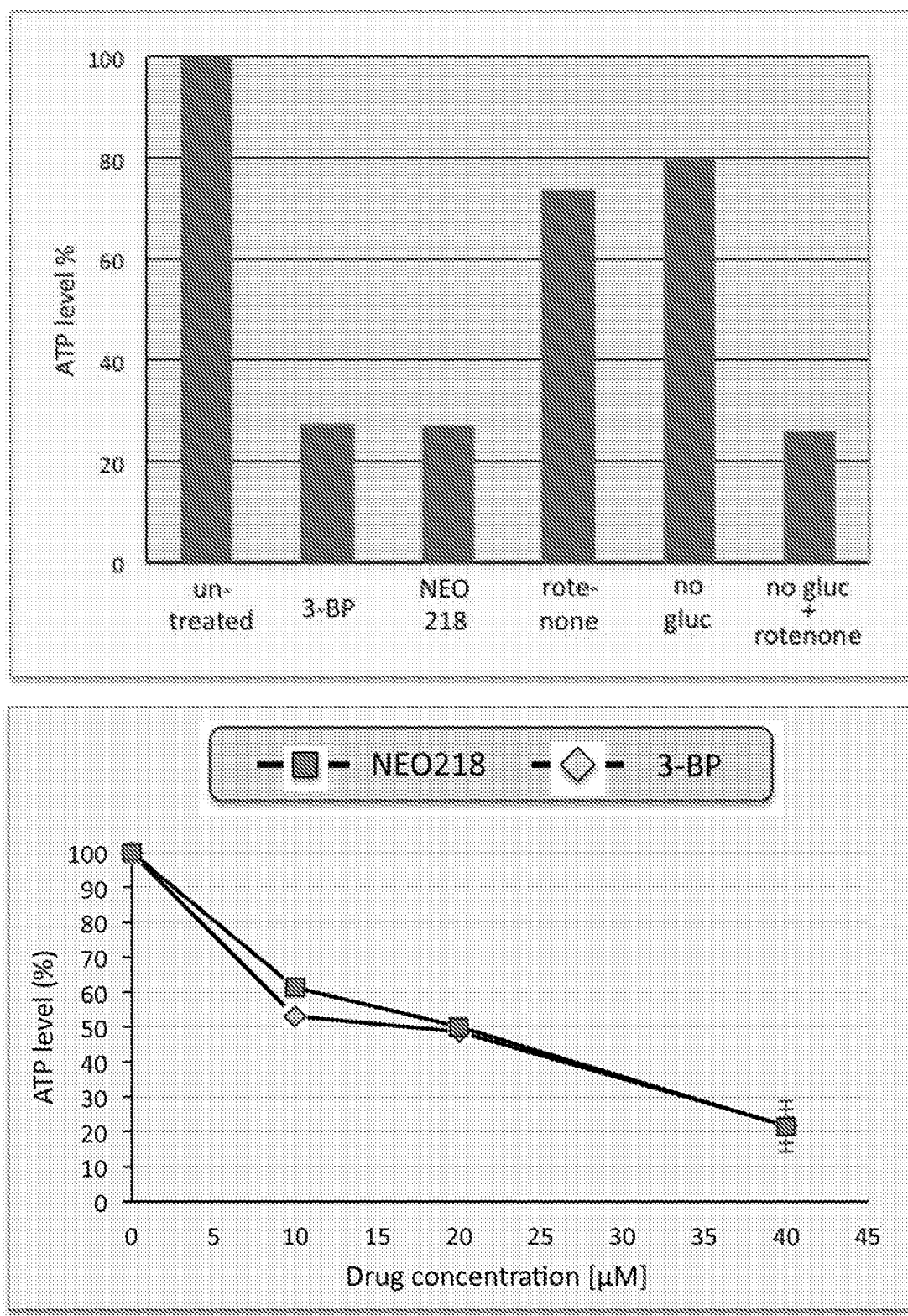
FIG. 9, left panel is a histogram of percent ATP content in colon cancer cells after 3 hours of treatment; right panel is a plot of % ATP vs. drug concentration for NEO218 and 3-BP.

The results are displayed in FIG. 9. The left panel displays a histogram of percent ATP content that results from each treatment course relative to that of the untreated cells. The right panel is a plot of % ATP vs. drug concentration for NEO218 and 3-BP.

FIG. 9 shows that treatment with either NEO218 or 3-BP potently depletes the levels of cellular ATP pools. This energy depletion was as efficient as the depletion achieved by treating the cells with rotenone in the absence of glucose. Rotenone is an inhibitor of mitochondrial respiration; the absence of glucose prevents glycolytic flux; as a result, the combination of rotenone with removal of glucose from the growth medium of cells will lead to the shut-down of the two central cellular energy-producing pathways, glycolysis and respiration. As shown in FIG. 9, the reduction of ATP levels in response to treatment with NEO218 was similar to the effects caused by the shutdown of glycolysis in combination with inhibited respiration, presenting a benchmark for the powerful energy depletion caused by NEO218. In this context, it can be concluded that NEO218 induces necrotic cell death via the efficient depletion of cellular energy.

Cellular stress conditions, in particular oxidative stress, is a known trigger for tumor cell death. To investigate this aspect, two potent and-oxidants, NAC (N-acetyl-cysteine) and GSH (glutathione), were used to determine whether they could minimize NEO218-induced cell death. NAC is the N-acetyl derivative of the amino acid cysteine; it is a medication used to treat acetaminophen overdose [50]. GSH is a tripeptide that is produced by all cells [51]. Both compounds sequester free radicals, thereby preventing damage to important cellular components [52].

Tumor cells were treated with either NAC or GSH, in combination with NEO218 or 3-BP. HCT116 cells were treated with increasing concentrations of NEO218 and 3-BP (individually), in the presence or absence of 5 mM NAC or 1 mM GSH. After 24 hours, cell viability was determined by MTT assay.

FIG. 10 displays plots of cell viability vs. drug concentration for NEO218 and 3-BP, with and without NAC and GSH. The data show that both anti-oxidants powerfully prevented cell death induced by NEO218 or 3-BP. In fact, in the presence of either of these two radical scavengers, drug-induced cell death was completely prevented. These results are in agreement with a hypothesis that NEO218 (and 3-BP) cause cell death via the generation of free radicals.

3-BP is known to inhibit the enzymatic activity of GAPDH (glyceraldehyde-3-phosphate dehydrogenase), resulting in the inhibition of glycolytic flux. Pyruvate (pyruvic acid) is a key intermediate in several metabolic pathways and represents the end product of the glycolytic pathway. Consequently, the addition of pyruvate was hypothesized to rescue this effect and ensure cell viability in the presence of 3-BP.

To test this hypothesis, HCT116 cells were treated with increasing concentrations of NEO218 and 3-BP (individually) in the presence or absence of 10 mM pyruvate. Viability of cells was determined 24 hours later by MTT cell viability assay.

Figure 11:
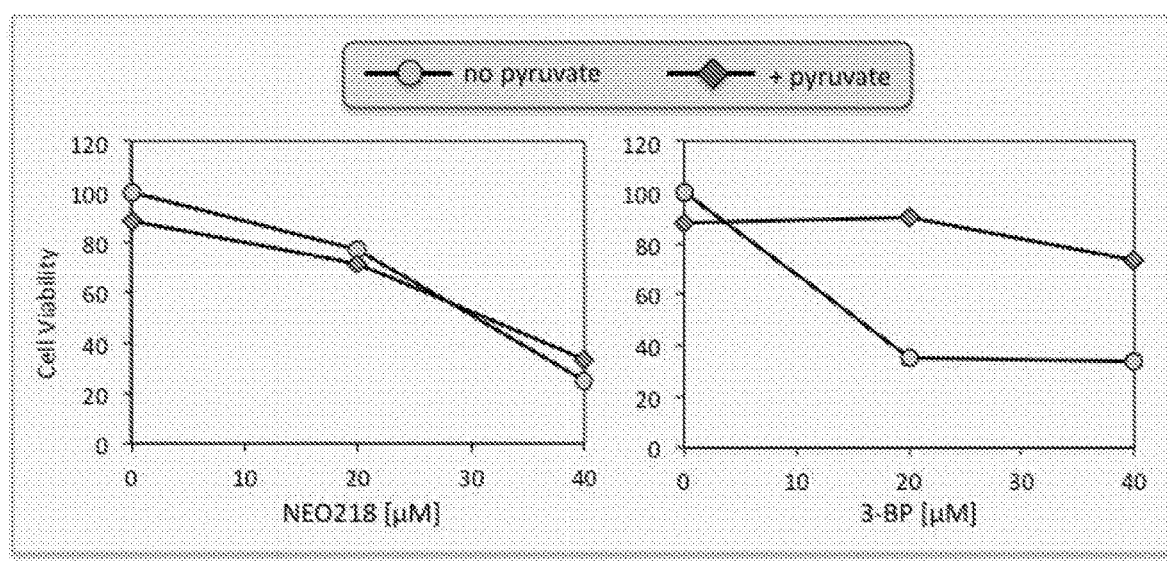
FIG. 11 displays plots of cell viability vs. drug concentration for NEO218 and 3-BP, with and without pyruvate.

FIG. 11 displays plots of cell viability vs. drug concentration for NEO218 and 3-BP, with and without pyruvate. In the case of 3-BP, as expected, excess pyruvate was able to completely prevent cell death. However, in the case of NEO218, pyruvate had no effect on viability at all, i.e., this metabolic product was unable to rescue NEO218-treated cells. The data show that NEO218 substantially inhibits GAPDH function.

The capacity of NEO218 to inhibit the enzymatic function of GAPDH in a cell-free system was investigated. Cell lysates were incubated with NEO218 and 3-BP (individually) for 1 hour, and enzymatic activity of GAPDH (glyceraldehyde-3-phosphate dehydrogenase) was determined. Increasing concentrations of NEO218 and 3-BP were applied. Separately, 50 µM NEO218 and 3-BP, respectively, were applied together with 1 mM NAC or GSH. The enzymatic activity of GAPDH was determined with the use of a commercially available GAPDH activity assay kit.

FIG. 12, top panel, displays a plot of GAPDH activity vs. drug concentration for NEO218 and 3-BP; the lower panels display histograms of GAPDH activity for NEO218 and 3-BP with NAC, with GSH, and without either. Both NEO218 and 3-BP caused potent inhibition of GAPDH enzyme activity (top panel), but the addition of anti-oxidants NAC or GSH effectively prevented the drug-induced inhibition of GAPDH activity (bottom panel). The protective effects of NAC and GSH were highly significant (asterisks: p-value<0.01). The data show that NEO218 substantially inhibits GAPDH enzymatic activity. NEO218 (and 3-BP) inhibited GAPDH with an IC50 that is similar to the IC50 that is effective at causing cell death. The addition of NAC or GSH effectively prevented GAPDH inhibition by NEO218 or 3-BP, which was interesting because the cell-free system used for these measurements should be unable to generate free radicals. Therefore, it may be the case that NAC and GSH exerted their protective effect by a mechanism other than squelching damaging radicals.

Then, the protein was subjected to analytical mass spectrometry. Analysis of the readout revealed two cysteine residues (at positions 245 and 282; indicated by ovals) that were modified by pyruvylation. Two other cysteine residues (at positions 150 and 154; indicated by rectangles) were not modified.

Thirty microgram of purified GAPDH protein was incubated in vitro with 60 µM 3-BP for 15 minutes at 37° C. Mass spectrometrical analysis was then used to determine whether 3-BP could directly bind to the amino acid sequence of the enzyme.

FIG. 13 displays the amino sequence (in one letter code) of the GAPDH protein, marked to indicate the presence of cysteine residues. Two of the four cysteines contained in GAPDH were found to have been modified. Cysteines at amino acid positions 245 and 282 turned out to be pyruvylated. It is likely that NEO218 can achieve the same outcome, and therefore it is concluded that GAPDH represents a primary target for alkylation by NEO218 and represents at least part of the mechanism by which NEO218 shuts down cellular energy production.

While some of the effects of NEO218 were similar to those of 3-BP, the major noted difference between these two agents was their cell death-inducing potency. While NEO218 killed all tumor cell types at low concentrations (IC50 between 5 and 30 µM), 3-BP displayed a distinct differential in that it was similarly potent in some cell types, but required substantially higher concentrations (>200 µM) in others.

3-BP is known to enter cells through one of the monocarboxylic acid transmembrane transporters (MCTs) [31, 55]. The expression levels of MCT1 in different tumor cell lines were determined by Western blot analysis and correlated with cytotoxic IC50 values in response of treatment of the same cells with NEO218 or 3-BP generated by MTT assay.

Figure 14:
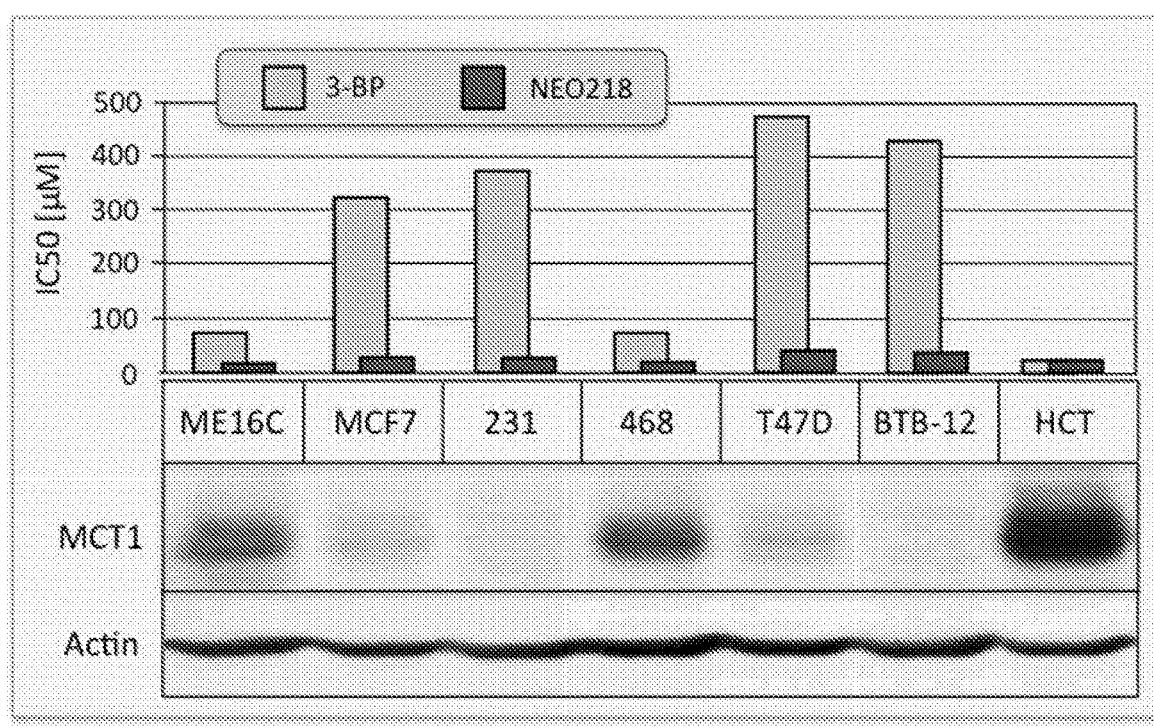
FIG. 14 displays cytotoxic IC50s for each of NEO218 and 3-BP in several cell lines, aligned over corresponding expression levels of MCT1 as shown in Western blots.

FIG. 14 displays cytotoxic IC50s for each of NEO218 and 3-BP in several cell lines, aligned over corresponding expression levels of MCT1 as shown in Western blots. The different tumor cells displayed greatly varying levels of MCT1 expression. Intriguingly, those cells with low MCT1 levels (MCF7, 231, T47D, BTB-12) were the ones resistant to 3-BP (i.e., IC50>300 µM), whereas those with high MCT1 levels (ME16C, 468, HCT116) were the ones sensitive to killing by 3-BP (IC50<100 µM). In comparison, all cells, irrespective of their MCT1 expression levels, were highly sensitive to NEO218 (IC50<35 µM).

Based on this alignment of MCT1 expression levels with cellular sensitivity to NEO218 and 3-BP, it is observed that—unlike 3-BP—NEO218 does not require active uptake by MCT1 in order to enter cells and unfold its cytotoxic potency. As a consequence, NEO218 is expected to display its anticancer activity in all tumor types, not just those that are positive for MCT1 expression.

The anticancer activity of NEO218 in vivo was investigated next. MDA-MB-231 triple-negative breast cancer cells were subcutaneously implanted into 12 nude mice. After two weeks, the animals were separated into 2 groups for treatment with either vehicle (no drug) or NEO218 (5 mg/kg). Then, NEO218 (or vehicle) was administered on days 1, 5, and 9 (3 doses total, 4 days apart). Tumor growth was measured with calipers every 3 days from day 1 (=start of treatment) until day 13 (end of experiment).

Figure 15:
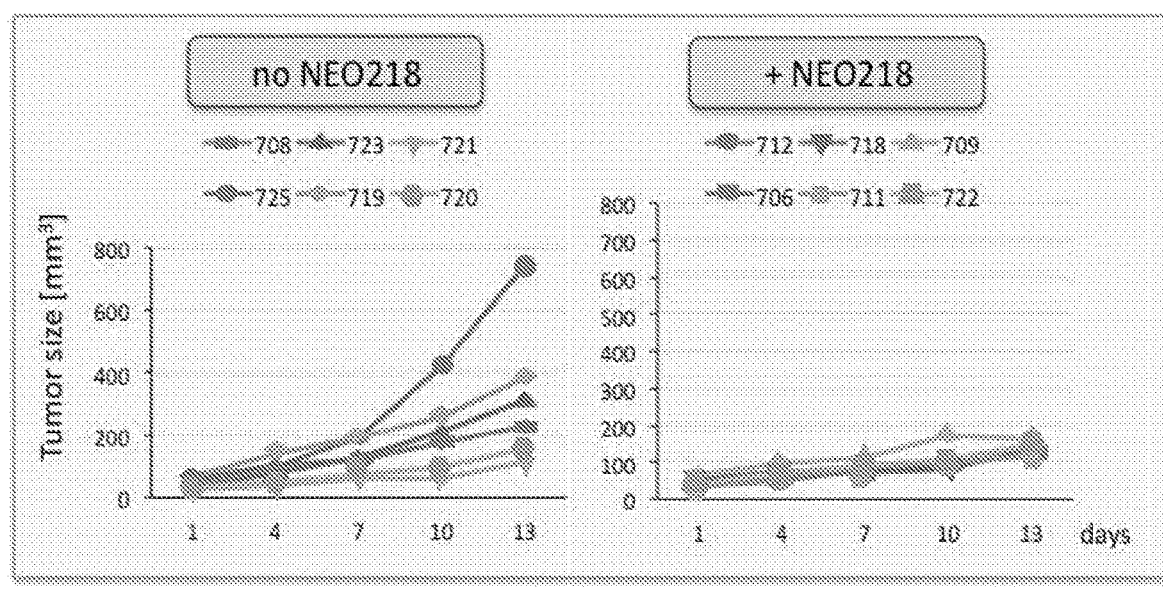
FIG. 15 displays plots of tumor size vs. time for each of NEO218 and 3-BP in a xenograft mouse model.

FIG. 15 displays plots of tumor size vs. time for each of NEO218 and 3-BP. The panels show tumor growth over time for each individual animal. The left panel shows tumor growth in the 6 mice that received vehicle; the right panel shows tumor growth in the 6 animals that were treated with NEO218.

As shown in FIG. 15, NEO218-treated animals did not display the prominently increased tumor growth that most of the vehicle-treated animals showed. In NEO218-treated mice, tumor volumes in all animals remained well below 200 cubic millimeters at the end of the experiment (day 13). In comparison, 4 out of the 6 vehicle-treated animals had tumor sized that were substantially greater than 200 cubic millimeters. NEO218 treatment resulted in slower tumor growth as compared to the group of animals that did not receive this compound. Although tumor growth was not prevented entirely, NEO218 exerted clear inhibitory effects, and it is conceivable that longer treatments with NEO218 will result in even stronger tumor inhibition. Mice treated with NEO218 tolerated this compound quite well, organ toxicity or other side effects were not detected in these animals.

NEO218 has revealed striking anticancer activity in several different tumor cell lines, including strongly drug-resistant variants, in vitro. As well, it revealed anticancer activity in a subcutaneous mouse tumor model.

In contrast to 3-BP, the anticancer activity of NEO218 is not dependent on the presence of the transmembrane transporter MCT1, but apparently is able to enter cells without a transport mechanism. As such, NEO218 is active against all tumor cell types, irrespective of the presence or absence of MCT1.

The dependence on MCI1 for 3-BP, but not for NEO218, explains several of the experimental results presented above. For instance, the ability of added pyruvate to rescue cells from the cytotoxic effects of 3-BP, but not from those of NEO218, can be explained by a simple competition effect. Pyruvate is a substrate for MCT1. Therefore, in the presence of excess pyruvate, MCT1 preferentially imports pyruvate and excludes 3-BP; as a result, 3-BP does not enter cells and the cells survive. In contrast, NEO218 does not require MCT1; therefore, despite the presence of excess pyruvate, it is still able to enter cells and exert cytotoxic effects.

Necrotic cell death caused by NEO218 is due to the depletion of cellular ATP pools, secondary to the inhibition of metabolic enzymes, such as GAPDH. Based on the alkylating properties of NEO218 (and 3-GP), it is quite likely that key metabolic enzymes other than GAPDH are pyruvylated and thereby inhibited as well. In the case of 3-BP, a number of other enzymes have been recognized as specific targets, such as hexokinase II (HK-II) [20] and succinate dehydrogenase (SDH) [21]. It is therefore conceivable that NEO218 affects these same enzymes too, as well as additional unidentified ones. The resulting shut-down of glycolysis, in combination with inhibited mitochondrial respiration, effectively depletes cellular ATP and forces cells into necrosis.

Although two anti-oxidants, NAC and GSH, were shown to shield cells from cell death during treatment with NEO218, it is unlikely that cell death triggered by NEO218 involves or requires free radical production in a significant manner. Rather, based on electrophilic and nucleophilic interactions, it is more likely that NAC and GSH directly bind to NEO218 and 3-BP, resulting in NAC-NEO218 and GSH-NEO218 complexes that are entirely inactive. In essence, NAC (or GSH) and NEO218 (or 3-BP) directly neutralize each other. This model is supported by the observation that NAC or GSH can also prevent inactivation of GAPDH by NEO218 when a cell-free system is used, indicating that protection by NAC and GSH is also afforded in an environment that is unable to produce significant amounts of free radicals. Furthermore, the ability of GSH to form a conjugate with 3-BP has recently been verified experimentally [56].

The mechanism of NEO218's anticancer function can be summarized as follows. NEO218 enters tumor cells directly, without the need for specific uptake mechanisms. Based on its nucleophilic characteristics, it pyruvylates key cysteine residues in a number of intracellular proteins, leading to the inactivation of key metabolic enzymes and the shut-down of cellular energy production. The resulting depletion of ATP pools forces cells into necrotic cell death. Altogether, these mechanisms are expected to preferentially unfold in cancer cells, due to their greater dependence on glycolysis (Warburg effect) and overall energy demands, thereby offering a therapeutic window or treatment with NEO218.

7. REFERENCES

[1] P. L. Crowell, C. E. Elson, Isoprenoids, Health Disease, in: R. E. C. Wildman, (Ed.), Neutraceuticals and Functional Foods CRC Press, Boca Raton, Fla., 2001.

[2] T. C. Chen, C. O. Fonseca, A. H, Schönthal, Preclinical development and clinical use of perillyl alcohol for chemoprevention and cancer therapy. Am J Cancer Res 5 (2015) 1580-1593.

[3] C. O. da Fonseca, R. Linden, D. Futuro, C. R. Gattass, T. Quirico-Santos, Ras pathway activation in gliomas: a strategic target for intranasal administration of perillyl alcohol. Arch Immunol Ther Exp (Warsz) 56 (2008) 267-276.

[4] T. Sundin, D. M. Peffley, D. Gauthier, P. Hentosh, The isoprenoid perillyl alcohol inhibits telomerase activity in prostate cancer cells. Biochimie 94 (2012) 2639-2648.

[5] T. Sundin, D. Peffley, P. Hentosh, eIF4E-Overexpression imparts perillyl alcohol and rapamycin-mediated regulation of telomerase reverse transcriptase. Exp Cell Res 319 (2013) 2103-2112.

[6] T. Sundin, D. M. Peffley, P. Hentosh, Disruption of an hTERT-mTOR-RAPTOR protein complex by a phytochemical perillyl alcohol and rapamycin. Mol Cell Biochem 375 (2013) 97-104.

[7] D. G. Garcia, L. M. Amorim, M. V. de Castro Faria, A. S. Freire, R. E. Santelli, C. O. Da Fonseca, T. Quirico-Santos, P. Burth, The anticancer drug perillyl alcohol is a Na/K-ATPase inhibitor. Mol Cell Biochem 345 (2010) 29-34.

[8] H. Y. Cho, W. Wang, N. Jhaveri, S. Torres, J. Tseng, M. N. Leong, D. J. Lee, A. Goldkom, T. Xu, N. A. Petasis, S. G. Louie, A. H. Schönthal, F. M. Hofman, T. C. Chen, Perillyl alcohol for the treatment of temozolomide-resistant gliomas. Mol Cancer Ther 11 (2012) 2462-2472.

[9] G. R. Hudes, C. E. Szarka, A. Adams, S. Ranganathan, R. A. McCauley, L. M. Weiner, C. J. Langer, S. Litwin, G. Yeslow, T. Halberr, M. Qian, J. M. Gallo, Phase I pharmacokinetic trial of perillyl alcohol (NSC 641066) in patients with refractory solid malignancies. Clin Cancer Res 6 (2000) 3071-3080.

[10] G. H Ripple, M. N. Gould, R. Z. Arzoomanian, D. Alberti, C. Feierabend, K. Simon, K. Binger, K. D. Tutsch, M. Pomplun, A. Wahamaki, R. Marnocha, G. Wilding, H. H. Bailey, Phase I clinical and pharmacokinetic study of perillyl alcohol administered four times a day. Clin Cancer Res 6 (2000) 390-396.

[11] J. R. Murren, G. Pizzorno, S. A. DiStasio, A. McKeon, K. Peccerillo, A. Gollerkari, W. McMurray, B. A. Burtness, T. Rutherford, X. Li, P. T. Ho, A. Sartorelli, Phase I study of perillyl alcohol in patients with refractory malignancies. Cancer Biol Ther 1 (2002) 130-135.

[12] G. Liu, K. Oettel, H. Bailey, L. V. Ummersen, K. Tutsch, M. J. Staab, D. Horvath, D. Alberti, R. Arzoomanian, H. Rezazadeh, J. McGovern, E. Robinson, D. DeMets, G. Wilding, Phase II trial of perillyl alcohol (NSC 641066) administered daily in patients with metastatic androgen independent prostate cancer. Invest New Drugs 21 (2003) 367-372.

[13] C. G. Azzoli, V. A. Miller, K. K. Ng, L. M. Krug, D. R. Spriggs, W. P. Tong, E. R. Riedel, M. G. Kris, A phase I trial of perillyl alcohol in patients with advanced solid tumors. Cancer Chemother Pharmacol 51 (2003) 493-498.

[14] C. O. da Fonseca, G. Schwartsmann, J. Fischer, J. Nagel, D. Futuro, T. Quirico-Santos, C. R. Gattass, Preliminary results from a phase I/II study of perillyl alcohol intranasal administration in adults with recurrent malignant gliomas. Surg Neurol 70 (2008) 259-266.

[15] C. O. da Fonseca, M. Simao, I. R. Lins, R. O. Caetano, D. Futuro, T. Quirico-Santos, Efficacy of monoterpene perillyl alcohol upon survival rate of patients with recurrent glioblastoma. J Cancer Res Clin Oncol 137 (2011) 287-293.

[16] C. O. da Fonseca, R. M. Teixeira, J. C. Silva, D.E.S.D.G.F. J, O. C. Meirelles, J. A. Landeiro, T.

Quirico-Santos, Long-term outcome in patients with recurrent malignant glioma treated with Perillyl alcohol inhalation. Anticancer Res 33 (2013) 5625-5631.

[17] M. Glick, P. Biddle, J. Jantzi, S. Weaver, D. Schirch, The antitumor agent 3-bromopyruvate has a short half-life at physiological conditions. Biochem Biophys Res Commun 452 (2014) 170-173.

[18] M. A. Apfel, B. H. Ikeda, D. C. Speckhard, P. A. Frey, Escherichia coli pyruvate dehydrogenase complex. Thiamin pyrophosphate-dependent inactivation by 3-bromopyruvate. J Biol Chem 259 (1984) 2905-2909.

[19] T. Banas, B. Gontero, V. L. Drews, S. L. Johnson, F. Marcus, R. G. Kemp, Reactivity of the thiol groups of Escherichia coli phosphofructo-1-kinase. Biochim Biophys Acta 957 (1988) 178-184.

[20] S. P. Mathupala, Y. H. Ko, P. L. Pedersen, Hexokinase-2 bound to mitochondria: cancer's stygian link to the "Warburg Effect" and a pivotal target for effective therapy. Semin Cancer Biol 19 (2009) 17-24.

[21] A. P. Pereira da Silva, T. El-Bacha, N. Kyaw, R. S. dos Santos, W. S. da-Silva, F. C. Almeida, A. T. Da Poian, A. Galina, Inhibition of energy-producing pathways of HepG2 cells by 3-bromopyruvate. Biochem J 417 (2009) 717-726.

[22] S. Ganapathy-Kanniappan, J. F. Geschwind, R. Kunjithapatham, M. Buijs, J. A. Vossen, I. Tchernyshyov, R. N. Cole, L. H. Syed, P. P. Rao, S. Ota, M. Vali, Glyceraldehyde-3-phosphate dehydrogenase (GAPDH) is pyruvylated during 3-bromopyruvate mediated cancer cell death. Anticancer Res 29 (2009) 4909-4918.

[23] M. C. Shoshan, 3-Bromopyruvate: targets and outcomes. J Bioenerg Biomembr 44 (2012) 7-15.

[24] S. Cardaci, E. Desideri, M. R. Ciriolo, Targeting aerobic glycolysis: 3-bromopyruvate as a promising anticancer drug. J Bioenerg Biomembr 44 (2012) 17-29.

[25] S. M. El Sayed, W. G. Mohamed, M. A. Seddik, A. S. Ahmed, A. G. Mahmoud, W. H. Amer, M. M. Helmy Nabo, A. R. Hamed, N. S. Ahmed, A. A. Abd-Allah, Safety and outcome of treatment of metastatic melanoma using 3-bromopyruvate: a concise literature review and case study. Chin J Cancer 33 (2014) 356-364.

[26] S. Ganapathy-Kanniappan, R. Kunjithapatham, J. F. Geschwind, Anticancer efficacy of the metabolic blocker 3-bromopyruvate: specific molecular targeting. Anticancer Res 33 (2013) 13-20.

[27] E. G. Konstantukou, G. E. Vontsinas, A. D. Velentzas, A. S. Basogianni, E. Paronis, E. Balafas, N. Kostomitsopoulos, K. N. Syrigos, E. Anastasiadou, D. J. Stravopodis, 3-BrPA eliminates human bladder cancer cells with highly oncogenic signatures via engagement of specific death programs and perturbation of multiple signaling and metabolic determinants. Mol Cancer 14 (2015) 135.

[28] A. P. Halestrap, Monocarboxylic acid transport. Compr Physiol 3 (2013) 1611-1643.

[29] P. Dell'Antone, Targets of 3-bromopyruvate, a new, energy depleting, anticancer agent. Med Chem 5 (2009) 491-496.

[30] F. Baltazar, C. Pinheiro, F. Morais-Santos, J. Azevedo-Silva, O. Queiros, A. Preto, M. Casal, Monocarboxylate transporters as targets and mediators in cancer therapy response. Histol Histopathol 29 (2014) 1511-1524.

[31] K. Birsoy, T. Wang, R. Possemato, O. H. Yilmaz, C. E. Koch, W. W. Chen, A. W. Hutchins, Y. Gultekin, T. R. Peterson, J. E. Carette, T. R. Brummelkamp, C. B. Clish, D. M. Sabatini, MCT1-mediated transport of a toxic molecule is an effective strategy for targeting glycolytic tumors. Nat Genet 45 (2013) 104-108.

[32] J. F. Geschwind, Y. H. Ko, M. S. Torbenson, C. Magee, P. L. Pedersen, Novel therapy for liver cancer: direct intraarterial injection of a potent inhibitor of ATP production. Cancer Res 62 (2002) 3909-3913.

[33] Y. H. Ko, B. L. Smith, Y. Wang, M. G. Pomper, D. A. Rini, M. S. Torbenson, J. Hullihen, P. L. Pedersen, Advanced cancers: eradication in all cases using 3-bromopyruvate therapy to deplete ATP. Biochem Biophys Res Commun 324 (2004) 269-275.

[34] W. Kim, J. H. Yoon, J. M. Jeong, G. J. Cheon, T. S. Lee, J. I. Yang, S. C. Park, H. S. Lee, Apoptosis-inducing antitumor efficacy of hexokinase II inhibitor in hepatocellular carcinoma. Mol Cancer Ther 6 (2007) 2554-2562.

[35] M. Buijs, J. A. Vossen, J. F. Geschwind, T. Ishimori, J. M. Engles, O. Acha-Ngwodo, R. L. Wahl, M. Vali, Specificity of the anti-glycolytic activity of 3-bromopyruvate confirmed by FDG uptake in a rat model of breast cancer. Invest New Drugs 27 (2009) 120-123.

[36] X. Cao, G. Jia, T. Zhang, M. Yang, B. Wang, P. A. Wassenaar, H. Chong, M. V. Knopp, D. Sun, Non-invasive MRI tumor imaging and synergistic anticancer effect of HSP90 inhibitor and glycolysis inhibitor in RIP1-Tag2 transgenic pancreatic tumor model. Cancer Chemother Pharmacol 62 (2008) 985-994.

[37] J. Yun, C. Rago, I. Cheong, R. Pagliarini, P. Angenendt, H. Rajagopalan, K. Schmidt, J. K. Wilson, S. Markowitz, S. Zhou, L. A. Diaz, Jr., V. E. Velculescu, C. Lengauer, K. W. Kinzler, B. Vogelstein, N. Papadopoulos, Glucose deprivation contributes to the development of KRAS pathway mutations in tumor cells. Science 325 (2009) 1555-1559.

[38] P. Icard, X. D. Zhang, E Lemoisson, M. H. Louis, S. Allouche, H. Lincet, L. Poulain, Experimental results using 3-bromopyruvate in mesothelioma: in vitro and in vivo studies. J Bioenerg Biomembr 44 (2012) 81-90.

[39] N. G. Schaefer, J. F. Geschwind, J. Engles, L. W. Buchanan, R. L. Wahl, Systemic administration of 3-bromopyruvate in treating disseminated aggressive lymphoma. Transl Res 159 (2012) 51-57.

[40] Q. Zhang, J. Pan, P. E. North, S. Yang, R. A. Lubet, Y. Wang, M. You, Aerosolized 3-bromopyruvate inhibits lung tumorigenesis without causing liver toxicity. Cancer Prev Res (Phila) 5 (2012) 717-725.

[41] J. Chapiro, S. Sur, L. J. Savic, S. Ganapathy-Kanniappan, J. Reyes, R. Duran, S. C. Thiruganasambandam, C. R. Moats, M. Lin, W. Luo, P. T. Tran, J. M. Herman, G. L. Semenza, A. J. Ewald, B. Vogelstein, J. F. Geschwind, Systemic delivery of microencapsulated 3-bromopyruvate for the therapy of pancreatic cancer. Clin Cancer Res 20 (2014) 6406-6417.

[42] R. T. Wicks, J. Azadi, A. Mangraviti, I. Zhang, L. Hwang, A. Joshi, H. Bow, M. Hutt-Cabezas, K. L. Martin, M. A. Rudek, M. Zhao, H. Brem, B. M. Tyler, Local delivery of cancer-cell glycolytic inhibitors in high-grade glioma. Neuro Oncol 17 (2015) 70-80.

[43] Y. H. Ko, H. A. Verhoeven, M. J. Lee, D. J. Corbin, T. J. Vogl, P. L. Pedersen, A translational study "case report" on the small molecule "energy blocker" 3-bromopyruvate (3BP) as a potent anticancer agent: from bench side to bedside. J Bioenerg Biomembr 44 (2012) 163-170.

[44] H. Huang, H. Lin, X. Zhang, J. Li, Resveratrol reverses temozolomide resistance by downregulation of MGMT in T98G glioblastoma cells by the NE-kappaB-dependent pathway. Oncol Rep 27 (2012) 2050-2056.

[45] B. Guo, D. J. Villeneuve, S. L. Hembruff, A. F. Kirwan, D. E. Blais, M. Bonin, A. M. Parissenti, Cross-resistance studies of isogenic drug-resistant breast tumor cell lines support recent clinical evidence suggesting that sensitivity to paclitaxel may be strongly compromised by prior doxorubicin exposure. Breast Cancer Res Treat 85 (2004) 31-51.

[46] J. B. Denault, G. S. Salvesen, Apoptotic caspase activation and activity. Methods Mol Biol 414 (2008) 191-220.

[47] D. W. Koh, T. M. Dawson, V. L. Dawson, Mediation of cell death by poly(ADP-ribose) polymerase-1. Pharmacol Res 52 (2005) 5-14.

[48] X. Huang, H. D. Halicka, F. Traganos, T. Tanaka, A. Kurose, Z. Darzynkiewicz, Cytometric assessment of DNA damage in relation to cell cycle phase and apoptosis. Cell Prolif 38 (2005) 223-243.

[49] R. Bertrand, E. Solary, P. O'Connor, K. W. Kohn, Y, Pommier, Induction of a common pathway of apoptosis by staurosporine. Exp Cell Res 211 (1994) 314-321.

[50] J. L. Green, K. J. Heard, K. M. Reynolds, D. Albert, Oral and Intravenous Acetylcysteine for Treatment of Acetaminophen Toxicity: A Systematic Review and Meta-analysis. West J Emerg Med 14 (201) 218-226.

[51] A. Pompella, A. Visvikis, A. Paolicchi, V. De Tata, A. F. Casini, The changing faces of glutathione, a cellular protagonist. Biochem Pharmacol 66 (2003) 1499-1503.

[52] N. van Zandwijk, N-acetylcysteine (NAC) and glutathione (GSH): antioxidant and chemopreventive properties, with special reference to lung cancer. J Cell Biochem Suppl 22 (1995) 24-32.

[53] Y. Eguchi, S. Shimizu, Y. Tsujimoto, Intracellular ATP levels determine cell death fate by apoptosis or necrosis. Cancer Res 57 (1997) 1835-1840.

[54] M. Leist, B. Single, A. F. Castoldi, S. Kuhnle, P. Nicotera, Intracellular adenosine triphosphate (ATP) concentration: a switch in the decision between apoptosis and necrosis. J Exp Med 185 (1997) 1481-1486.

[55] O. Queiros, A. Preto, A. Pacheco, C. Pinheiro, J. Azevedo-Silva, R. Moreira, M. Pedro, Y. H. Ko, P. L. Pedersen, F. Baltazar, M. Casal, Butyrate activates the monocarboxylate transporter MCT4 expression in breast cancer cells and enhances the antitumor activity of 3-bromopyruvate. J Bioenerg Biomembr 44 (2012) 141-153.

[56] I. Sadowska-Bartosz, R. Szewczyk, L. Jaremko, M. Jaremko, G. Bartosz, Anticancer agent 3-bromopyruvic acid forms a conjugate with glutathione. Pharmacol Rep 68 (2016) 502-505.

Purity

The purity of the NEO218 may be assayed by gas chromatography (GC) or high pressure liquid chromatography (HPLC). Other techniques for assaying the purity of NEO218 and for determining the presence of impurities include, but are not limited to, nuclear magnetic resonance (NMR) spectroscopy, mass spectrometry (MS), GC-MS, infrared spectroscopy (IR), and thin layer chromatography (TLC). Chiral purity can be assessed by chiral GC or measurement of optical rotation.

NEO218 may be purified by methods such as crystallization, or by separation from impurities according to its unique physicochemical properties (e.g., solubility or polarity). Accordingly, NEO218 can be separated from impurities by suitable separation techniques known in the art, such as preparative chromatography, (fractional) distillation, or (fractional) crystallization.

Methods of Treatment

The invention also provides for methods of using NEO218 to treat a disease, such as cancer or other nervous system disorders. NEO218 may be administered alone, or in combination with radiation, surgery or chemotherapeutic agents. NEO218 may also be co-administered with antiviral agents, anti-inflammatory agents or antibiotics. The agents may be administered concurrently or sequentially. NEO218 can be administered before, during or after the administration of the other active agent(s).

NEO218 may be used in combination with radiation therapy. In one embodiment, the present invention provides for a method of treating tumor cells, such as malignant glioma cells, with radiation, where the cells are treated with an effective amount of NEO218, and then exposed to radiation. NEO218 treatment may be before, during and/or after radiation. For example, NEO218 may be administered continuously beginning one week prior to the initiation of radiotherapy and continued for two weeks after the completion of radiotherapy. U.S. Pat. Nos. 5,587,402 and 5,602,184.

In one embodiment, the present invention provides for a method of treating tumor cells, such as malignant glioma cells, with chemotherapy, where the cells are treated with an effective amount of NEO218 and then exposed to chemotherapy. NEO218 treatment may be before, during and/or after chemotherapy.

NEO218 may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the NEO218 include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods of treating CNS disorders, including, without limitation, primary degenerative neurological disorders such as Alzheimer's, Parkinson's, psychological disorders, psychosis and depression. Treatment may consist of the use of NEO218 alone or in combination with current medications used in the treatment of Parkinson's, Alzheimer's, or psychological disorders.

The present invention also provides a method of improving immunomodulatory therapy responses comprising the steps of exposing cells to an effective amount of NEO218 before or during immunomodulatory treatment. Preferred immunomodulatory agents are cytokines, such interleukins, lymphokines, monokines, interfereons and chemokines.

The present composition may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, NEO218 may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see Remington's Pharmaceutical Sciences, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of NEO218 to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

This invention also provides the compositions as described above for intranasal administration. As such, the compositions can further comprise a permeation enhancer. Southall et al. Developments in Nasal Drug Delivery, 2000. NEO218 may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Wash.) can be used in this invention (http://www.kurvetech.com). NEO218 may also be delivered through a tube, a catheter, a syringe, a packtail, a pledget, a nasal tampon or by submucosal infusion. U.S. Patent Publication Nos. 20090326275, 20090291894, 20090281522 and 20090317377.

NEO218 can be formulated as aerosols using standard procedures. NEO218 may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of NEO218, as may be produced in any suitable device, such as an MDI, nebulizer, or a mist sprayer. Aerosol also includes a dry powder composition of the composition of the instant invention suspended in air or other carrier gas. Gonda (1990) Critical Reviews in Therapeutic Drug Carrier Systems 6:273-313. Raeburn et al., (1992) Pharmacol. Toxicol. Methods 27:143-159.

NEO218 may be delivered to the nasal cavity as a powder in a form such as microspheres delivered by a nasal insufflator. NEO218 may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing NEO218 can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10μ. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. NEO218 can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1μ and 100μ with micronized particles of NEO218 and dry blending. Alternatively, NEO218 can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as CCl.sub.3F. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

NEO218 may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

NEO218 may also be used alone or in combination with other chemotherapeutic agents via topical application for the treatment of localized cancers such as breast cancer or melanomas. NEO218 may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,401,841; 5,077,033; 4,882,150; and 4,738,851.

NEO218 can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The invention also provides a method for inhibiting the growth of a cell in vitro, ex vivo or in vivo, where a cell, such as a cancer cell, is contacted with an effective amount of NEO218 as described herein.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) Intern. J. Mol. Med. 10:785-788. Thorne, et al. (2004) Neuroscience 127:481-496. Fernandes, et al.

(2005) [10096] Oncology Reports 13:943-947. Da Fonseca, et al. (2008) Surgical Neurology 70:259267. Da Fonseca, et al. (2008) Arch. Immunol. Ther Exp. 56:267-276. Hashizume, et al. (2008) Neuroncology 10:112-120.

In vitro efficacy of the present composition can be determined using methods well known in the art. For example, the cytoxicity of NEO218 and/or the therapeutic agents may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. J. of Immunological Methods 65: 55 63, 1983. The cytoxicity of NEO218 and/or the therapeutic agents may be studied by colony formation assay. Functional assays for inhibition of VEGF secretion and IL-8 secretion may be performed via ELISA. Cell cycle block by NEO218 and/or the therapeutic agents may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

Example 2 A Perillyl Alcohol-Conjugated Analog of 3-Bromopyruvate Without Cellular Uptake Dependency on Monocarboxylate Transporter 1 and With Activity in 3-BP-Resistant Tumor Cells Abbreviations: 3-BP: 3-bromopyruvate; CFA: colony formation assay; GAPDH: glyceraldehyde 3-phosphate dehydrogenase; GSH: glutathione; MCT-1: monocarboxylate transporter 1; NAC: N-acetylcysteine; NEO218: perillyl alcohol conjugated to 3-bromopyruvate; POH: perillyl alcohol; ROS: reactive oxygen species; SDH: succinate dehydrogenase complex.

ABSTRACT

The anticancer agent 3-bromopyruvate (3-BP) is viewed as a glycolytic inhibitor that preferentially kills glycolytic cancer cells through energy depletion. However, its cytotoxic activity is dependent on cellular drug import through transmembrane monocarboxylate transporter 1 (MCT-1), which restricts its anticancer potential to MCT-1-positive tumor cells. We created and characterized an MCT-1-independent analog of 3-BP, called NEO218. NEO218 was synthesized by covalently conjugating 3-BP to perillyl alcohol (POH), a natural monoterpene. The responses of various tumor cell lines to treatment with either compound were characterized in the presence or absence of supplemental pyruvate or antioxidants N-acetyl-cysteine (NAC) and glutathione (GSH). Drug effects on glyceraldehyde 3-phosphate dehydrogenase (GAPDH) enzyme activity were investigated by mass spectrometric analysis. The development of 3-BP resistance was investigated in MCT-1-positive HCT116 colon carcinoma cells in vitro. Our results show that NEO218: (i) pyruvylated GAPDH on all 4 of its cysteine residues and shut down enzymatic activity; (ii) severely lowered cellular ATP content below life-sustaining levels, and (iii) triggered rapid necrosis. Intriguingly, supplemental antioxidants effectively prevented cytotoxic activity of NEO218 as well as 3-BP, but supplemental pyruvate powerfully protected cells only from 3-BP, not from NEO218. Unlike 3-BP, NEO218 exerted its potent cytotoxic activity irrespective of cellular MCT-1 status. Treatment of HCT116 cells with 3-BP resulted in prompt development of resistance, based on the emergence of MCT-1-negative cells. This was not the case with NEO218, and highly 3-BP-resistant cells remained exquisitely sensitive to NEO218. Thus, our study identifies a mechanism by which tumor cells develop rapid resistance to 3-BP, and presents NEO218 as a superior agent not subject to this cellular defense. Furthermore, our results offer alternative interpretations of previously published models on the role of supplemental antioxidants: Rather than quenching reactive oxygen species (ROS), supplemental NAC or GSH directly interact with 3-BP, thereby neutralizing the drug's cytotoxic potential before it can trigger ROS production. Altogether, our study introduces new aspects of the cytotoxic mechanism of 3-BP, and characterizes NEO218 as an analog able to overcome a key cellular defense mechanism towards this drug.

1. Introduction

3-Bromopyruvate (3-BP; 3-bromopyruvic acid) is a synthetic, halogenated derivative of pyruvate with cytotoxic activity. It functions as an alkylator of certain proteins, and ensuing protein pyruvylation generally results in the inhibition of enzymatic activity. The best-described target protein of 3-BP is glyceraldehyde-3-phosphate dehydrogenase (GAPDH) in the glycolytic pathway [1, 2], which contributed to the reputation of 3-BP as a glycolytic inhibitor [3-6]. Tumor cells depend on glycolysis to a greater extent than normal cells (Warburg effect), and cell death induced by 3-BP is thought to be due to depletion of cellular energy pools [3, 4, 7]. This view was further supported by experiments demonstrating that supplemental pyruvate could protect cells against the cytotoxic impact of 3-BP in cell culture [8, 9].

Cellular uptake of 3-BP requires the presence of monocarboxylate transporter 1 (MCT-1) [10], a member of a larger family of carboxylate transmembrane transporters [11]. MCT-1 is a proton-linked transport protein that is expressed in most tissues and exhibits broad, specificity for short-chain monocarboxylic acids. In glycolytic tumor cells, MCT-1 supports high glycolytic flux via the export of lactate, and preserves intracellular pH via co-transport of a proton [12]. Studies have indicated elevated expression of MCT-1 in various types of tumors, which was taken as an indication that tumor-specific uptake of 3-BP might be achievable in patients. However, there are also examples of tumors with down-regulated MCT-1 levels. Together with the general observation that MCT-1 is widely expressed in many healthy tissues, it has remained somewhat controversial whether tumor selectivity of 3-BP is easily achievable [12].

Several other phenotypic consequences of 3-BP have been described in vitro. Besides GAPDH, a number of other enzymes from bacteria to fungi to humans were shown to be inhibited by 3-BP, including succinate dehydrogenase (SDH; complex II) and hexokinase II [13-21], although the impact on the latter was not observed consistently [1, 22]. 3-BP was also reported to cause oxidative stress via depletion of intracellular glutathione and its impact on mitochondria, leading to increased levels of reactive oxygen species (ROS) [22-24]. More recently, additional pleiotropic effects of 3-BP, including stimulation of autophagy [25], induction of endoplasmic reticulum stress [26], and dysregulation of two key intracellular signal transduction pathways, the Akt/mTOR and the MAP kinase pathways, were reported [27]. In vivo, 3-BP has shown therapeutic potential in a number of animal tumor models [6, 28-30], although liver toxicity was noted [31]. As well, there are two case studies [32, 33] where 3-BP was administered to patients, and one of those [33] reported favorable responses in a patient with hepatocellular carcinoma. Of note, during the summer of 2016 several patients died within a few days after receiving 3-BP at a health clinic in Germany, and it is currently being investigated whether 3-BP played a role, if any, in this extremely unfortunate outcome [34].

Perillyl alcohol (POH) is a monoterpene and a natural constituent of caraway, lavender and lilac oil, cherries, cranberries, sage, spearmint, celery seeds, and certain other plants [35]. Although this compound had shown promising activity in several preclinical cancer models, it did not enter clinical practice, primarily because dose-limiting intestinal toxicity became evident in clinical trials [36]. However, recent phase I/II clinical studies in Brazil demonstrated that simple intranasal inhalation of POH was effective against recurrent glioblastoma, in the absence of detectable toxic events [37]. Based on POH's therapeutic potential, we hypothesized that covalently linking POH to 3-BP might yield a novel therapeutic compound with inherently increased anticancer activity that perhaps might also be applicable to 3-BP-resistant cancer cells. Here, we present results from our study, detailing the molecular and cellular characterization of the in vitro anticancer activity of this new 3-BP analog, termed NEO218, in comparison to 3-BP.

2. Materials and methods

2.1. Pharmacological Agents

3-BP was obtained from Sigma-Aldrich (St. Louis, Mo.) and dissolved in phosphate-buffered saline (PBS) to make a 200 mM stock solution. NEO218 was manufactured by Norac Pharma (Azusa Calif.) and was provided by NeOne Technologies, Inc. (NTI, Los Angeles, Calif.); it was dissolved in DMSO (Santa Cruz Biotechnology, Inc., Santa Cruz, Calif.) at 200 mM. Aliquots were stored at −20° C. for up to one month without freeze/thawing. Z-VAD-FMK (carbobenzoxy-valyl-alanyl-aspartyl-[O-methyl]-fluoromethylketone), a cell-permeant pan caspase inhibitor that irreversibly binds to the catalytic site of caspase proteases, was obtained from Sigma-Aldrich and used from a 20 mM stock solution prepared with DMSO. Sodium-pyruvate and methyl-pyruvate were obtained from Sigma-Aldrich as well. Methyl-pyruvate is thought to enter mitochondria more effectively, although in our experiments both forms of pyruvate were similarly effective.

2.2. Cell Lines and Culture

The following human tumor cell lines were used: HCT116 colon carcinoma; LN229, T98G, and U251 glioblastoma; MCF7, MDA-MB-231, MDA-MB-468, BTM-12, and T47D breast carcinoma. ME16C are normal mammary gland epithelium cells immortalized with telomerase. All cells were propagated in DMEM supplemented with 10% fetal bovine serum (FBS), 100 U/mL penicillin, and 0.1 mg/mL streptomycin in a humidified incubator at 37° C. and a 7% $CO_2$ atmosphere. All cell culture reagents were provided by the Cell Culture Core Lab of the USC/Norris Comprehensive Cancer Center and prepared with raw materials from Cellgro/MediaTech (Manassas, Va.); FBS was obtained from Omega Scientific (Tarzana, Calif.).

2.3. MTT Assay

Methylthiazoletetrazolium (MTT) assays were performed as described earlier [38]. Briefly, cells were seeded into 96-well plates at 2.0 to $8.0 \times 10^3$ cells per well and exposed to drug treatment (or solvent alone) for 24 or 48 hours. In individual experiments, each treatment condition was set up in triplicate, and each experiment was repeated several times independently.

2.4. Colony Formation Assay

Depending on the cell line (and plating efficiency), 250-800 cells were seeded into each well of a 6-well plate and treated as described in detail previously [39]. After 12-16 days, colonies (defined as groups of >50 cells) were visualized by staining for 4 hours with 1% methylene blue (in methanol), and then were-counted. Experiments were repeated at least once, but usually more often under different conditions.

2.5. LDH Assay

Depending on the cell line, 2000 to 4000 cells per well were seeded in a volume of 50 µL into a 96-well plate. The next day, drugs ere added in an additional 50 µL of medium. At different time points (usually after 24 hours of incubation), 50 µL medium was removed and processed with the LDH Cytotoxicity Assay Kit (Thermo Fisher Scientific, Waltham, Mass.) according to the manufacturer's instructions. This kit measures extracellular LDH in culture medium using an enzymatic reaction that results in a red formazan product, which can be measured spectrophotometrically. The absorbance was measured at 490 and 680 nm. All LDH levels were normalized to untreated controls and presented as fold change of the controls.

2.6. Flow Cytometry

Characterization of cell death was performed by flow cytometry using the Alexa Fluor® 488 Annexin V/Dead Cell Apoptosis kit (Thermo Fisher Scientific). This kit contains recombinant, green fluorophore-conjugated annexin V, which reacts with apoptotic cells, and DNA-binding, red-fluorescent propidium iodide (PI), which is impermeant to live and apoptotic cells, but stains dead cells. The different cell populations can be distinguished by green fluorescence (apoptotic cells), red fluorescence (necrotic/dead cells), and no fluorescence (live cells) during flow cytometry with 488 nm laser excitation. Control or drug-treated cells were processed as per manufacturer's instructions, followed by flow cytometry of 10,000 cells per point with an LSR II (BD Biosciences, San Jose, Calif.) at the USC Flow Cytometry Core Facility.

2.7. ATP Assay

ATP content of cells was measured with the ATP Colorimetric/Fluorometric Assay kit (Biovision Inc., Milpitas, Calif.), which utilizes the phosphorylation of glycerol to generate a product that is quantified by colorimetry at 570 nm. Approximately $1 \times 10^6$ cells were cultured in 10-cm tissue culture plates, exposed to drug treatment for various time periods, and then processed as per manufacturer's instructions. All ATP levels were normalized to untreated controls and presented as percentage of controls.

2.8. GAPDH Activity Assay

Enzymatic activity of GAPDH in vitro was measured with the Colorimetric GAPDH Assay kit (ScienCell Research Laboratories, Carlsbad, Calif.). This assay is based on the oxidization of β-NADH to β-NAD in the presence of 3-phosphoglyceric acid, ATP and GAPDH. GAPDH activity is determined by assaying the rate of NADH oxidation, which is proportional to the reduction in absorbance at 340 nm over time (ΔA340 nm/min). One hundred thousand cells were lysed in 100 µL cell lysis buffer and incubated with the above components. Changes in absorbance over 10 minutes were calculated and normalized to untreated controls. Data are presented as percentage of controls. Two types of drug treatments were performed: in one approach, drugs were added to proliferating cells for 30 minutes under regular cell culture conditions; in the other approach, drugs were added to cell lysates for 1 hour at 4° C.

2.9. MCT1 Knockdown

All siRNAs were purchased from Qiagen, Valencia, Calif. To knock down MCT1 expression, we used siRNA Hs_SLC16A1_6 (target sequence: 5'-CAGCAGTA-TCCTGGTGAATAA-3'). As a non-silencing control, we used AllStars Negative Control siRNA, which lacks homology to any known mammalian gene. One hundred thousand cells per well of a 6-well plate were transfected with 50 nM siRNA using jetPRIME transfection reagent and buffer (Polyplus Transfection, New York, N.Y.). Medium was changed after 24 hours and cells were subjected to experiments 72 hours after transfection. 2.10. Immunoblots Total cell lysates were analyzed by Western blot analysis as described earlier [40]. Primary antibodies against cleaved caspase 7 and PARP were obtained from Cell Signaling Technology (Danvers, Mass.), and antibodies against actin (C-11) and MCT1 (H-1) were obtained from Santa Cruz Biotechnology (Santa Cruz, Calif.). All antibodies were used according to the manufacturers' recommendations, except that in the case of MCT1 detection, the boiling step was omitted before loading the samples onto the polyacrylamide gel. All immunoblots were repeated at least once to confirm the results.

2.11. Immunocytochemistry

HCT116 cells were seeded onto glass coverslips in 24-well plates at $1-2\times10^5$ cells per well. The next day, cells were fixed in acetone for 10 min., followed by blocking with SEA blocking buffer (Thermo Fisher Scientific) for 30 min. and overnight incubation with MCT1 antibody (1:50; H1, Santa Cruz) at room temperature. The secondary antibody was biotinylated horse anti-mouse IgG (1:200; Vector Laboratories, Burlingame, Calif.). Cells were counterstained with hematoxylin for 20 seconds and then mounted in Vecta-Mount AQ mounting medium (Vector Laboratories).

2.12. Liquid Chromatography-Mass Spectrometry

LC/MS experiments were performed on a Q Exactive™ Hybrid Quadrupole-Orbitrap mass spectrometer connected to an Easy-nLC 1000 system. The analytical column was a C18 EASY-Spray column, 25 cm×75 µm ID, filled with 2 µm particles (100 Å pore size), connected in series with a C18 cartridge trapping column, 5 mm×300 µm ID, filled with 5 µm particles (100 Å pore size). The reaction products were resolved with a flow rate of 300 nL/min and a 150-minute gradient. Solvent A was 100% water containing 0.1% formic acid. Solvent B content (100% acetonitrile containing 0.1% formic acid) was increased from 2 to 44% within 140 minutes. The resolved reaction products were then analyzed under data-dependent acquisition mode with a survey scan between 375 to 1700 m/z, with a resolution of 70,000 at 200 m/z, and AGC target of 1e6 (maximum injection time was set at 60 ms). Following the survey scan, top 10 product ions were selected for fragmentation, under normalized collision energy (NCE) of 27, with a resolution of 17,500 at 200 m/z, and AGC target of 5e4 (maximum injection time was set at 64 ms). Data analysis of raw mass spectrometry data was done with Xcalibur™ and Proteome Discoverer software developed by Thermo Scientific.

Interaction with GAPDH: Purified GAPDH protein (30 µg, 1 µg/µl) from rabbit muscle (ScienCell Research Laboratories) was incubated with 60 µM 3-BP or NEO218 in 50 mM ammonium bicarbonate for 15 min at room temperature, followed by storage at −20° C. until further processing. The reagent was removed using a 3K centrifuge filter at 10,000 g force. Then, the filter was added with 100 µL of 50 mM ammonium bicarbonate buffer and treated for one hour with addition of 10 mM 2-iodoacetamide to alkylate the free cysteines on GAPDH. Digestion was performed in two steps with a total ratio of 1/50 (trypsin/GAPDH). First, half the amount of trypsin was added and the mixture was incubated at 37° C. for two hours while the filter was vortexed every 30 minutes. Second, the remaining amount of trypsin was added and the mixture was incubated overnight. The reaction was terminated after 16 hours of digestion by adding 1 vol % formic acid. Five microliters of reaction mixture were loaded to the trapping column for analysis. The modified cysteine residues on GAPDH tryptic peptides were identified by defining the target reaction as a dynamic modification.

Interaction with GSH and NAC: Equimolar concentrations (10 mM in a volume of 50 µL) of NEO218 and GSH or NAC were reacted for one hour at 37° C. or 50° C. An aliquot of the reaction mixture was loaded onto the trapping column for LC/MS analysis. Reaction products were identified by their nominal m/z value peaks, in combination with isotope distribution and intensities ($^{13}$C isotope peaks).

2.13. Statistical Analysis

All parametric data were analyzed using the Student t-test to calculate the significance values. A probability value (p)<0.05 was considered statistically significant.

3. Results 3.1. Cytotoxic Potency a Novel 3-BP Analog, NEO218

Because it was reported that the cytotoxic effects of 3-BP in vitro depend on the presence of MCT-1, we began our study by characterizing MCT-1 expression levels along with cytotoxicity of 3-BP in the various tumor cell lines to be used in our study. We included one colon carcinoma cell line (HCT116), three glioblastoma cell lines (LN229, T98G, U251), four breast cancer cell lines (MCF7, T47D, MDA-MB-231, MDA-MB-468), one culture of primary breast cancer cells (BTM-12), and an established line of normal breast epithelial cells (ME16C). For all 10 cell lines, we established IC50 (concentration of drug that kills 50% of the cell population) by MTT assay, along with MCT-1 protein levels by Western blot analysis. As summarized in FIGS. 16A-16C, MCT-1 levels varied greatly in the different cells, and so did their IC50 values. However, there was a clear correlation between the two: those cells with high MCT-1 levels (HCT116, U251, ME16C, MDA-MB-468) showed substantially lower IC50s (15-60 µM) than those cells with lesser MCT-1 levels (IC50s: 150-300 µM). These results are consistent with earlier data that sensitivity of cells to 3-BP requires high MCT-1 expression levels.

In order to study the anticancer effects of 3-BP further, we created an analog thereof, where the monoterpene POH was covalently conjugated to 3-BP. This novel chimera, now consisting of two permanently fused anticancer compounds, was termed NEO218 (FIG. 1). We then performed MTT assays for all 10 cell lines to compare the cytotoxic activity of NEO212 side-by-side to 3-BP. Intriguingly, NEO218 was similarly potent in each and every cell line, with an IC50 in the narrow range of 15 to 25 µM (FIGS. 16A-16C), irrespective of MCT-1 expression levels.

To validate this clear differential between the two agents, we performed additional cell toxicity assays with only two cell lines: HCT116 cells, representing high MCT-1 expression and high sensitivity to 3-BP, compared to MDA-MB-231 cells, representing very low MCT-1 expression and very low sensitivity to 3-BP. These cells were treated with increasing concentrations of 3-BP or NEO218, and drug impact was quantitated by MTT short-term toxicity assay, lactate dehydrogenase (LDH) release assay, and long-term colony formation assay (CFA). The results are presented in detail in FIGS. 17A-17C and can be summarized as follows: 3-BP exerted strong potency in HCT116 cells, but only little potency in MDA-MB-231 cells, and this was consistently observed in all three assay. In comparison, NEO218 was highly potent in both cell lines in all three assays. In HCT116 cells, 3-BP and NEO218 were active at very similar concentrations, with half-maximal effects at approximately 18 µM, 8 µM, and 3 µM in MTT, LDH, and CFA assays, respectively. In MDA-MB-231 cells, NEO218 maintained the same high potency, but the effective concentrations of 3-BP greatly increased to about 220 µM, 350 µM, and 130 µM, respectively, in the three assays (FIGS. 17A-17C). Thus, irrespective of the experimental assessment procedure, 3-BP and NEO218 were similarly active in MCT-1 positive cells; in MCT-1-negative cells, however, 3-BP was strikingly less active, whereas NEO218 continued to exert its full cytotoxic potential.

Because NEO218 was generated via conjugation of two individual compounds, where each one was known to harbor anticancer potential, we next investigated whether a mere mix of 3-BP together with POH would be able to mimic the activity of NEO218. MDA-MB-231 cells were treated with either NEO218, 3-BP, POH, or a mix of 3-BP plus POH, and analyzed by MTT, LDH, and CFA assays. As before, NEO218 was highly potent in all these assays, whereas 3-BP was much less active (FIGS. 18A-18C). POH alone exerted only very weak cytotoxic effects, with an IC50 approaching the millimolar range, which is consistent with many other studies that have analyzed the anticancer effects of this compound. Of note, the mix of 3-BP plus POH was not more active than 3-BP alone; that is, adding POH to 3-BP did not increase the cytotoxic outcome over the effects of 3-BP alone (FIGS. 18A-18C), indicating novel physiochemical properties of the 3-BP analog.

3.2. Role of MCT-1 in Drug Effects

The above results indicated that cytotoxic effects of NEO218 did not require the presence of MCT-1. To further validate this conclusion, we used siRNA transfection to knock down MCT-1 expression in HCT116 cells. As would be expected, such reduction of MCT-1 expression resulted in pronounced resistance against 3-BP, and the IC50 increased more than three-fold from 20 µM to 67 µM (FIG. 19A). In comparison, the IC50 toward NEO218 did not increase, but rather decrease to a small extent from 19 µM to 15 µM. As a control, we confirmed siRNA-mediated down-regulation of MCT-1 by Western blot (FIG. 19B) and immunohistochemistry (FIG. 19C).

In some of our toxicity assays with HCT116 cells, we noticed that, after treatment with 3-BP but not after treatment with NEO218, the slope of the dose-response curve seemed to level off (e.g., FIG. 17A), suggesting the presence of a small sub-population of cells that was more resistant to 3-BP than the rest. Upon closer inspection of individual cells by immunohistochemistry, we detected a small number of apparently MCT-1-negative cells among the otherwise mostly MCT-1-positive population (FIG. 20A). This aspect was investigated further by treating HCT116 cells with 40 µM, representing a concentration that reduces apparent viability by 75% in MTT assays (FIG. 17A) and blocks colony formation by 99% in CFAs. After overnight 3-BP treatment, HCT116 cells were left to recover, and after about two weeks the cell population was fully restored. These cells, which we called 3-BP survivors, were further analyzed. Intriguingly, no MCT-1 expression could be detected in these cells, neither by immunohistochemistry (FIG. 20A) nor by Western blot (FIG. 20B). When we analyzed their sensitivity to 3-BP, we found that they had become strikingly resistant to this compound, with an IC50 that was well above 100 µM and in the range of IC50s documented for the MCT-1-negative cells shown in FIGS. 16A-16C. Together, these results indicated that 3-BP treatment effectively selected for MCT-1-negative cells, which rapidly restored the cell population in a subsequently 3-BP-resistant manner. Intriguingly, NEO218 had no such effect. On one hand, treatment of HCT116 cells with 40 µM NEO218 did not leave any surviving cells; on the other hand, highly 3-BP-resistant 3-BP survivors retained their high sensitivity toward NEO218 (FIG. 20C).

3.3. Establishing Necrosis as the Predominant Type of Cell Death

We next characterized drug-induced cell death, and in particular sought to distinguish between apoptosis and necrosis in response to treatment of cells with 3-BP or NEO218. We first performed FACS analysis of drug-treated cells to investigate annexin V positivity (a marker for apoptosis) versus propidium iodide (PI) incorporation (a marker of necrotic cells). We used staurosporine (STS) as a well-established positive control for apoptotic cell death. As can be seen in FIG. 21A, STS performed as expected: HCT116 cells treated with this agent moved from the lower left quadrant (=fully viable cells) to the lower right quadrant (=annexin V-positive cells), before slowly accumulating in the upper right quadrant (=PI-positive, dead cells). In striking contrast, both 3-GP and NEO218 treatment caused the cells to move straight from the bottom left quadrant to the upper right quadrant. This effect was quite rapid and detectable as early as 2 hours after the onset of treatment; at 8 hours, the majority of cells was PI-positive (FIG. 21A), indicating a preponderance of necrosis, rather than apoptosis.

Second, we analyzed typical markers of apoptosis, specifically the proteolytic cleavage of PARP (poly-ADP-ribose polymerase), the activation of caspase 7 (C-7), and emergence of phosphorylated HA2X protein (□-HA2X, indicating damage and degradation of DNA). HCT116 and MDA-MB-231 cells were treated with 3-BP or NEO218 at their respective cytotoxic concentrations, or with STS as the positive control for induction of apoptosis. FIG. 21B shows that STS, as expected, triggered pronounced cleavage of PARP, activation of C-7, and appearance of □-HA2X. In comparison, however, all three apoptosis markers responded only minimally, if at all, to 3-BP or NEO218. We also determined whether inclusion of Z-VAD-FMK, a potent pan-caspase inhibitor, would be able to impinge on cytotoxic impact of 3-BP or NEO218. However, as shown in FIG. 21C, this was not the case, i.e., inhibition of caspase activation did not affect the cytotoxic IC50 of the two drugs, further indicating a lack of typical apoptotic events.

As it is known that apoptosis is an active process that requires cellular energy, we next determined cellular ATP levels after drug treatment. As a point of reference, we also cultured cells in the presence of rotenone (a mitochondrial respiratory complex I inhibitor) in medium lacking glucose (to minimize glycolysis), which are culture conditions known to cause necrotic cell death due to ATP levels dropping below the ~25% operational threshold. As shown in FIG. 22 with the use of HCT116 cells, such hostile culture conditions indeed resulted in rapid ATP depletion, breaching the 25% threshold within the first 3 hours of treatment, and dropping further to about 10% of normal after six hours. In striking similarity, treatment of cells with 3-BP or NEO218 resulted in nearly identical outcomes (FIG. 22). Taken together, these results present necrosis as the dominant mechanism of cell death for both compounds, secondary to the severe depletion of cellular energy levels.

3.4. Mechanism of Drug-Induced Cytotoxicity

Having established that both 3-BP and NEO218 caused rapidly lethal termination of cellular energy production, we next set out to determine the cause for this effect. It had been reported by others that addition of excess pyruvate, or supplementation with antioxidants, was able to protect cells from the cytotoxic effects of 3-BP in vitro. We therefore pursued these leads and investigated whether they would apply to NEO218 as well. HCT116 cells were treated with NEO218 or 3-BP in the presence or absence of pyruvate or antioxidants (N-acetylcysteine, NAC, and glutathione, GSH), and cellular viability was determined 24 hours later. As expected, each of the three exogenously added compounds was able to exert profound protection against 3-BP toxicity. In the case of NEO218, however, there was a striking difference. While antioxidant treatment similarly protected cells against NEO218, there was no protection at all when pyruvate was added (FIG. 23A). (See Discussion regarding the interpretation of this effect.)

As 3-BP had been reported as an inhibitor of glyceraldehyde 3-phosphate dehydrogenase (GAPDH), we next studied GAPDH enzymatic activity. First, HCT116 cells were treated with 3-BP or NEO218, and 30 minutes later cells were lysed for the determination of GAPDH activity. As shown in FIG. 23B, GAPDH activity was severely inhibited by either compound, with an IC50 slightly below 30 µM. Second, drug effects on GAPDH activity were determined in cell-free extracts, where drugs were added not to living cells, but rather to cell lysates. As shown in FIG. 23C, both compounds potently decreased enzymatic GAPDH activity under these conditions as well. Surprisingly however, in the presence of antioxidants (NAC or GSH) this inhibitory effect was completely prevented, even though these were cell-free reaction conditions without the possibility of free radical production by intact mitochondria or other cellular processes. This outcome suggested that the protective effects of NAC or GSH might not be via their conventional quenching of free radical species. (See Discussion regarding an alternative model explaining cytoprotection by NAC and GSH.)

Based on the known akylating nature of 3-BP, we next addressed the question whether both 3-BP and NEO218 would be able to covalently pyruvylate GAPDH protein. The amino acid sequence of GAPDH contains 4 cysteines (in rabbit at positions 150, 154, 245, 282), and their thiol functionalities represent potential candidates for nueleophilic addition. We incubated purified rabbit GAPDH protein with either 3-BP or NEO218 and analyzed the resulting products by mass spectrometry. This analysis clearly identified covalently modified cysteines. In the case of incubation with 3-BP, all 4 cysteines were altered by the addition of pyruvate; in the case of incubation with NEO218, the same four residues revealed attachment of pyruvate-perillyl alcohol moieties (FIG. 24A). Taken together, the above results indicated that 3-BP and NEO218 caused inhibition of GAPDH enzyme activity via alkylation of its cysteine residues, in particular active site Cys-150 (equivalent to Cys-152 in human GAPDH), which is known to be most critical for enzymatic function [44].

We also considered that NEO218 (and 3-BP) might have many other targets, and therefore investigated the potential direct interaction with GSH and NAC as well. Purified GSH or NAC were mixed with NEO218 in vitro, followed by mass spectrometric analysis. Both antioxidants readily interacted with the 3-BP analog. In the case of GSH+NEO218, the reaction resulted in one predominant fusion product (FIG. 24B), consistent with a nucleophilic replacement reaction that would result in an inactive complex. In the case of NAC+NEO218, many different reaction products were obtained, and one of the major ones was selected for further analysis. The chromatogram of this product indicated a nucleophilic addition reaction, where the bromide residue of NEO218 may not have left the final reaction product structure (FIG. 24C), nonetheless clearly demonstrating the interaction of NAC with NEO218. Characterization of the other reaction products was not performed. Altogether, these results demonstrate direct interactions between NEO218 and GSH or NAC. Based on this outcome, supplemental GSH or NAC would be postulated to protect cells from NEO218 (or from 3-BP) primarily by quenching the electrophilic potential of the alkylating compounds.

4. Discussion

3-BP is under development as an anticancer agent or liver cancer, but its exact mechanism of action is not entirely clear. For instance, while depletion of cellular energy levels by 3-BP has been well established, it is not entirely clear how this is accomplished, although oftentimes it is cited that blockage of glycolysis, via 3-BP's well-documented inhibition of GAPDH (or perhaps hexokinase) is responsible. Many reports have presented oxidative stress as a key component of 3-BP-induced cell death, and autophagy and different signaling pathways have been implicated as well. We have created NEO218, a POH-linked analog of 3-BP, which turned out to be very useful in further illuminating the role of some of these mechanisms; in addition, this analog revealed novel features that are of relevance in the context of cancer therapy.

Our side-by-side in vitro analysis of 3-BP and NEO218 revealed important commonalities, as well as intriguing differences that provided key clues to a better understanding of 3-BP's cytotoxic mechanism. Based on our new data, combined with results from pertinent recently published studies by others, we would like to propose an updated model of 3-BP action (as detailed below), and introduce its analog NEO218 as a novel asset for further studies.

Figure 16:
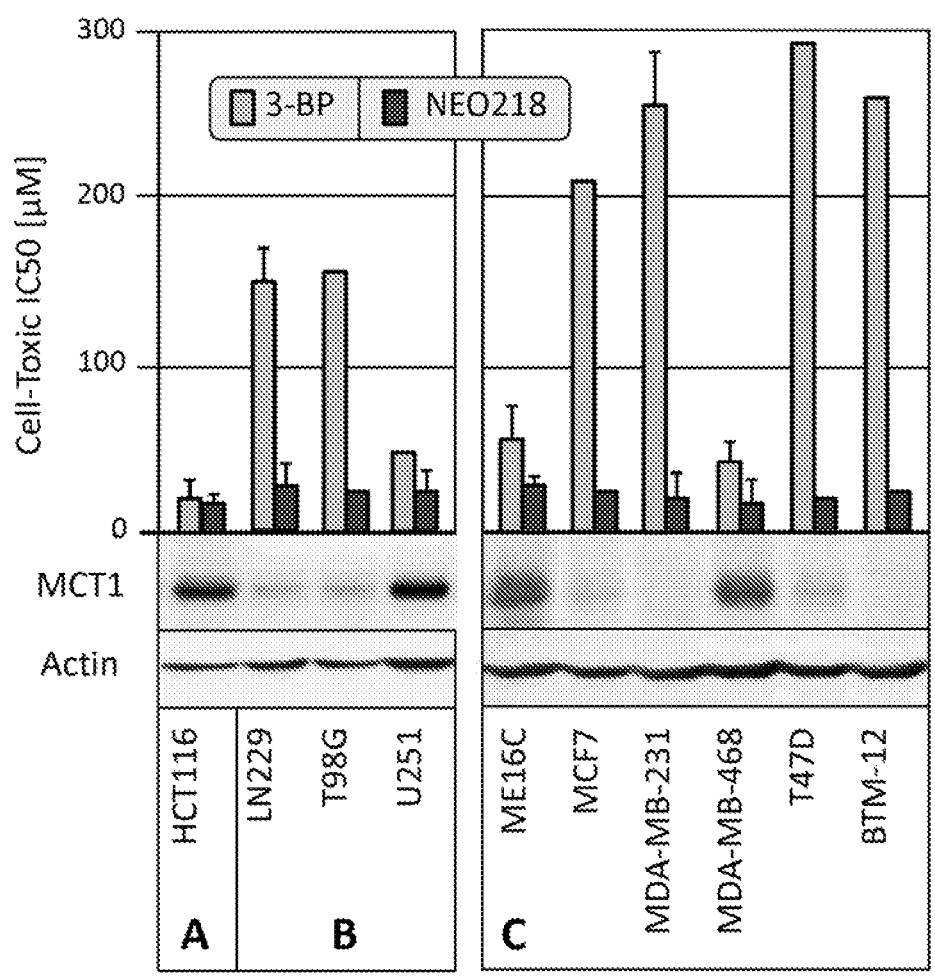
FIGS. 16A-16C. MCT-1 expression correlates with 3-BP chemosensitivity.

The key difference between 3-BP and NEO218 is with regard to their entry into cells. It has been established that 3-BP enters cells is active transport by transmembrane MCT-1 [10], and we confirmed this model as follows: (i) In all 10 different cell lines tested, the cytotoxic IC50 of 3-BP was closely aligned with their respective MCT-1 protein levels; i.e. cells with high MCT-1 protein levels consistently displayed much lower IC50s than cells with low MCT-1 levels (FIGS. 16A-16C). (ii) Knock-down of MCT-1 resulted in increased resistance to killing by 3-BP (FIGS. 19A-19C). (iii) HCT-116 cells selected for lack of MCT-1 expression were highly resistant to 3-PB, whereas MCT-1-positive parental cells were very sensitive (FIGS. 20A-20C). These results compared to NEO218 as follows: (iv) NEO218 was similarly potent at low concentrations (15 to 25 µM) in the same 10 cell lines, irrespective of MCT-1 expression levels. (v) The IC50 of NEO218 did not increase after knock-down of MCT-1 (FIGS. 19A-19C). (vi) HCT-116 cells selected for lack Of MCT-1 expression were as sensitive to NEO218 as their parental counterparts (FIGS. 20A-20C). Furthermore, the addition of a large molar excess of supplemental pyruvate (a known MCT-1 substrate) powerfully protected cells from 3-BP, but not from NEO218 (FIG.

23A). Altogether, these data are in full support of our model that NEO218 effectively enters cells in an MCT-1-independent fashion. Its precise mode of cellular uptake, whether by diffusion or by another active transport mechanism, remains to be established. In view of earlier observations that perillyl alcohol exerts dynamic interactions with the lipid bilayer [42], on could speculate that the covalent conjugation of this monoterpene to 3-BP confers lipophilic properties to the chimeric compound, resulting in receptor-independent membrane interactions to achieve cell entry.

Although cellular uptake is quite different between 3-GP and NEO218, the mechanism by which these two compounds cause cell death appears to be the same, i.e., once inside the cell, either compound appears to trigger the same sequence of events, with protein alkylation as the initial key step. Binding of 3-BP to GAPDH and inhibiting its activity has previously been reported [1, 2, 43]. While we confirmed inhibition of GAPDH enzymatic activity by both 3-BP and NEO218 (FIGS. 23B, 23C), we further determined that all 4 cysteine residues within the primary amino acid sequence of GAPDH were targets for alkylation (FIG. 24A). As Cys-150 in the rabbit protein (equivalent to Cys-152 in the human sequence) is known to be critical for enzymatic function [41], it is reasonable to conclude that pyruvylation represents the key mechanism by which 3-BP and NEO218 achieve inhibition of GAPDH.

As a general principle, it is well established that cysteines are the most intrinsically nucleophilic amino acids in proteins, and thiol side chains in functional cysteines readily interact with Michael acceptor-type agents ("Michael reactions") [44]. It was therefore not entirely surprising to identify GAPDH cysteines as immediate targets of 3-BP and NEO218. As a corollary, however, it also indicated that the activity of many other cellular proteins could be impacted by this type of interaction. Efforts by others [45, 46], with the use of thiol-reactive electrophiles other than 3-BP, revealed >500 (mostly unidentified) proteins with cysteines that were responsive to such modification. Although not all of these proteins were consistently modified by all electrophiles, it seemed that certain protein families were more sensitive than others, and a specific core group was modified by all electrophiles tested. In the context of 3-BP and NEO218, one could extrapolate that many other proteins besides GAPDH might be targeted and might participate in conveying these agents' cytotoxic impact. Indeed, a number of other enzymes from bacteria to fungi to humans were shown to be inhibited by 3-BP [13-21], including succinate dehydrogenase (SDH), a key enzyme that connects the tricarboxylic acid cycle with the electron transport chain [2, 19, 47].

The large number of potential targets for 3-BP and NEO218 raises the question as to which ones are critically involved in mediating drug-induced cell death. As shown by others [22, 24, 48], and validated by us for NEO218 as well (FIG. 22), 3-BP causes severe depletion of cellular ATP pools, a condition that is unable to sustain cellular viability and well known to inevitably result in necrosis [49-51]. Thus, among the very many potential targets of 3-BP and NEO218, simultaneous inhibition of GAPDH and SDH stands out, because without the vigorous activity of these two enzymes, cells are unlikely able to produce sufficient energy for survival. The presumed importance of SDH, alongside GAPDH, is further underscored by our finding that supplemental pyruvate is completely ineffective in overcoming NEO218-induced cell death (FIG. 23A). This is in stark contrast to findings by others [8, 9] and our own (FIG. 23A), demonstrating powerful protection provided by supplemental pyruvate against 3-BP. While earlier interpretations suggested that pyruvate overcame 3-BP toxicity (i.e., neutralized the consequences of GAPDH inhibition) by providing the missing glycolytic end product, our side-by-side comparison with NEO218 instead posits that (the large molar excess of) added pyruvate protects cells from 3-BP via effective competition for cellular uptake through MCT-1. Furthermore, complete removal of glucose from the growth medium does not significantly impact short-term survival of the tumor cells used in our study, and clearly does not mimic 3-BP-induced cell death (not shown). On the other hand, simultaneous inhibition of glycolysis and mitochondrial respiration (through removal of glucose and concurrent addition of rotenone) closely mimicked the rapid kinetics of ATP depletion caused by 3-BP and NEO218 (FIG. 22). Altogether, our model—consistent with observations by others [47, 52, 53]—favors potent simultaneous inhibition of GAPDH and SDH as the key initial trigger of cell death induced by 3-BP and NEO218, although the contribution of other potential targets is conceivable and remains to be established.

Inhibition of GAPDH in response to cellular treatment by 3-BP and NEO218 might be exacerbated further by ROS. 3-BP has been shown to lower cellular GSH levels, resulting in increased ROS levels [22, 23]. Since glycolytic GAPDH activity can be inhibited by high ROS levels [54], it is quite possible that GAPDH is shut down by a two-pronged attack mounted by pyruvylation plus ROS. Whether or not this additional repression by ROS is needed, on top of pyruvylation, in order to deplete ATP pools below life-supporting levels, remains to he established. Several previous studies [8, 24, 25, 55] used supplemental antioxidants, primarily added GSH and NAC, as tools to investigate the role of ROS in 3-BP-induced cell death, and observed that either one was strikingly potent in protecting cells from 3-BP, similar to what we show in FIGS. 23A-23C with both 3-BP and NEO218. While this outcome had been taken as an indication that the generation of ROS was indeed essential to mediate cell death by 3-BP, our results indicate otherwise.

For instance, 3-BP and NEO218 inhibited GAPDH activity also in a cell-free system, where ROS are unlikely to play a role, and the addition of GSH or NAC proved protective under these conditions as well (FIG. 23C). Furthermore, similar to the potent interaction of NEO218 with cysteine thiol groups of GAPDH, NEO218 directly interacted with nucleophilic GSH and NAC also, as revealed by LC/MS analysis (FIGS. 24A-24C). While we did not include 3-BP in this mass spectrometric analysis, a recent report by others demonstrated direct interaction of GSH with 3-GP in the absence of cells, as well as intracellularly in erythrocytes and MCF7 cells [56]. Combined, these observations favor a model where molar excess of supplemental GSH and NAC acts by effectively binding and neutralizing 3-BP/NEO218, thus preventing ROS production in the first place, rather than by secondarily quenching increased levels of ROS. Altogether, while it is clear that 3-BP does increase ROS levels via the depletion of intracellular GSH pools [22, 23, 43] (and possibly via effects on mitochondrial respiration [57]), it remains to be established whether these ROS are indeed required for drug-induced cell death—or whether instead the pyruvylation-mediated inactivation of key metabolic enzymes might suffice.

The mechanism of 3-BP-induced cell death has been variable reported as apoptosis, necroptosis or necrosis (e.g., refs. [22, 24, 26, 58, 59]). In the context of chemotherapy, this distinction is important. As has been, pointed out in a recent review [60], contrary to some commonly-held beliefs, necrosis rather than apoptosis should be the preferred cell death mode for most effective chemotherapy. We took great care to illuminate this issue from different perspectives, with the inclusion of staurosporine as a positive control for apoptotic events. We also used MCT-1-positive and -negative cells, which allowed us to investigate the possibility that the events at high 3-BP concentration perhaps might be different from those at low concentrations.

All our data are highly consistent and point to necrosis as the overwhelmingly dominant mechanism of cell death by both 3-BP and NEO218 in our cell systems, as supported by the following observations: (i) A pan-caspase inhibitor exerted no influence on the cytotoxic IC50 of 3-BP or NEO218 (FIG. 21C). (ii) Several established protein markers of apoptosis show very little, if any, response to drug treatment (FIG. 21B). (iii) Loss of structural integrity of the plasma membrane is a hallmark of necrosis [61, 62] and can be documented via cellular uptake of membrane-impermeant dyes (such as propidium iodide, PI) or cellular leakage of cytosolic enzymes (such as lactate dehydrogenase, LDH). Our FACS analysis showed substantial accumulation of PI-positive cells (FIG. 21A) and extensive leakage of LDH (FIGS. 17A-17C). The loss of plasma membrane integrity is consistent with cell death induced by the severe ATP depletion observed by us (FIG. 22) and reported by others [22, 24, 48], because maintenance of the cytoplasmic transmembrane electrochemical gradients is highly energy dependent, and their loss inevitably leads to cell swelling and membrane rupture (i.e., necrosis) [62]. (iv) Rapid cell death is another characteristic of necrotic cell death [63]. We detected PI positivity and LDH release within the first 2 hours of drug exposure (see FIG. 21A for PI; time course not shown for LDH). (v) Although severe depletion of ATP already suggested that any sort of programmed event should be precluded, we did investigate programmed necrosis, a.k.a. necroptosis [64], as a possible mechanism of drug-induced cell death. Cells were treated with 3-BP or NEO218 in the presence of necrostatin-1 (Nec-1), a commonly used inhibitor of necroptosis [63]. However, no impact of Nec-1 on drug-induced cytotoxic outcome could be detected (not shown).

In our study, we included staurosporine as a reference agent for induction of apoptosis, which proved quite useful for a meticulous distinction between necrotic and apoptotic events induced by 3-BP and NEO218. For instance, in our Western blots analyzing traditional markers of apoptosis (FIG. 21B), we do detect the appearance of faint positive signals after drug treatment. Although much longer exposure of these blots would have significantly enhanced these signals further—and would have pointed to extensive apoptosis—our comparison to staurosporine-treated cells put these signals in proper perspective and confirmed only little, if any, involvement of apoptotic processes. Furthermore, loss of membrane integrity (a feature of necrosis) will enable annexin V incorporation, and therefore it is important to remember that annexin V-positive cells that are also PI positive are not apoptotic, but necrotic. This is nicely exemplified by our FACS analysis (FIG. 21A), where staurosporine-treated cells first move into the lower right quadrant (annexin V positive; PI negative) before moving into the upper right quadrant (annexin V positive; PI positive). In comparison, the vast majority of cells treated with 3-BP or NEO218 do not appear in the lower right quadrant, but rather move straight from lower left to upper right. Combined, the data from our detailed analysis establish necrosis as the clearly predominant form of cell death induced by 3-BP and its analog NEO218 in the tumor cell lines used in our study. It should be noted, however, that other cell types might respond differently, as cell-type specific cell death processes in response to 3-BP have been reported [26].

In cancer therapy, the development of treatment resistance is a widespread problem that usually spells poor prognosis for affected patients. In this context, it was intriguing to find that a single 3-BP treatment of highly sensitive HCT116 cells resulted in rapid accumulation of 3-BP resistant cells, apparently because drug treatment killed off MCT-1-positive cells, but allowed for survival and escape of a minority of MCT-1-negative cells that already were present in the population before the onset of treatment (FIG. 20A-20C). While it is unknown whether MCT-1-positive tumor tissues in patients would harbor a subset of MCT-1-negative cells, our example provides a cautionary signal that downregulation of MCT-1 expression (FIGS. 19A-19C), or the presence of an MCT-1-negative tumor cell subpopulation (FIGS. 20A-20C), could lead to treatment resistance in the clinic. Intriguingly however, increased resistance to NEO218 was not observed, and in fact resistant cells emerging from 3-BP treatment were still highly responsive to NEO218 (FIGS. 20A-20C), further emphasizing the MCT-1-independent function of this analog.

5. Conclusions

The sum of our results are consistent with the conclusion that the molecular activities by which 3-GP and NEO218 accomplish cell killing are identical. The only noted difference is that 3-BP requires transport by MCT-1 to enter cells, whereas NEO218 does not. However, once inside the cell, 3-BP and NEO218 trigger the same sequence of cytotoxic events at similar potency, as follows: Both agents rapidly pyruvylate several key metabolic enzymes (GAPDH, SDH, and possibly others), thereby inhibiting their activities. As an immediate consequence, both glycolysis and mitochondrial respiration shut down, causing ATP levels to rapidly drop below life-sustaining levels. As it has been well established that in the absence of sufficient ATP, energy-dependent cellular functions are incapacitated [49-51, 65-67], the cells are left with no other option than necrosis. However, cells are shielded from the cytotoxic impact of low to moderate concentrations of 3-BP in vitro if they express only little or no MCT-1. Extrapolated to future cancer therapy with 3-BP, such cells would be expected to drive the emergence of treatment resistance and spell poor prognosis for the patient. Intriguingly, this in vitro effect was not observed with NEO218, providing a rationale for its further characterization as an anticancer agent.

REFERENCES

[1] S. Ganapathy-Kanniappan, J. F. Geschwind, R. Kunjithapatham, M. Buijs, J. A. Vossen, I. Tchernyshyov, R. N. Cole, L. H. Syed, P. P. Rao, S. Ota, M. Vali, Glyceraldehyde-3-phosphate dehydrogenase (GAPDH) is pyruvylated during 3-bromopyruvate mediated cancer cell death, Anticancer Res, 29 (2009) 4909-4918.

[2] A. P. Pereira da Silva, T. El-Bacha, N. Kyaw, R. S. dos Santos, W. S. da-Silva, F. C. Almeida, A. T. Da Poian, A. Galina, Inhibition of energy-producing pathways of HepG2 cells by 3-bromopyruvate, Biochem J, 417 (2009) 717-726.

[3] S. Cardaci, E. Desideri, M. R. Ciriolo, Targeting aerobic glycolysis: 3-bromopyruvate as a promising anticancer drug, J Bioenerg Biomembr, 44 (2012) 17-29.

[4] M. C. Shoshan, 3-Bromopyruvate targets and outcomes, J Bioenerg Biomembr 44 (2012) 7-15.
[5] Q. Tran, H. Lee, J. Park, S. H. Kim, J. Park, Targeting Cancer Metabolism—Revisiting the Warburg Effects, Toxicol Res, 32 (2016) 177-193.
[6] R. T. Wicks, J. Azadi, A. Mangraviti, I. Zhang, L. Hwang, A. Joshi, H. Bow, M. Hutt-Cabezas, K. L. Martin, M. A. Rudek, M. Zhao, H. Brem, B. M. Tyler, Local delivery of cancer-cell glycolytic inhibitors in high-grade glioma, Neuro Oncol, 17 (2015) 70-80.
[7] P. Dell'Antone, Targets of 3-bromopyruvate, a new, energy depleting, anticancer agent, Med Chem, 5 (2009) 491-496.
[8] S. M. El Sayed, R. M. Abou El-Magd, Y. Shishido, S. P. Chung, T. Sakai, H. Watanabe, S. Kagami, K. Fukui, D-amino acid oxidase gene therapy sensitizes glioma cells to the antiglycolytic effect of 3-bromopyruvate, Cancer Gene Ther, 19 (2012) 1-18.
[9] S. M. El Sayed, El-Magd, Y. Shishido, S. P. Chung, T. H. Diem, T. Sakai, H. Watanabe, S. Kagami, K. Fukui, 3-Bromopyruvate antagonizes effects of lactate and pyruvate, synergizes with citrate and exerts novel anti-glioma effects, J Bioenerg Biomembr, 44 (2012) 61-79.
[10] K. Birsoy, T. Wang, R. Possemato, O. H. Yilmaz, C. E. Koch, W. W. Chen, A. W. Hutchins, Y. Gultekin, T. R. Peterson, J. E. Carette, T. R. Brummelkamp, C. B. Clish, D. M. Sabatini, MCT1-mediated transport of a toxic molecule is an effective strategy for targeting glycolytic tumors, Nat Genet, 45 (2013) 104-108.
[11] A. P. Halestrap, Monocarboxylic acid transport, Compr Physiol, 3 (2013) 1611-1643.
[12] F. Baltazar, C. Pinheiro, F. Morais-Santos, J. Azevedo-Silva, O. Queiros, A. Preto, M. Casal, Monocarboxylate transporters as targets and mediators in cancer therapy response, Histol Histopathol, 29 (2014) 1511-1524.
[13] M. Brock, D. Darley, S. Textor, W. Buckel, 2-Methylisocitrate lyases from the bacterium *Escherichia coli* and the filamentous fugus *Aspergillus nidulans*: characterization and comparison of both enzymes, Eur J Biochem, 268 (2001) 3577-3586.
[14] M. L. Fonda, R. F. DeGrella, Inactivation of glutamate decarboxylase by bromopyruvate, Biochem Biophys Res Commun, 56 (1974) 451-458.
[15] P. O. Göthe, P. O. Nyman, Inactivation of human erythrocyte carbonic anhydrases by bromopyruvate, FEBS Lett, 21 (1972) 159-164.
[16] Y. H. Ko, B. A. McFadden, Alkylation of isocitrate lyase from *Escherichia coli* by 3-bromopyruvate, Arch Biochem Biophys, 278 (1990) 373-380.
[17] P. M. Alliel, B. Guiard, R. Ghrir, A. M. Becam, F. Lederer, Bromopyruvate as an affinity label for Baker's yeast flavocytochrome b2. Identification of an active-site cysteine and characterization of some cysteine peptides, Eur J Biochem, 122 (1982) 553-558.
[18] S. Hanau, M. Bertelli, F. Dallocchio, M. Rippa, Bromopyruvate for the affinity labelling of a single cysteine residue near the carboxylate binding site of lamb liver 6-phosphogluconate dehydrogenase, Biochem Mol Biol Int, 37 (1995) 785-793.
[19] B. M. Sanborn, N. T. Felberg, T. C. Hollocher, The inactivation succinate dehydrogenase by bromopyruvate, Biochim Biophys Acta, 227 (1971) 219-231.
[20] Y. H. Ko, P. L. Pedersen, J. F. Geschwind, Glucose catabolism in the rabbit VX2 tumor model for liver cancer: characterization and targeting hexokinase, Cancer Lett, 173 (2001) 83-91.
[21] Z. Chen, H. Zhang, W. Lu, P. Huang, Role of mitochondria-associated hexokinase II in cancer cell death induced by 3-bromopyruvate, Biochim Biophys Acta, 1787 (2009) 553-560.
[22] D. Valenti, R. A. Vacca, L. de Bari, 3-Bromopyruvate induces rapid human prostate cancer cell death by affecting cell energy metabolism, GSH pool and the glyoxalase system, J Bioenerg Biomembr, 47 (2015) 493-506.
[23] E. Kwiatkowski, M. Wojtala, A. Gajewska, M. Soszynski, G. Bartosz, I. Sadowska-Bartosz, Effect of 3-bromopyruvate acid on the redox equilibrium in non-invasive MCF-7 and invasive MDA-MB-231 breast cancer cells, J Bioenerg Biomembr, 48 (2016) 23-32.
[24] J. Z. Qin, H. Xin, B. J. Nickoloff, 3-Bromopyruvate induces necrotic cell death in sensitive melanoma cell lines, Biochem Biophys Res Commun, 396 (2010) 495-500.
[25] Q. Zhang, Y. Zhang, P. Zhang, Z. Chao, F. Xia, C. Jiang, X. Zhang, Z. Jiang, H. Liu, Hexokinase II inhibitor, 3-BrPA induced autophagy by stimulating ROS formation in human breast cancer cells, Genes Cancer, 5 (2014) 100-112.
[26] S. Ganapathy-Kanniappan, J. F. Geschwind, R. Kunjithapatham, M. Buijs, L. H. Syed, P. P. Rao, S. Ota, B. K. Kwak, R. Loffroy, M. Vali, 3-Bromopyruvate induces endoplasmic reticulum stress, overcomes autophagy and causes apoptosis in human HCC cell lines, Anticancer Res, 30 (2010) 923-935.
[27] E. G. Konstantakou, G. E. Voutsinas, A. D. Velentzas, A. S. Basogianni, E. Paronis, E. Balafas, N. Kostomitsopoulos, K. N. Syrigos, E. Anastasiadou, D. J. Stravopodis, 3-BrPA eliminates human bladder cancer cells with highly oncogenic signatures via engagement of specific death programs and perturbation of multiple signaling and metabolic determinants, Mol Cancer, 14 (2015) 135.
[28] M. Buijs, J. A. Vossen, J. F. Geschwind, T. Ishimori, J. M. Engles, O. Acha-Ngwodo, R. L. Wahl, M. Vali, Specificity of the anti-glycolytic activity of 3-bromopyruvate confirmed by FDG uptake in a rat model of breast cancer, Invest New Drugs, 27 (2009) 120-123.
[29] X. Cao, G. Jia, T. Zhang, M. Yang, B. Wang, P. A. Wassenaar, H. Cheng, M. V. Knopp, D. Sun, Non-invasive MRI tumor imaging and synergistic anticancer effect of HSP90 inhibitor and glycolysis inhibitor in RIP1-Tag2 transgenic pancreatic tumor model, Cancer Chemother Pharmacol, 62 (2008) 985-994.
[30] N. G. Schaefer, J. F. Geschwind, J. Engles, J. W. Buchanan, R. L. Wahl, Systemic administration of 3-bromopyruvate in treating disseminated aggressive lymphoma, Transl Res, 159 (2012) 51-57.
[31] Q. Zhang, J. Pan, P. E. North, S. Yang, R. A. Lubet, Y. Wang, M. You, Aerosolized 3-bromopyruvate inhibits lung tumorigenesis without causing liver toxicity, Cancer Prev Res (Phila), 5 (2012) 717-725.
[32] S. M. El Sayed, W. G. Mohamed, M. A. Seddik, A. S. Ahmed, A. G. Mahmoud, W. H. Amer, M. M. Helmy Nabo, A. R. Hamed, N. S. Ahmed, A. A. Abd-Allah, Safety and outcome of treatment of metastatic melanoma using 3-bromopyruvate: a concise literature review and case study, Chin J Cancer, 33 (201.4) 356-364.
[33] Y. H. Ko, H. A. Verhoeven, M. J. Lee, D. J. Corbin, T. J. Vogl, P. L. Pedersen, A translational study "case report" on the small molecule "energy blocker" 3-bromopyruvate (3BP) as a potent anticancer agent: from bench side to bedside, Bioenerg Biomembr, 44 (2012) 163-170.

[34] H. Feldwisch-Drentrup, Candidate cancer drug suspected after death of three patients at an alternative medicine clinic, AAAS, sciencemag.org/news/, 2016.

[35] P. L. Crowell, C. E. Elson, Isoprenoids, Health and Disease, in: R. E. C. Wildman (Ed.) Nutraceuticals and Functional Foods CRC Press, Boca Raton, Fla., 2001, pp. 31-54.

[36] T. C. Chen, C. O. Fonseca, A. H. Schönthal, Preclinical development and clinical use of perillyl alcohol for chemoprevention and cancer therapy, Am J Cancer Res, 5 (2015) 1580-1593.

[37] C. O. da Fonseca, K. M. Teixeira, J. C. Silva, D.E.S.D.G.F. J, O. C. Meirelles, J. A. Landeiro, T. Quirico-Santos, Long-term outcome in patients with recurrent malignant glioma treated with Perillyl alcohol inhalation, Anticancer Res, 33 (2013) 5625-5631.

[38] T. C. Chen, W. Wang, E. B. Golden, S. Thomas, W. Sivakumar, F. M. Hofman, S. G. Louie, A. H. Schönthal, Green tea epigallocatechin gallate enhances therapeutic efficacy of temozolomide in orthotopic mouse glioblastoma models, Cancer Lett, 302 (2011).

[39] T. C. Chen, H. Y. Cho, W. Wang, M. Barath, N. Sharma, F. M. Hofman, A. H. Schönthal, A novel temozolomide-perillyl alcohol conjugate exhibits superior activity against breast cancer cells in vitro and intracranial triple-negative tumor growth in vivo, Mol. Cancer Ther., 13 (2014) 1181-1193.

[40] P. Pyrko, N. Soriano, A. Kardosh, Y. T. Liu, J. Uddin, N. A. Petasis, F. M. Hofman, C. S. Chen, T. C. Chen, A. H. Schönthal, Downregulation of surviving expression and concomitant induction of apoptosis by celecoxib and its non-cyclooxygenase-2-inhibitory analog, dimethylcelecoxib (DMC), in tumor cells in vitro and in vivo, Mol Cancer, 5 (2006) 19.

[41] C. Tristan, N. Shahani, T. W. Sedlak, A. Sawa, The diverse functions of GAPDH: views from different sub-cellular compartments, Cell Signal, 23 (2011) 317-323.

[42] C. O. da Fonseca, H. Khandelia, M. D. Salazar, A. H. Schonthal, O. C. Meireles, T. Quirico-Santos, Perillyl alcohol: Dynamic interactions with the lipid bilayer and implications for long-term inhalational chemotherapy for gliomas, Surg Neurol Int, 7 (2016) 1.

[43] E. Ehrke, C. Arend, R. Dringen, 3-bromopyruvate inhibits glycolysis, depletes cellular glutathione, and compromises the viability of cultured primary rat astrocytes, J Neurosci Res, 93 (2015) 1138-1146.

[44] S. Krishnan, R. M. Miller, B. Tian, R. D. Mullins, M. P. Jacobson, J. Taunton, Design of reversible, cysteine-targeted Michael acceptors guided by kinetic and computational analysis, J Am Chem Soc, 136 (2014) 12624-12630.

[45] M. K. Dennehy, K. A. Richards, G. R. Wernke, Y. Shyr, D. C. Liebler, Cytosolic and nuclear protein targets of thiol-reactive electrophiles, Chem Res Toxicol, 19 (2006) 20-29.

[46] E. Weerapana, C. Wang, G. M. Simon, F. Richter, S. Khare, M. B. Dillon, D. A. Bachovchin, K. Mowen, D. Baker, B. F. Cravatt, Quantitative reactivity profiling predicts functional cysteines in proteomes, Nature, 468 (2010) 790-795.

[47] D. Jardim-Messeder, F. Moreira-Pacheco, 3-Bromopyruvic Acid Inhibits Tricarboxylic Acid Cycle and Glutaminolysis in HepG2 Cells, Anticancer Res, 36 (2016) 2233-2241.

[48] Z. Tang, S. Yuan, Y. Hu, H. Zhang, W. Wu, Z. Zeng, J. Yang, J. Yun, R. Xu, P. Huang, Over-expression of GAPDH in human colorectal carcinoma as a preferred target of 3-bromopyruvate propyl ester, J Bioenerg Biomembr, 44 (2012) 117-125.

[49] Y. Eguchi, S. Shimizu, Y. Tsujimoto, Intracellular ATP levels determine cell death fate by apoptosis or necrosis, Cancer Res, 57 (1997) 1835-1840.

[50] M. Leist, B. Single, A. F. Castoldi, S. Kuhnle, P. Nicotera, Intracellular adenosine triphosphate (ATP) concentration: a switch in the decision between apoptosis and necrosis, J Exp Med, 185 (1997) 1481-1486.

[51] W. X. Zong, C. B. Thompson, Necrotic death as a cell fate, Genes Dev, 20 (2006) 1-15.

[52] P. Lis, P. Jurkiewicz, M. Cal-Bakowska, Y. H. Ko, P. L. Pedersen, A. Goffeau, S. Ulaszewski, Screening the yeast genome for energetic metabolism pathways involved in a phenotypic response to the anti-cancer agent 3-bromopyruvate, Oncotarget, 7 (2016) 10153-10173.

[53] A. Paiardini, A. Tramonti, D. Schirch, G. Giuducci, M. L. di Salvo, A. Fiascarelli, A. Giorgi, B. Maras, F. Cutruzzola, R. Contestabile, Differential 3-bromopyruvate inhibition of cytosolic and mitochondrial human serine hydroxymethyltransferase isoforms, key enzymes in cancer metabolic reprogramming, Biochim Biophys Acta, 1864 (2016) 1506-1517.

[54] M. Ralser, M. M. Wamelink, A. Kowald, B. Gerisch, G. Heeren, E. A. Struys, E. Klipp, C. Jakobs, M. Breitenbach, H. Lehrach, S. Krobitsch, Dynamic rerouting of the carbohydrate flux is key to counteracting oxidative stress, J Biol, 6 (2007) 10.

[55] L. S. Ihrlund, E. Hernlund, O. Khan, M. C. Shoshan, 3-Bromopyruvate as inhibitor of tumour cell energy metabolism and chemopotentiator of platinum drugs, Mol Oncol, 2 (2008) 94-101.

[56] I. Sadowska-Bartosz, R. Szewczyk, L. Jaremko, M. Jaremko, G. Bartosz, Anticancer agent 3-bromopyruvic acid forms a conjugate with glutathione, Pharmacol Rep, 68 (2016) 502-505.

[57] L. Macchioni, M. Davidescu, R. Roberti, L. Corazzi, The energy blockers 3-bromopyruvate and lonidamine: effects on bioenergetics of brain mitochondria, J Bioenerg Biomembr, 46 (2014) 389-394.

[58] X. Guo, X. Zang, T. Wang, S. Xian, Y. Lu, 3-Bromopyruvate and sodium citrate induce apoptosis in human gastric cancer cell line MGC-803 by inhibiting glycolysis and promoting mitochondria-regulated apoptosis pathway, Biochem Biophys Res Commun, 475 (2016) 37-43.

[59] X. Zou, M. Zhang, Y. Sun, S. Zhao, Y. Wei, X. Zhang, C. Jiang, H. Liu, Inhibitory effects of 3-bromopyruvate in human nasopharyngeal carcinoma cells, Oncol Rep, 34 (2015) 1895-1904.

[60] S. Zhang, X. Lou, X. Sin, R. Zhou, S. Liu, N. Xu, D. J. Liao, Necrosis, and then Stress induced necrosis-like cell death, but not apoptosis, should be the preferred cell death mode for chemotherapy: clearance of a few misconceptions, Oncoscience, 1 (2014) 407-422.

[61] M. S. Jurkowitz-Alexander, R. A. Altschuld, C. M. Hohl, S. D. Johnson, L. S. McDonald, T. D. Simmons, L. A. Horrocks, Cell swelling, blebbing, and death are dependent on ATP depletion and independent of calcium during chemical hypoxia in a glial cell line (ROC-1), J Neurochem, 59 (1992) 344-352.

[62] S. L. Fink, B. T. Cookson, Apoptosis, pyroptosis, and necrosis: mechanistic description of dead and dying eukaryotic cells, Infect Immun, 73 (2005) 1907-1916.

[63] P. Golstein, G. Kroemer, Cell death by necrosis: towards a molecular definition, Trends Biochem Sci, 32 (2007) 37-43.

[64] W. Wu, P. Liu, J. Li, Necroptosis: an emerging form of programmed cell death, Crit Rev Oncol Hematol, 82 (2012) 249-258.
[65] B. Alberts, A. Johnson, J. Lewis, D. Morgan, M. Raff, K. Rogerts, P. Walter, Molecular Biology of the Cell, 6th ed., Garland Science, New York, 2015.
[66] C. Richter, M. Schweizer, A. Cossarizza, C. Franceschi, Control of apoptosis by the cellular ATP level, FEBS Lett, 378 (1996) 107-110.
[67] H. Xi, J. C. Barredo, J. R. Merchan, T. J. Lampidis, Endoplasmic reticulum stress induced by 2-deoxyglucose but not glucose starvation activates AMPK through CaMKKbeta leading to autophagy, Biochem Pharmacol, 85 (2013) 1463-1477.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The entire disclosure of each of the patent documents, including certificates of correction, patent application documents, scientific articles, governmental reports, websites, and other references referred to herein is incorporated by reference herein in its entirety for all purposes.

What is claimed is:

1. A conjugate of perillyl alcohol and 3-bromopyruvate that is

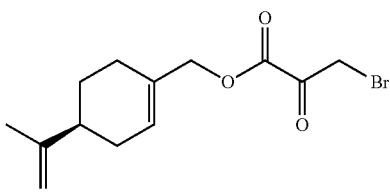 [SMILES: C=C(C)[C@@H]1CC=C(COC(=O)C(=O)CBr)CC1]

3-bromo-2-oxo-propionic acid 4-isopropenyl-cyclohex-1-enylmethyl ester, or a pharmaceutically acceptable salt thereof.

2. A pharmaceutical composition comprising the conjugate according to claim 1, or a pharmaceutically acceptable salt thereof, further comprising a pharmaceutically acceptable excipient.

3. A method of treating a cancer in a patient in need of such treatment, the method comprising administering to said patient a therapeutically effective amount of 3-bromo-2-oxo-propionic acid 4-isopropenyl-cyclohex-1-enylmethyl ester or a pharmaceutically acceptable salt thereof.

4. The method according to claim 3, wherein said cancer is selected from the group consisting of lung cancer, ear, nose and throat cancer, leukemia, colon cancer, melanoma, pancreatic cancer, prostate cancer, breast cancer, hematopoietic cancer, ovarian cancer, basal cell carcinoma, biliary tract cancer; bladder cancer; bone cancer; cervical cancer; choriocarcinoma; colon cancer; connective tissue cancer; cancer of the digestive system; endometrial cancer; eye cancer; cancer of the head and neck; intra-epithelial neoplasm; kidney cancer; larynx cancer; liver cancer; lymphoma myeloma; fibroma, neuroblastoma; oral cavity cancer; retinoblastoma; rhabdomyosarcoma; rectal cancer; renal cancer; cancer of the respiratory system; sarcoma; skin cancer; testicular cancer; thyroid cancer; uterine cancer and cancer of the urinary system.

5. A process for synthesizing 3-bromo-2-oxo-propionic acid 4-isopropenyl-cyclohex-1-enylmethyl ester comprising:
   a) reacting 1,1-dichlorodimethyl ether with bromopyruvic acid to form 3-bromopyruvic chloride; and,
   b) reacting 3-bromopyruvic chloride with perillyl alcohol to form 3-bromo-2-oxo-propionic acid 4-isopropenyl-cyclohex-1-enylmethyl ester.

6. The process according to claim 5 wherein said step of reacting 1,1-dichlorodimethyl ether with bromopyruvic acid is conducted at a temperature of about 0 to about 20° C.

7. The process according to claim 5 wherein said step of reacting 3-bromopyruvic chloride with perillyl alcohol is conducted at a temperature of about −10 to about 10° C.

8. The process according to claim 5 wherein said step of reacting 3-bromopyruvic chloride with perillyl alcohol is conducted in the presence of sodium bicarbonate and n-heptane.

9. The method of claim 4, wherein leukemia is acute myeloid leukemia, acute lymphoid leukemia, chronic myeloid leukemia, and/or chronic lymphoid leukemia.

10. The method of claim 4, wherein lymphoma is Hodgkin's lymphoma and/or Non-Hodgkin's lymphoma.

* * * * *

UNITED STATES PATENT AND TRADEMARK OFFICE
CERTIFICATE OF CORRECTION

| | | |
|---|---|---|
| PATENT NO. | : 10,858,305 B2 | Page 1 of 1 |
| APPLICATION NO. | : 16/465081 | |
| DATED | : December 8, 2020 | |
| INVENTOR(S) | : Thomas Chen | |

It is certified that error appears in the above-identified patent and that said Letters Patent is hereby corrected as shown below:

In the Specification

Before the "FIELD OF INVENTION" Column 1, Line 4, insert the following:
-- STATEMENT OF GOVERNMENT SUPPORT
This invention was made with government support under CA217551 awarded by the National Institutes of Health. The government has certain rights in the invention. --

Signed and Sealed this
Twenty-seventh Day of May, 2025

Coke Morgan Stewart
*Acting Director of the United States Patent and Trademark Office*